(12) United States Patent
Berti

(10) Patent No.: US 9,040,055 B2
(45) Date of Patent: May 26, 2015

(54) CONJUGATION OF STREPTOCOCCAL CAPSULAR SACCHARIDES

(71) Applicant: Novartis Vaccines and Diagnostics SRL, Siena (IT)

(72) Inventor: Francesco Berti, Siena (IT)

(73) Assignee: NOVARTIS VACCINES AND DIAGNOSTICS SRL, Siena (IT)

( * ) Notice: Subject to any disclaimer, the term of this patent is extended or adjusted under 35 U.S.C. 154(b) by 0 days.

(21) Appl. No.: 13/912,919

(22) Filed: Jun. 7, 2013

(65) Prior Publication Data
US 2013/0295132 A1 Nov. 7, 2013

Related U.S. Application Data

(62) Division of application No. 11/883,614, filed as application No. PCT/IB2006/000756 on Feb. 1, 2006, now Pat. No. 8,513,392.

(30) Foreign Application Priority Data

Feb. 1, 2005 (GB) .................................. 0502095.3

(51) Int. Cl.
*A61K 39/09* (2006.01)
*C07K 14/315* (2006.01)
(Continued)

(52) U.S. Cl.
CPC .............. *C07K 14/315* (2013.01); *A61K 39/09* (2013.01); *A61K 47/48261* (2013.01); *A61K 47/48284* (2013.01); *A61K 47/4833* (2013.01); *A61K 2039/6037* (2013.01)

(58) Field of Classification Search
CPC ........ A61K 39/00; A61K 39/09; A61K 39/02
USPC .............................. 424/197.11, 193.11, 193.1
See application file for complete search history.

(56) References Cited

U.S. PATENT DOCUMENTS

| 4,356,170 A | 10/1982 | Jennings et al. |
| 4,761,283 A | 8/1988 | Anderson |

(Continued)

FOREIGN PATENT DOCUMENTS

| WO | 9202817 | 2/1992 |
| WO | 9406467 | 3/1994 |

(Continued)

OTHER PUBLICATIONS

Shen et al, "Preparation and preclinical evaluation of experimental group B streptococcus type III polysaccharide-cholera toxin B subunit conjugate vaccine for intranasal immunization," Vaccine 19, 7-8, Nov. 22, 2001.

(Continued)

*Primary Examiner* — Albert Navarro
*Assistant Examiner* — Ginny Portner
(74) *Attorney, Agent, or Firm* — Banner & Witcoff, Ltd.

(57) ABSTRACT

Three conjugation methods for use with the capsular saccharide of *Streptococcus agalactiae*. In the first method, reductive animation of oxidized sialic acid residue side chains is used, but the aldehyde groups are first aminated, and then the amine is coupled to a carrier via a linker. In the second method, sialic acid residues and/or N-acetyl-glucosamine residues are de-N-acetylated to give amine groups, and the amine groups are coupled to a carrier protein via a linker. In the third method, linkage is via galactose residues in the capsular saccharide rather than sialic acid residues, which can conveniently be achieved using galactose oxidase.

10 Claims, 8 Drawing Sheets

(51) Int. Cl.
*A61K 47/48* (2006.01)
*A61K 39/00* (2006.01)

(56) References Cited

U.S. PATENT DOCUMENTS

| | | | |
|---|---|---|---|
| 4,923,803 A | 5/1990 | Izumori et al. | |
| 5,785,973 A * | 7/1998 | Bixler et al. | 424/196.11 |
| 5,795,580 A | 8/1998 | Jennings et al. | |
| 5,993,825 A | 11/1999 | Jennings et al. | |
| 6,225,462 B1 | 5/2001 | Berry et al. | |
| 6,248,570 B1 * | 6/2001 | Michon et al. | 435/101 |
| 6,372,222 B1 * | 4/2002 | Michon et al. | 424/197.11 |
| 6,426,074 B1 | 7/2002 | Michel et al. | |
| 6,573,245 B1 | 6/2003 | Marciani | |
| 6,656,472 B1 | 12/2003 | Chong et al. | |
| 6,960,344 B2 | 11/2005 | Marciani | |
| 7,128,919 B2 * | 10/2006 | Adderson et al. | 424/244.1 |
| 7,438,912 B2 * | 10/2008 | Meinke et al. | 424/165.1 |
| 7,645,577 B2 * | 1/2010 | Adderson et al. | 435/6.15 |
| 7,700,578 B2 | 4/2010 | Guerry et al. | |
| 7,709,009 B2 * | 5/2010 | Grandi et al. | 424/244.1 |
| 7,892,552 B2 * | 2/2011 | Adderson et al. | 424/165.1 |
| 7,927,607 B2 * | 4/2011 | Meinke et al. | 424/237.1 |
| 7,939,087 B2 * | 5/2011 | Telford et al. | 424/244.1 |
| 7,955,604 B2 * | 6/2011 | Telford et al. | 424/244.1 |
| 8,137,673 B2 * | 3/2012 | Telford et al. | 424/190.1 |
| 8,431,139 B2 * | 4/2013 | Telford et al. | 424/244.1 |
| 8,431,160 B2 * | 4/2013 | O'Hagan et al. | 424/499 |
| 8,449,892 B2 * | 5/2013 | Meinke et al. | 424/244.1 |
| 8,465,751 B2 * | 6/2013 | Manetti et al. | 424/246.1 |
| 8,513,392 B2 * | 8/2013 | Berti | 530/402 |
| 8,529,912 B2 * | 9/2013 | Adderson et al. | 424/244.1 |
| 2001/0051364 A1 * | 12/2001 | Michon et al. | 435/101 |
| 2002/0031526 A1 * | 3/2002 | Michon et al. | 424/197.11 |
| 2003/0170267 A1 | 9/2003 | Paoletti | |
| 2004/0052804 A1 | 3/2004 | Arumugham et al. | |
| 2004/0096461 A1 * | 5/2004 | Michon et al. | 424/203.1 |
| 2004/0142856 A1 | 7/2004 | DeFrees et al. | |
| 2004/0213804 A1 | 10/2004 | Michon | |
| 2005/0169941 A1 | 8/2005 | Lees | |
| 2006/0134142 A1 | 6/2006 | Kasper et al. | |
| 2006/0198819 A1 | 9/2006 | Behrens et al. | |
| 2007/0036828 A1 * | 2/2007 | Rappuoli et al. | 424/239.1 |
| 2007/0110762 A1 | 5/2007 | Jessouroun et al. | |
| 2007/0141084 A1 | 6/2007 | Lee et al. | |
| 2008/0312137 A1 | 12/2008 | Swennen | |
| 2009/0136547 A1 * | 5/2009 | Telford et al. | 424/244.1 |
| 2010/0063270 A1 * | 3/2010 | Costantino | 536/123.1 |
| 2010/0189740 A1 * | 7/2010 | Michon et al. | 424/197.11 |
| 2010/0239600 A1 * | 9/2010 | Bigio et al. | 424/193.1 |
| 2013/0197203 A1 * | 8/2013 | Michon et al. | 530/395 |
| 2013/0273091 A1 * | 10/2013 | Berti et al. | 424/190.1 |

FOREIGN PATENT DOCUMENTS

| | | | | |
|---|---|---|---|---|
| WO | 00/10599 | * | 3/2000 | A61K 39/00 |
| WO | 02/12294 | * | 2/2002 | C07K 14/315 |
| WO | 03007985 | | 1/2003 | |
| WO | 2004/011027 | * | 2/2004 | A61K 39/09 |
| WO | WO2004011027 | | 2/2004 | |
| WO | 2004/041157 | * | 5/2004 | |

OTHER PUBLICATIONS

Shen et al., "Group B streptoccocus capsular polysaccharide-cholera toxin B subunit conjugate vaccines prepared by different methods for intrasal immunization," Inf. Immun. 69, 297-306, Jan. 1, 2001.

Paoletti, Lawrence C et al, The Journal of Biological Chemistry, vol. 265(30) Oct. 25, 1990, pp. 18278-18283, An Oligosaccharide-Tetanus Toxoid Conjugate Vaccine Against Type III Group B Streptococcus.

Kasper, Dennis L et al, Immunochemical Analysis and Immunogenicity of the Type II Group B Streptococcal Capsular Polysaccharide, Journal of Cinical Investigation, vol. 72, Jul. 1983, pp. 260-269.

Wessels, MR et al, The Journal of Biological Chemistry, vol. 266(11) Apr. 15, pp. 6714-6719, 1991, Structural determinations and immunochemical characterization of the Type V Group B Streptococcus Capsular Polysaccharide.

Wessels, MR et al, Journal of Cinical Investigation, 1990, vol. 86, pp. 1428-1433, Immunogenicity in Animals of a Polysaccharide-Protein Conjugate Vaccine Against Type III Group B Streptococcus.

Jennings, H, The Journal of Infectious Diseases, vol. 165, Supplement 1, Epidemiology, Jun. 1992, pp. S156-S159, Further Approaches for Optimizing Polysaccharid-Protein Conjugate Vaccines for Prevention of Invasive Bacterial Disease.

Baker, CJ et al, Infection and Immunity, Jan. 1976, vol. 13(1), pp. 284-288, Indentification of Sialic Acid in Polysaccharide Antigens of Group B Streptococcus.

Bayer, Edward A et al, Analytical Biochemistry, vol. 170, pp. 271-281, 1988, Biocytin hydrazide-A Selective Label for Sialic Acids, Galactose and Other Sugars in Glycoconjugates Using Avidin-Biotin Technology.

* cited by examiner

FIGURE 3

| | |
|---|---|
| Ia | $[\rightarrow 4)\text{-}\beta\text{-D-Glc}p\text{-}(1\rightarrow 4)\text{-}\beta\text{-D-Gal}p\text{-}(1\rightarrow]_n$<br>$\overset{3}{\underset{1}{\uparrow}}$<br>$\beta\text{-D-Glc}p\text{NAc}$<br>$\overset{4}{\underset{1}{\uparrow}}$<br>$\beta\text{-D-Gal}p$<br>$\overset{3}{\underset{2}{\uparrow}}$<br>$\alpha\text{-D-Neu}p\text{NAc}$ |
| Ib | $[\rightarrow 4)\text{-}\beta\text{-D-Glc}p\text{-}(1\rightarrow 4)\text{-}\beta\text{-D-Gal}p\text{-}(1\rightarrow]_n$<br>$\overset{3}{\underset{1}{\uparrow}}$<br>$\beta\text{-D-Glc}p\text{NAc}$<br>$\overset{3}{\underset{1}{\uparrow}}$<br>$\beta\text{-D-Gal}p$<br>$\overset{3}{\underset{2}{\uparrow}}$<br>$\alpha\text{-D-Neu}p\text{NAc}$ |
| II | $[\rightarrow 4)\text{-}\beta\text{-D-Glc}p\text{NAc-}(1\rightarrow 3)\text{-}\beta\text{-D-Gal}p\text{-}(1\rightarrow 4)\text{-}\beta\text{-D-Glc}p\text{-}(1\rightarrow 3)\text{-}\beta\text{-D-Glc}p\text{-}(1\rightarrow 2)\text{-}\beta\text{-D-Gal}p\text{-}(1\rightarrow]_n$<br>$\overset{6}{\underset{1}{\uparrow}} \qquad\qquad\qquad\qquad\qquad\qquad\qquad\qquad\qquad\qquad\qquad\qquad \overset{3}{\underset{2}{\uparrow}}$<br>$\beta\text{-D-Gal}p \qquad\qquad\qquad\qquad\qquad\qquad\qquad\qquad\qquad\qquad\qquad \alpha\text{-D-Neu}p\text{NAc}$ |
| III | $\rightarrow 4)\text{-}\beta\text{-D-Glc}p\text{-}(1\rightarrow 6)\text{-}\beta\text{-D-Glc}p\text{NAc-}(1\rightarrow 3)\text{-}\beta\text{-D-Gal}p\text{-}(1\rightarrow$<br>$\overset{4}{\underset{1}{\uparrow}}$<br>$\beta\text{-D-Gal}p$<br>$\overset{3}{\underset{2}{\uparrow}}$<br>$\alpha\text{-D-Neu}p\text{NAc}$ |
| V | $\rightarrow 4)\text{-}\alpha\text{-D-Glc}p\text{-}(1\rightarrow 4)\text{-}\beta\text{-D-Gal}p\text{-}(1\rightarrow 4)\text{-}\beta\text{-D-Glc}p\text{-}(1\rightarrow$<br>$\overset{6}{\underset{1}{\uparrow}} \qquad\qquad\qquad \overset{3}{\underset{1}{\uparrow}}$<br>$\beta\text{-D-Glc}p\text{NAc} \quad \beta\text{-D-Glc}p$<br>$\overset{4}{\underset{1}{\uparrow}}$<br>$\beta\text{-D-Gal}p$<br>$\overset{3}{\underset{2}{\uparrow}}$<br>$\alpha\text{-D-Neu}p\text{NAc}$ |

SEQUENCE LISTING

<160> NUMBER OF SEQ ID NOS: 19

<210> SEQ ID NO 1
<211> LENGTH: 901
<212> TYPE: PRT
<213> ORGANISM: Streptococcus agalactiae

<400> SEQUENCE: 1

Met Arg Lys Tyr Gln Lys Phe Ser Lys Ile Leu Thr Leu Ser Leu Phe
1               5                   10                  15

Cys Leu Ser Gln Ile Pro Leu Asn Thr Asn Val Leu Gly Glu Ser Thr
            20                  25                  30

Val Pro Glu Asn Gly Ala Lys Gly Lys Leu Val Val Lys Lys Thr Asp
        35                  40                  45

Asp Gln Asn Lys Pro Leu Ser Lys Ala Thr Phe Val Leu Lys Thr Thr
    50                  55                  60

Ala His Pro Glu Ser Lys Ile Glu Lys Val Thr Ala Glu Leu Thr Gly
65                  70                  75                  80

Glu Ala Thr Phe Asp Asn Leu Ile Pro Gly Asp Tyr Thr Leu Ser Glu
                85                  90                  95

Glu Thr Ala Pro Glu Gly Tyr Lys Lys Thr Asn Gln Thr Trp Gln Val
            100                 105                 110

Lys Val Glu Ser Asn Gly Lys Thr Thr Ile Gln Asn Ser Gly Asp Lys
        115                 120                 125

Asn Ser Thr Ile Gly Gln Asn Gln Glu Leu Asp Lys Gln Tyr Pro
    130                 135                 140

Pro Thr Gly Ile Tyr Glu Asp Thr Lys Glu Ser Tyr Lys Leu Glu His
145                 150                 155                 160

Val Lys Gly Ser Val Pro Asn Gly Lys Ser Glu Ala Lys Ala Val Asn
                165                 170                 175

Pro Tyr Ser Ser Glu Gly Glu His Ile Arg Glu Ile Pro Glu Gly Thr
            180                 185                 190

Leu Ser Lys Arg Ile Ser Glu Val Gly Asp Leu Ala His Asn Lys Tyr
        195                 200                 205

Lys Ile Glu Leu Thr Val Ser Gly Lys Thr Ile Val Lys Pro Val Asp
    210                 215                 220

Lys Gln Lys Pro Leu Asp Val Val Phe Val Leu Asp Asn Ser Asn Ser
225                 230                 235                 240

Met Asn Asn Asp Gly Pro Asn Phe Gln Arg His Asn Lys Ala Lys Lys

```
                    245                 250                 255
Ala Ala Glu Ala Leu Gly Thr Ala Val Lys Asp Ile Leu Gly Ala Asn
                260                 265                 270

Ser Asp Asn Arg Val Ala Leu Val Thr Tyr Gly Ser Asp Ile Phe Asp
            275                 280                 285

Gly Arg Ser Val Asp Val Val Lys Gly Phe Lys Glu Asp Asp Lys Tyr
        290                 295                 300

Tyr Gly Leu Gln Thr Lys Phe Thr Ile Gln Thr Glu Asn Tyr Ser His
305                 310                 315                 320

Lys Gln Leu Thr Asn Asn Ala Glu Glu Ile Ile Lys Arg Ile Pro Thr
                325                 330                 335

Glu Ala Pro Lys Ala Lys Trp Gly Ser Thr Thr Asn Gly Leu Thr Pro
            340                 345                 350

Glu Gln Gln Lys Glu Tyr Tyr Leu Ser Lys Val Gly Glu Thr Phe Thr
        355                 360                 365

Met Lys Ala Phe Met Glu Ala Asp Asp Ile Leu Ser Gln Val Asn Arg
370                 375                 380

Asn Ser Gln Lys Ile Ile Val His Val Thr Asp Gly Val Pro Thr Arg
385                 390                 395                 400

Ser Tyr Ala Ile Asn Asn Phe Lys Leu Gly Ala Ser Tyr Glu Ser Gln
                405                 410                 415

Phe Glu Gln Met Lys Lys Asn Gly Tyr Leu Asn Lys Ser Asn Phe Leu
            420                 425                 430

Leu Thr Asp Lys Pro Glu Asp Ile Lys Gly Asn Gly Glu Ser Tyr Phe
        435                 440                 445

Leu Phe Pro Leu Asp Ser Tyr Gln Thr Gln Ile Ile Ser Gly Asn Leu
        450                 455                 460

Gln Lys Leu His Tyr Leu Asp Leu Asn Leu Asn Tyr Pro Lys Gly Thr
465                 470                 475                 480

Ile Tyr Arg Asn Gly Pro Val Lys Glu His Gly Thr Pro Thr Lys Leu
                485                 490                 495

Tyr Ile Asn Ser Leu Lys Gln Lys Asn Tyr Asp Ile Phe Asn Phe Gly
            500                 505                 510

Ile Asp Ile Ser Gly Phe Arg Gln Val Tyr Asn Glu Glu Tyr Lys Lys
        515                 520                 525

Asn Gln Asp Gly Thr Phe Gln Lys Leu Lys Glu Glu Ala Phe Lys Leu
        530                 535                 540

Ser Asp Gly Glu Ile Thr Glu Leu Met Arg Ser Phe Ser Ser Lys Pro
545                 550                 555                 560

Glu Tyr Tyr Thr Pro Ile Val Thr Ser Ala Asp Thr Ser Asn Asn Glu
                565                 570                 575

Ile Leu Ser Lys Ile Gln Gln Phe Glu Thr Ile Leu Thr Lys Glu
            580                 585                 590

Asn Ser Ile Val Asn Gly Thr Ile Glu Asp Pro Met Gly Asp Lys Ile
            595                 600                 605

Asn Leu Gln Leu Gly Asn Gly Gln Thr Leu Gln Pro Ser Asp Tyr Thr
        610                 615                 620

Leu Gln Gly Asn Asp Gly Ser Val Met Lys Asp Gly Ile Ala Thr Gly
625                 630                 635                 640

Gly Pro Asn Asn Asp Gly Gly Ile Leu Lys Gly Val Lys Leu Glu Tyr
                645                 650                 655

Ile Gly Asn Lys Leu Tyr Val Arg Gly Leu Asn Leu Gly Glu Gly Gln
            660                 665                 670
```

```
Lys Val Thr Leu Thr Tyr Asp Val Lys Leu Asp Asp Ser Phe Ile Ser
            675                 680                 685

Asn Lys Phe Tyr Asp Thr Asn Gly Arg Thr Thr Leu Asn Pro Lys Ser
        690                 695                 700

Glu Asp Pro Asn Thr Leu Arg Asp Phe Pro Ile Pro Lys Ile Arg Asp
705                 710                 715                 720

Val Arg Glu Tyr Pro Thr Ile Thr Ile Lys Asn Glu Lys Lys Leu Gly
                725                 730                 735

Glu Ile Glu Phe Ile Lys Val Asp Lys Asp Asn Asn Lys Leu Leu Leu
            740                 745                 750

Lys Gly Ala Thr Phe Glu Leu Gln Glu Phe Asn Glu Asp Tyr Lys Leu
            755                 760                 765

Tyr Leu Pro Ile Lys Asn Asn Asn Ser Lys Val Val Thr Gly Glu Asn
        770                 775                 780

Gly Lys Ile Ser Tyr Lys Asp Leu Lys Asp Gly Lys Tyr Gln Leu Ile
785                 790                 795                 800

Glu Ala Val Ser Pro Glu Asp Tyr Gln Lys Ile Thr Asn Lys Pro Ile
                805                 810                 815

Leu Thr Phe Glu Val Val Lys Gly Ser Ile Lys Asn Ile Ile Ala Val
            820                 825                 830

Asn Lys Gln Ile Ser Glu Tyr His Glu Glu Gly Asp Lys His Leu Ile
            835                 840                 845

Thr Asn Thr His Ile Pro Pro Lys Gly Ile Ile Pro Met Thr Gly Gly
        850                 855                 860

Lys Gly Ile Leu Ser Phe Ile Leu Ile Gly Gly Ala Met Met Ser Ile
865                 870                 875                 880

Ala Gly Gly Ile Tyr Ile Trp Lys Arg Tyr Lys Lys Ser Ser Asp Met
                885                 890                 895

Ser Ile Lys Lys Asp
            900

<210> SEQ ID NO 2
<211> LENGTH: 554
<212> TYPE: PRT
<213> ORGANISM: Streptococcus agalactiae

<400> SEQUENCE: 2

Met Lys Leu Ser Lys Lys Leu Leu Phe Ser Ala Ala Val Leu Thr Met
1               5                   10                  15

Val Ala Gly Ser Thr Val Glu Pro Val Ala Gln Phe Ala Thr Gly Met
            20                  25                  30

Ser Ile Val Arg Ala Ala Glu Val Ser Gln Glu Arg Pro Ala Lys Thr
        35                  40                  45

Thr Val Asn Ile Tyr Lys Leu Gln Ala Asp Ser Tyr Lys Ser Glu Ile
    50                  55                  60

Thr Ser Asn Gly Gly Ile Glu Asn Lys Asp Gly Glu Val Ile Ser Asn
65                  70                  75                  80

Tyr Ala Lys Leu Gly Asp Asn Val Lys Gly Leu Gln Gly Val Gln Phe
                85                  90                  95

Lys Arg Tyr Lys Val Lys Thr Asp Ile Ser Val Asp Glu Leu Lys Lys
                100                 105                 110

Leu Thr Thr Val Glu Ala Ala Asp Ala Lys Val Gly Thr Ile Leu Glu
            115                 120                 125

Glu Gly Val Ser Leu Pro Gln Lys Thr Asn Ala Gln Gly Leu Val Val
```

```
            130             135             140
Asp Ala Leu Asp Ser Lys Ser Asn Val Arg Tyr Leu Tyr Val Glu Asp
145                 150                 155                 160

Leu Lys Asn Ser Pro Ser Asn Ile Thr Lys Ala Tyr Ala Val Pro Phe
                165                 170                 175

Val Leu Glu Leu Pro Val Ala Asn Ser Thr Gly Thr Gly Phe Leu Ser
            180                 185                 190

Glu Ile Asn Ile Tyr Pro Lys Asn Val Val Thr Asp Glu Pro Lys Thr
        195                 200                 205

Asp Lys Asp Val Lys Lys Leu Gly Gln Asp Asp Ala Gly Tyr Thr Ile
    210                 215                 220

Gly Glu Glu Phe Lys Trp Phe Leu Lys Ser Thr Ile Pro Ala Asn Leu
225                 230                 235                 240

Gly Asp Tyr Glu Lys Phe Glu Ile Thr Asp Lys Phe Ala Asp Gly Leu
                245                 250                 255

Thr Tyr Lys Ser Val Gly Lys Ile Lys Ile Gly Ser Lys Thr Leu Asn
            260                 265                 270

Arg Asp Glu His Tyr Thr Ile Asp Glu Pro Thr Val Asp Asn Gln Asn
        275                 280                 285

Thr Leu Lys Ile Thr Phe Lys Pro Glu Lys Phe Lys Glu Ile Ala Glu
    290                 295                 300

Leu Leu Lys Gly Met Thr Leu Val Lys Asn Gln Asp Ala Leu Asp Lys
305                 310                 315                 320

Ala Thr Ala Asn Thr Asp Asp Ala Ala Phe Leu Glu Ile Pro Val Ala
                325                 330                 335

Ser Thr Ile Asn Glu Lys Ala Val Leu Gly Lys Ala Ile Glu Asn Thr
            340                 345                 350

Phe Glu Leu Gln Tyr Asp His Thr Pro Asp Lys Ala Asp Asn Pro Lys
        355                 360                 365

Pro Ser Asn Pro Pro Arg Lys Pro Glu Val His Thr Gly Gly Lys Arg
    370                 375                 380

Phe Val Lys Lys Asp Ser Thr Glu Thr Gln Thr Leu Gly Gly Ala Glu
385                 390                 395                 400

Phe Asp Leu Leu Ala Ser Asp Gly Thr Ala Val Lys Trp Thr Asp Ala
                405                 410                 415

Leu Ile Lys Ala Asn Thr Asn Lys Asn Tyr Ile Ala Gly Glu Ala Val
            420                 425                 430

Thr Gly Gln Pro Ile Lys Leu Lys Ser His Thr Asp Gly Thr Phe Glu
        435                 440                 445

Ile Lys Gly Leu Ala Tyr Ala Val Asp Ala Asn Ala Glu Gly Thr Ala
    450                 455                 460

Val Thr Tyr Lys Leu Lys Glu Thr Lys Ala Pro Glu Gly Tyr Val Ile
465                 470                 475                 480

Pro Asp Lys Glu Ile Glu Phe Thr Val Ser Gln Thr Ser Tyr Asn Thr
                485                 490                 495

Lys Pro Thr Asp Ile Thr Val Asp Ser Ala Asp Ala Thr Pro Asp Thr
            500                 505                 510

Ile Lys Asn Asn Lys Arg Pro Ser Ile Pro Asn Thr Gly Gly Ile Gly
        515                 520                 525

Thr Ala Ile Phe Val Ala Ile Gly Ala Ala Val Met Ala Phe Ala Val
    530                 535                 540

Lys Gly Met Lys Arg Arg Thr Lys Asp Asn
545                 550
```

<210> SEQ ID NO 3
<211> LENGTH: 890
<212> TYPE: PRT
<213> ORGANISM: Streptococcus agalactiae

<400> SEQUENCE: 3

```
Met Lys Lys Arg Gln Lys Ile Trp Arg Gly Leu Ser Val Thr Leu Leu
1               5                   10                  15
Ile Leu Ser Gln Ile Pro Phe Gly Ile Leu Val Gln Gly Glu Thr Gln
            20                  25                  30
Asp Thr Asn Gln Ala Leu Gly Lys Val Ile Val Lys Lys Thr Gly Asp
        35                  40                  45
Asn Ala Thr Pro Leu Gly Lys Ala Thr Phe Val Leu Lys Asn Asp Asn
    50                  55                  60
Asp Lys Ser Glu Thr Ser His Glu Thr Val Glu Gly Ser Gly Glu Ala
65                  70                  75                  80
Thr Phe Glu Asn Ile Lys Pro Gly Asp Tyr Thr Leu Arg Glu Glu Thr
                85                  90                  95
Ala Pro Ile Gly Tyr Lys Lys Thr Asp Lys Thr Trp Lys Val Lys Val
            100                 105                 110
Ala Asp Asn Gly Ala Thr Ile Ile Glu Gly Met Asp Ala Asp Lys Ala
        115                 120                 125
Glu Lys Arg Lys Glu Val Leu Asn Ala Gln Tyr Pro Lys Ser Ala Ile
    130                 135                 140
Tyr Glu Asp Thr Lys Glu Asn Tyr Pro Leu Val Asn Val Glu Gly Ser
145                 150                 155                 160
Lys Val Gly Glu Gln Tyr Lys Ala Leu Asn Pro Ile Asn Gly Lys Asp
                165                 170                 175
Gly Arg Arg Glu Ile Ala Glu Gly Trp Leu Ser Lys Lys Ile Thr Gly
            180                 185                 190
Val Asn Asp Leu Asp Lys Asn Lys Tyr Lys Ile Glu Leu Thr Val Glu
        195                 200                 205
Gly Lys Thr Thr Val Glu Thr Lys Glu Leu Asn Gln Pro Leu Asp Val
    210                 215                 220
Val Val Leu Leu Asp Asn Ser Asn Ser Met Asn Asn Glu Arg Ala Asn
225                 230                 235                 240
Asn Ser Gln Arg Ala Leu Lys Ala Gly Glu Ala Val Glu Lys Leu Ile
                245                 250                 255
Asp Lys Ile Thr Ser Asn Lys Asp Asn Arg Val Ala Leu Val Thr Tyr
            260                 265                 270
Ala Ser Thr Ile Phe Asp Gly Thr Glu Ala Thr Val Ser Lys Gly Val
        275                 280                 285
Ala Asp Gln Asn Gly Lys Ala Leu Asn Asp Ser Val Ser Trp Asp Tyr
    290                 295                 300
His Lys Thr Thr Phe Thr Ala Thr Thr His Asn Tyr Ser Tyr Leu Asn
305                 310                 315                 320
Leu Thr Asn Asp Ala Asn Glu Val Asn Ile Leu Lys Ser Arg Ile Pro
                325                 330                 335
Lys Glu Ala Glu His Ile Asn Gly Asp Arg Thr Leu Tyr Gln Phe Gly
            340                 345                 350
Ala Thr Phe Thr Gln Lys Ala Leu Met Lys Ala Asn Glu Ile Leu Glu
        355                 360                 365
Thr Gln Ser Ser Asn Ala Arg Lys Lys Leu Ile Phe His Val Thr Asp
```

-continued

```
                370                 375                 380
Gly Val Pro Thr Met Ser Tyr Ala Ile Asn Phe Asn Pro Tyr Ile Ser
385                 390                 395                 400

Thr Ser Tyr Gln Asn Gln Phe Asn Ser Phe Leu Asn Lys Ile Pro Asp
                405                 410                 415

Arg Ser Gly Ile Leu Gln Glu Asp Phe Ile Ile Asn Gly Asp Asp Tyr
                420                 425                 430

Gln Ile Val Lys Gly Asp Gly Glu Ser Phe Lys Leu Phe Ser Asp Arg
                435                 440                 445

Lys Val Pro Val Thr Gly Gly Thr Thr Gln Ala Ala Tyr Arg Val Pro
450                 455                 460

Gln Asn Gln Leu Ser Val Met Ser Asn Glu Gly Tyr Ala Ile Asn Ser
465                 470                 475                 480

Gly Tyr Ile Tyr Leu Tyr Trp Arg Asp Tyr Asn Trp Val Tyr Pro Phe
                485                 490                 495

Asp Pro Lys Thr Lys Val Ser Ala Thr Lys Gln Ile Lys Thr His
                500                 505                 510

Gly Glu Pro Thr Thr Leu Tyr Phe Asn Gly Asn Ile Arg Pro Lys Gly
                515                 520                 525

Tyr Asp Ile Phe Thr Val Gly Ile Gly Val Asn Gly Asp Pro Gly Ala
                530                 535                 540

Thr Pro Leu Glu Ala Glu Lys Phe Met Gln Ser Ile Ser Ser Lys Thr
545                 550                 555                 560

Glu Asn Tyr Thr Asn Val Asp Asp Thr Asn Lys Ile Tyr Asp Glu Leu
                565                 570                 575

Asn Lys Tyr Phe Lys Thr Ile Val Glu Glu Lys His Ser Ile Val Asp
                580                 585                 590

Gly Asn Val Thr Asp Pro Met Gly Glu Met Ile Glu Phe Gln Leu Lys
                595                 600                 605

Asn Gly Gln Ser Phe Thr His Asp Asp Tyr Val Leu Val Gly Asn Asp
                610                 615                 620

Gly Ser Gln Leu Lys Asn Gly Val Ala Leu Gly Gly Pro Asn Ser Asp
625                 630                 635                 640

Gly Gly Ile Leu Lys Asp Val Thr Val Thr Tyr Asp Lys Thr Ser Gln
                645                 650                 655

Thr Ile Lys Ile Asn His Leu Asn Leu Gly Ser Gly Gln Lys Val Val
                660                 665                 670

Leu Thr Tyr Asp Val Arg Leu Lys Asp Asn Tyr Ile Ser Asn Lys Phe
                675                 680                 685

Tyr Asn Thr Asn Asn Arg Thr Thr Leu Ser Pro Lys Ser Glu Lys Glu
                690                 695                 700

Pro Asn Thr Ile Arg Asp Phe Pro Ile Pro Lys Ile Arg Asp Val Arg
705                 710                 715                 720

Glu Phe Pro Val Leu Thr Ile Ser Asn Gln Lys Lys Met Gly Glu Val
                725                 730                 735

Glu Phe Ile Lys Val Asn Lys Asp Lys His Ser Glu Ser Leu Leu Gly
                740                 745                 750

Ala Lys Phe Gln Leu Gln Ile Glu Lys Asp Phe Ser Gly Tyr Lys Gln
                755                 760                 765

Phe Val Pro Glu Gly Ser Asp Val Thr Thr Lys Asn Asp Gly Lys Ile
770                 775                 780

Tyr Phe Lys Ala Leu Gln Asp Gly Asn Tyr Lys Leu Tyr Glu Ile Ser
785                 790                 795                 800
```

```
Ser Pro Asp Gly Tyr Ile Glu Val Lys Thr Lys Pro Val Val Thr Phe
                805                 810                 815

Thr Ile Gln Asn Gly Glu Val Thr Asn Leu Lys Ala Asp Pro Asn Ala
            820                 825                 830

Asn Lys Asn Gln Ile Gly Tyr Leu Glu Gly Asn Gly Lys His Leu Ile
        835                 840                 845

Thr Asn Thr Pro Lys Arg Pro Pro Gly Val Phe Pro Lys Thr Gly Gly
850                 855                 860

Ile Gly Thr Ile Val Tyr Ile Leu Val Gly Ser Thr Phe Met Ile Leu
865                 870                 875                 880

Thr Ile Cys Ser Phe Arg Arg Lys Gln Leu
                885                 890

<210> SEQ ID NO 4
<211> LENGTH: 1134
<212> TYPE: PRT
<213> ORGANISM: Streptococcus agalactiae

<400> SEQUENCE: 4

Met Arg Lys Lys Gln Lys Leu Pro Phe Asp Lys Leu Ala Ile Ala Leu
1               5                   10                  15

Ile Ser Thr Ser Ile Leu Leu Asn Ala Gln Ser Asp Ile Lys Ala Asn
            20                  25                  30

Thr Val Thr Glu Asp Thr Pro Ala Thr Glu Gln Ala Val Glu Pro Pro
        35                  40                  45

Gln Pro Ile Ala Val Ser Glu Glu Ser Arg Ser Ser Lys Glu Thr Lys
    50                  55                  60

Thr Ser Gln Thr Pro Ser Asp Val Gly Glu Thr Val Ala Asp Asp Ala
65                  70                  75                  80

Asn Asp Leu Ala Pro Gln Ala Pro Ala Lys Thr Ala Asp Thr Pro Ala
                85                  90                  95

Thr Ser Lys Ala Thr Ile Arg Asp Leu Asn Asp Pro Ser His Val Lys
            100                 105                 110

Thr Leu Gln Glu Lys Ala Gly Lys Gly Ala Gly Thr Val Val Ala Val
        115                 120                 125

Ile Asp Ala Gly Phe Asp Lys Asn His Glu Ala Trp Arg Leu Thr Asp
    130                 135                 140

Lys Thr Lys Ala Arg Tyr Gln Ser Lys Glu Asn Leu Glu Lys Ala Lys
145                 150                 155                 160

Lys Glu His Gly Ile Thr Tyr Gly Glu Trp Val Asn Asp Lys Val Ala
                165                 170                 175

Tyr Tyr His Asp Tyr Ser Lys Asp Gly Lys Asn Ala Val Asp Gln Glu
            180                 185                 190

His Gly Thr His Val Ser Gly Ile Leu Ser Gly Asn Ala Pro Ser Glu
        195                 200                 205

Met Lys Glu Pro Tyr Arg Leu Glu Gly Ala Met Pro Glu Ala Gln Leu
    210                 215                 220

Leu Leu Met Arg Val Glu Ile Val Asn Gly Leu Ala Asp Tyr Ala Arg
225                 230                 235                 240

Asn Tyr Ala Gln Ala Ile Arg Asp Ala Val Asn Leu Gly Ala Lys Val
                245                 250                 255

Ile Asn Met Ser Phe Gly Asn Ala Ala Leu Ala Tyr Ala Asn Leu Pro
            260                 265                 270

Asp Glu Thr Lys Lys Ala Phe Asp Tyr Ala Lys Ser Lys Gly Val Ser
```

```
            275                 280                 285
Ile Val Thr Ser Ala Gly Asn Asp Ser Ser Phe Gly Gly Lys Pro Arg
290                 295                 300

Leu Pro Leu Ala Asp His Pro Asp Tyr Gly Val Val Gly Thr Pro Ala
305                 310                 315                 320

Ala Ala Asp Ser Thr Leu Thr Val Ala Ser Tyr Ser Pro Asp Lys Gln
                        325                 330                 335

Leu Thr Glu Thr Ala Thr Val Lys Thr Asp Asp His Gln Asp Lys Glu
                340                 345                 350

Met Pro Val Ile Ser Thr Asn Arg Phe Glu Pro Asn Lys Ala Tyr Asp
            355                 360                 365

Tyr Ala Tyr Ala Asn Arg Gly Thr Lys Glu Asp Asp Phe Lys Asp Val
370                 375                 380

Glu Gly Lys Ile Ala Leu Ile Glu Arg Gly Asp Ile Asp Phe Lys Asp
385                 390                 395                 400

Lys Ile Ala Asn Ala Lys Lys Ala Gly Ala Val Gly Val Leu Ile Tyr
                        405                 410                 415

Asp Asn Gln Asp Lys Gly Phe Pro Ile Glu Leu Pro Asn Val Asp Gln
                420                 425                 430

Met Pro Ala Ala Phe Ile Ser Arg Arg Asp Gly Leu Leu Leu Lys Asp
            435                 440                 445

Asn Pro Pro Lys Thr Ile Thr Phe Asn Ala Thr Pro Lys Val Leu Pro
450                 455                 460

Thr Ala Ser Gly Thr Lys Leu Ser Arg Phe Ser Ser Trp Gly Leu Thr
465                 470                 475                 480

Ala Asp Gly Asn Ile Lys Pro Asp Ile Ala Ala Pro Gly Gln Asp Ile
                        485                 490                 495

Leu Ser Ser Val Ala Asn Asn Lys Tyr Ala Lys Leu Ser Gly Thr Ser
                500                 505                 510

Met Ser Ala Pro Leu Val Ala Gly Ile Met Gly Leu Leu Gln Lys Gln
            515                 520                 525

Tyr Glu Thr Gln Tyr Pro Asp Met Thr Pro Ser Glu Arg Leu Asp Leu
530                 535                 540

Ala Lys Lys Val Leu Met Ser Ser Ala Thr Ala Leu Tyr Asp Glu Asp
545                 550                 555                 560

Glu Lys Ala Tyr Phe Ser Pro Arg Gln Gln Gly Ala Gly Ala Val Asp
                        565                 570                 575

Ala Lys Lys Ala Ser Ala Ala Thr Met Tyr Val Thr Asp Lys Asp Asn
                580                 585                 590

Thr Ser Ser Lys Val His Leu Asn Asn Val Ser Asp Lys Phe Glu Val
            595                 600                 605

Thr Val Thr Val His Asn Lys Ser Asp Lys Pro Gln Glu Leu Tyr Tyr
610                 615                 620

Gln Val Thr Val Gln Thr Asp Lys Val Asp Gly Lys His Phe Ala Leu
625                 630                 635                 640

Ala Pro Lys Ala Leu Tyr Glu Thr Ser Trp Gln Lys Ile Thr Ile Pro
                        645                 650                 655

Ala Asn Ser Ser Lys Gln Val Thr Val Pro Ile Asp Ala Ser Arg Phe
                660                 665                 670

Ser Lys Asp Leu Leu Ala Gln Met Lys Asn Gly Tyr Phe Leu Glu Gly
            675                 680                 685

Phe Val Arg Phe Lys Gln Asp Pro Thr Lys Glu Glu Leu Met Ser Ile
690                 695                 700
```

```
Pro Tyr Ile Gly Phe Arg Gly Asp Phe Gly Asn Leu Ser Ala Leu Glu
705                 710                 715                 720

Lys Pro Ile Tyr Asp Ser Lys Asp Gly Ser Ser Tyr Tyr His Glu Ala
            725                 730                 735

Asn Ser Asp Ala Lys Asp Gln Leu Asp Gly Asp Gly Leu Gln Phe Tyr
        740                 745                 750

Ala Leu Lys Asn Asn Phe Thr Ala Leu Thr Thr Glu Ser Asn Pro Trp
    755                 760                 765

Thr Ile Ile Lys Ala Val Lys Glu Gly Val Glu Asn Ile Glu Asp Ile
770                 775                 780

Glu Ser Ser Glu Ile Thr Glu Thr Ile Phe Ala Gly Thr Phe Ala Lys
785                 790                 795                 800

Gln Asp Asp Asp Ser His Tyr Tyr Ile His Arg His Ala Asn Gly Lys
                805                 810                 815

Pro Tyr Ala Ala Ile Ser Pro Asn Gly Asp Gly Asn Arg Asp Tyr Val
            820                 825                 830

Gln Phe Gln Gly Thr Phe Leu Arg Asn Ala Lys Asn Leu Val Ala Glu
        835                 840                 845

Val Leu Asp Lys Glu Gly Asn Val Val Trp Thr Ser Glu Val Thr Glu
    850                 855                 860

Gln Val Val Lys Asn Tyr Asn Asn Asp Leu Ala Ser Thr Leu Gly Ser
865                 870                 875                 880

Thr Arg Phe Glu Lys Thr Arg Trp Asp Gly Lys Asp Lys Asp Gly Lys
                885                 890                 895

Val Val Ala Asn Gly Thr Tyr Thr Tyr Arg Val Arg Tyr Thr Pro Ile
            900                 905                 910

Ser Ser Gly Ala Lys Glu Gln His Thr Asp Phe Asp Val Ile Val Asp
        915                 920                 925

Asn Thr Thr Pro Glu Val Ala Thr Ser Ala Thr Phe Ser Thr Glu Asp
    930                 935                 940

Ser Arg Leu Thr Leu Ala Ser Lys Pro Lys Thr Ser Gln Pro Val Tyr
945                 950                 955                 960

Arg Glu Arg Ile Ala Tyr Thr Tyr Met Asp Gly Asp Leu Pro Thr Thr
                965                 970                 975

Glu Tyr Ile Ser Pro Asn Glu Asp Gly Thr Phe Thr Leu Pro Glu Glu
            980                 985                 990

Ala Glu Thr Met Glu Gly Ala Thr Val Pro Leu Lys Met Ser Asp Phe
        995                 1000                1005

Thr Tyr Val Val Glu Asp Met Ala Gly Asn Ile Thr Tyr Thr Pro Val
    1010                1015                1020

Thr Lys Leu Leu Glu Gly His Ser Asn Lys Pro Glu Gln Asp Gly Ser
1025                1030                1035                1040

Asp Gln Ala Pro Asp Lys Lys Pro Glu Ala Lys Pro Glu Gln Asp Gly
                1045                1050                1055

Ser Gly Gln Thr Pro Asp Lys Lys Glu Thr Lys Pro Glu Lys Asp
            1060                1065                1070

Ser Ser Gly Gln Thr Pro Gly Lys Thr Pro Gln Lys Gly Gln Ser Ser
        1075                1080                1085

Arg Thr Leu Glu Lys Arg Ser Ser Lys Arg Ala Leu Ala Thr Lys Ala
    1090                1095                1100

Ser Thr Arg Asp Gln Leu Pro Thr Thr Asn Asp Lys Asp Thr Asn Arg
1105                1110                1115                1120
```

```
Leu His Leu Leu Lys Leu Val Met Thr Thr Phe Phe Leu Gly
            1125                1130

<210> SEQ ID NO 5
<211> LENGTH: 432
<212> TYPE: PRT
<213> ORGANISM: Streptococcus agalactiae

<400> SEQUENCE: 5

Met Asn Lys Lys Val Leu Leu Thr Ser Thr Met Ala Ala Ser Leu Leu
1               5                   10                  15

Ser Val Ala Ser Val Gln Ala Gln Glu Thr Asp Thr Thr Trp Thr Ala
            20                  25                  30

Arg Thr Val Ser Glu Val Lys Ala Asp Leu Val Lys Gln Asp Asn Lys
        35                  40                  45

Ser Ser Tyr Thr Val Lys Tyr Gly Asp Thr Leu Ser Val Ile Ser Glu
    50                  55                  60

Ala Met Ser Ile Asp Met Asn Val Leu Ala Lys Ile Asn Asn Ile Ala
65                  70                  75                  80

Asp Ile Asn Leu Ile Tyr Pro Glu Thr Thr Leu Thr Val Thr Tyr Asp
                85                  90                  95

Gln Lys Ser His Thr Ala Thr Ser Met Lys Ile Glu Thr Pro Ala Thr
            100                 105                 110

Asn Ala Ala Gly Gln Thr Thr Ala Thr Val Asp Leu Lys Thr Asn Gln
        115                 120                 125

Val Ser Val Ala Asp Gln Lys Val Ser Leu Asn Thr Ile Ser Glu Gly
    130                 135                 140

Met Thr Pro Glu Ala Ala Thr Thr Ile Val Ser Pro Met Lys Thr Tyr
145                 150                 155                 160

Ser Ser Ala Pro Ala Leu Lys Ser Lys Glu Val Leu Ala Gln Glu Gln
                165                 170                 175

Ala Val Ser Gln Ala Ala Asn Glu Gln Val Ser Pro Ala Pro Val
            180                 185                 190

Lys Ser Ile Thr Ser Glu Val Pro Ala Ala Lys Glu Glu Val Lys Pro
        195                 200                 205

Thr Gln Thr Ser Val Ser Gln Ser Thr Thr Val Ser Pro Ala Ser Val
    210                 215                 220

Ala Ala Glu Thr Pro Ala Pro Val Ala Lys Val Ala Pro Val Arg Thr
225                 230                 235                 240

Val Ala Ala Pro Arg Val Ala Ser Val Lys Val Thr Pro Lys Val
                245                 250                 255

Glu Thr Gly Ala Ser Pro Glu His Val Ser Ala Pro Ala Val Pro Val
            260                 265                 270

Thr Thr Thr Ser Pro Ala Thr Asp Ser Lys Leu Gln Ala Thr Glu Val
        275                 280                 285

Lys Ser Val Pro Val Ala Gln Lys Ala Pro Thr Ala Thr Pro Val Ala
    290                 295                 300

Gln Pro Ala Ser Thr Thr Asn Ala Val Ala Ala His Pro Glu Asn Ala
305                 310                 315                 320

Gly Leu Gln Pro His Val Ala Ala Tyr Lys Glu Lys Val Ala Ser Thr
                325                 330                 335

Tyr Gly Val Asn Glu Phe Ser Thr Tyr Arg Ala Gly Asp Pro Gly Asp
            340                 345                 350

His Gly Lys Gly Leu Ala Val Asp Phe Ile Val Gly Thr Asn Gln Ala
        355                 360                 365
```

-continued

Leu Gly Asn Lys Val Ala Gln Tyr Ser Thr Gln Asn Met Ala Ala Asn
    370                 375                 380

Asn Ile Ser Tyr Val Ile Trp Gln Gln Lys Phe Tyr Ser Asn Thr Asn
385                 390                 395                 400

Ser Ile Tyr Gly Pro Ala Asn Thr Trp Asn Ala Met Pro Asp Arg Gly
                405                 410                 415

Gly Val Thr Ala Asn His Tyr Asp His Val His Val Ser Phe Asn Lys
            420                 425                 430

<210> SEQ ID NO 6
<211> LENGTH: 517
<212> TYPE: PRT
<213> ORGANISM: Streptococcus agalactiae

<400> SEQUENCE: 6

Ala Glu Val Ser Gln Glu Arg Pro Ala Lys Thr Thr Val Asn Ile Tyr
1               5                   10                  15

Lys Leu Gln Ala Asp Ser Tyr Lys Ser Glu Ile Thr Ser Asn Gly Gly
            20                  25                  30

Ile Glu Asn Lys Asp Gly Glu Val Ile Ser Asn Tyr Ala Lys Leu Gly
        35                  40                  45

Asp Asn Val Lys Gly Leu Gln Gly Val Gln Phe Lys Arg Tyr Lys Val
    50                  55                  60

Lys Thr Asp Ile Ser Val Asp Glu Leu Lys Lys Leu Thr Thr Val Glu
65                  70                  75                  80

Ala Ala Asp Ala Lys Val Gly Thr Ile Leu Glu Glu Gly Val Ser Leu
                85                  90                  95

Pro Gln Lys Thr Asn Ala Gln Gly Leu Val Val Asp Ala Leu Asp Ser
            100                 105                 110

Lys Ser Asn Val Arg Tyr Leu Tyr Val Glu Asp Leu Lys Asn Ser Pro
        115                 120                 125

Ser Asn Ile Thr Lys Ala Tyr Ala Val Pro Phe Val Leu Glu Leu Pro
    130                 135                 140

Val Ala Asn Ser Thr Gly Thr Gly Phe Leu Ser Glu Ile Asn Ile Tyr
145                 150                 155                 160

Pro Lys Asn Val Val Thr Asp Glu Pro Lys Thr Asp Lys Asp Val Lys
                165                 170                 175

Lys Leu Gly Gln Asp Asp Ala Gly Tyr Thr Ile Gly Glu Glu Phe Lys
            180                 185                 190

Trp Phe Leu Lys Ser Thr Ile Pro Ala Asn Leu Gly Asp Tyr Glu Lys
        195                 200                 205

Phe Glu Ile Thr Asp Lys Phe Ala Asp Gly Leu Thr Tyr Lys Ser Val
    210                 215                 220

Gly Lys Ile Lys Ile Gly Ser Lys Thr Leu Asn Arg Asp Glu His Tyr
225                 230                 235                 240

Thr Ile Asp Glu Pro Thr Val Asn Gln Asn Thr Leu Lys Ile Thr
                245                 250                 255

Phe Lys Pro Glu Lys Phe Lys Glu Ile Ala Glu Leu Leu Lys Gly Met
            260                 265                 270

Thr Leu Val Lys Asn Gln Asp Ala Leu Asp Lys Ala Thr Ala Asn Thr
        275                 280                 285

Asp Asp Ala Ala Phe Leu Glu Ile Pro Val Ala Ser Thr Ile Asn Glu
    290                 295                 300

Lys Ala Val Leu Gly Lys Ala Ile Glu Asn Thr Phe Glu Leu Gln Tyr

```
                    305                 310                 315                 320
Asp His Thr Pro Asp Lys Ala Asp Asn Pro Lys Pro Ser Asn Pro Pro
                325                 330                 335

Arg Lys Pro Glu Val His Thr Gly Gly Lys Arg Phe Val Lys Lys Asp
                340                 345                 350

Ser Thr Glu Thr Gln Thr Leu Gly Gly Ala Glu Phe Asp Leu Leu Ala
                355                 360                 365

Ser Asp Gly Thr Ala Val Lys Trp Thr Asp Ala Leu Ile Lys Ala Asn
            370                 375                 380

Thr Asn Lys Asn Tyr Ile Ala Gly Glu Ala Val Thr Gly Gln Pro Ile
385                 390                 395                 400

Lys Leu Lys Ser His Thr Asp Gly Thr Phe Glu Ile Lys Gly Leu Ala
                405                 410                 415

Tyr Ala Val Asp Ala Asn Ala Glu Gly Thr Ala Val Thr Tyr Lys Leu
                420                 425                 430

Lys Glu Thr Lys Ala Pro Glu Gly Tyr Val Ile Pro Asp Lys Glu Ile
                435                 440                 445

Glu Phe Thr Val Ser Gln Thr Ser Tyr Asn Thr Lys Pro Thr Asp Ile
                450                 455                 460

Thr Val Asp Ser Ala Asp Ala Thr Pro Asp Thr Ile Lys Asn Asn Lys
465                 470                 475                 480

Arg Pro Ser Ile Pro Asn Thr Gly Gly Ile Gly Thr Ala Ile Phe Val
                485                 490                 495

Ala Ile Gly Ala Ala Val Met Ala Phe Ala Val Lys Gly Met Lys Arg
                500                 505                 510

Arg Thr Lys Asp Asn
            515

<210> SEQ ID NO 7
<211> LENGTH: 525
<212> TYPE: PRT
<213> ORGANISM: Streptococcus agalactiae

<400> SEQUENCE: 7

Met Lys Leu Ser Lys Leu Leu Phe Ser Ala Ala Val Leu Thr Met
1               5                   10                  15

Val Ala Gly Ser Thr Val Glu Pro Val Ala Gln Phe Ala Thr Gly Met
                20                  25                  30

Ser Ile Val Arg Ala Ala Glu Val Ser Gln Glu Arg Pro Ala Lys Thr
            35                  40                  45

Thr Val Asn Ile Tyr Lys Leu Gln Ala Asp Ser Tyr Lys Ser Glu Ile
        50                  55                  60

Thr Ser Asn Gly Gly Ile Glu Asn Lys Asp Gly Glu Val Ile Ser Asn
65                  70                  75                  80

Tyr Ala Lys Leu Gly Asp Asn Val Lys Gly Leu Gln Gly Val Gln Phe
                85                  90                  95

Lys Arg Tyr Lys Val Lys Thr Asp Ile Ser Val Asp Glu Leu Lys Lys
                100                 105                 110

Leu Thr Thr Val Glu Ala Ala Asp Ala Lys Val Gly Thr Ile Leu Glu
            115                 120                 125

Glu Gly Val Ser Leu Pro Gln Lys Thr Asn Ala Gln Gly Leu Val Val
        130                 135                 140

Asp Ala Leu Asp Ser Lys Ser Asn Val Arg Tyr Leu Tyr Val Glu Asp
145                 150                 155                 160
```

Leu Lys Asn Ser Pro Ser Asn Ile Thr Lys Ala Tyr Ala Val Pro Phe
            165                 170                 175

Val Leu Glu Leu Pro Val Ala Asn Ser Thr Gly Thr Gly Phe Leu Ser
        180                 185                 190

Glu Ile Asn Ile Tyr Pro Lys Asn Val Val Thr Asp Glu Pro Lys Thr
            195                 200                 205

Asp Lys Asp Val Lys Lys Leu Gly Gln Asp Asp Ala Gly Tyr Thr Ile
        210                 215                 220

Gly Glu Glu Phe Lys Trp Phe Leu Lys Ser Thr Ile Pro Ala Asn Leu
225                 230                 235                 240

Gly Asp Tyr Glu Lys Phe Glu Ile Thr Asp Lys Phe Ala Asp Gly Leu
            245                 250                 255

Thr Tyr Lys Ser Val Gly Lys Ile Lys Ile Gly Ser Lys Thr Leu Asn
        260                 265                 270

Arg Asp Glu His Tyr Thr Ile Asp Glu Pro Thr Val Asp Asn Gln Asn
    275                 280                 285

Thr Leu Lys Ile Thr Phe Lys Pro Glu Lys Phe Lys Glu Ile Ala Glu
        290                 295                 300

Leu Leu Lys Gly Met Thr Leu Val Lys Asn Gln Asp Ala Leu Asp Lys
305                 310                 315                 320

Ala Thr Ala Asn Thr Asp Asp Ala Ala Phe Leu Glu Ile Pro Val Ala
            325                 330                 335

Ser Thr Ile Asn Glu Lys Ala Val Leu Gly Lys Ala Ile Glu Asn Thr
        340                 345                 350

Phe Glu Leu Gln Tyr Asp His Thr Pro Asp Lys Ala Asp Asn Pro Lys
    355                 360                 365

Pro Ser Asn Pro Pro Arg Lys Pro Glu Val His Thr Gly Gly Lys Arg
        370                 375                 380

Phe Val Lys Lys Asp Ser Thr Glu Thr Gln Thr Leu Gly Gly Ala Glu
385                 390                 395                 400

Phe Asp Leu Leu Ala Ser Asp Gly Thr Ala Val Lys Trp Thr Asp Ala
            405                 410                 415

Leu Ile Lys Ala Asn Thr Asn Lys Asn Tyr Ile Ala Gly Glu Ala Val
        420                 425                 430

Thr Gly Gln Pro Ile Lys Leu Lys Ser His Thr Asp Gly Thr Phe Glu
    435                 440                 445

Ile Lys Gly Leu Ala Tyr Ala Val Asp Ala Asn Ala Glu Gly Thr Ala
        450                 455                 460

Val Thr Tyr Lys Leu Lys Glu Thr Lys Ala Pro Glu Gly Tyr Val Ile
465                 470                 475                 480

Pro Asp Lys Glu Ile Glu Phe Thr Val Ser Gln Thr Ser Tyr Asn Thr
            485                 490                 495

Lys Pro Thr Asp Ile Thr Val Asp Ser Ala Asp Ala Thr Pro Asp Thr
        500                 505                 510

Ile Lys Asn Asn Lys Arg Pro Ser Ile Pro Asn Thr Gly
        515                 520                 525

<210> SEQ ID NO 8
<211> LENGTH: 520
<212> TYPE: PRT
<213> ORGANISM: Streptococcus agalactiae

<400> SEQUENCE: 8

Met Lys Leu Ser Lys Lys Leu Leu Phe Ser Ala Ala Val Leu Thr Met
1               5                   10                  15

```
Val Ala Gly Ser Thr Val Glu Pro Val Ala Gln Phe Ala Thr Gly Met
         20                  25                  30

Ser Ile Val Arg Ala Ala Glu Val Ser Gln Glu Arg Pro Ala Lys Thr
             35                  40                  45

Thr Val Asn Ile Tyr Lys Leu Gln Ala Asp Ser Tyr Lys Ser Glu Ile
 50                  55                  60

Thr Ser Asn Gly Gly Ile Glu Asn Lys Asp Gly Glu Val Ile Ser Asn
 65                  70                  75                  80

Tyr Ala Lys Leu Gly Asp Asn Val Lys Gly Leu Gln Gly Val Gln Phe
                 85                  90                  95

Lys Arg Tyr Lys Val Lys Thr Asp Ile Ser Val Asp Glu Leu Lys Lys
                100                 105                 110

Leu Thr Thr Val Glu Ala Ala Asp Ala Lys Val Gly Thr Ile Leu Glu
             115                 120                 125

Glu Gly Val Ser Leu Pro Gln Lys Thr Asn Ala Gln Gly Leu Val Val
     130                 135                 140

Asp Ala Leu Asp Ser Lys Ser Asn Val Arg Tyr Leu Tyr Val Glu Asp
145                 150                 155                 160

Leu Lys Asn Ser Pro Ser Asn Ile Thr Lys Ala Tyr Ala Val Pro Phe
                165                 170                 175

Val Leu Glu Leu Pro Val Ala Asn Ser Thr Gly Thr Gly Phe Leu Ser
             180                 185                 190

Glu Ile Asn Ile Tyr Pro Lys Asn Val Val Thr Asp Glu Pro Lys Thr
         195                 200                 205

Asp Lys Asp Val Lys Lys Leu Gly Gln Asp Asp Ala Gly Tyr Thr Ile
210                 215                 220

Gly Glu Glu Phe Lys Trp Phe Leu Lys Ser Thr Ile Pro Ala Asn Leu
225                 230                 235                 240

Gly Asp Tyr Glu Lys Phe Glu Ile Thr Asp Lys Phe Ala Asp Gly Leu
                245                 250                 255

Thr Tyr Lys Ser Val Gly Lys Ile Lys Ile Gly Ser Lys Thr Leu Asn
             260                 265                 270

Arg Asp Glu His Tyr Thr Ile Asp Glu Pro Thr Val Asp Asn Gln Asn
         275                 280                 285

Thr Leu Lys Ile Thr Phe Lys Pro Glu Lys Phe Lys Glu Ile Ala Glu
 290                 295                 300

Leu Leu Lys Gly Met Thr Leu Val Lys Asn Gln Asp Ala Leu Asp Lys
305                 310                 315                 320

Ala Thr Ala Asn Thr Asp Asp Ala Ala Phe Leu Glu Ile Pro Val Ala
                325                 330                 335

Ser Thr Ile Asn Glu Lys Ala Val Leu Gly Lys Ala Ile Glu Asn Thr
             340                 345                 350

Phe Glu Leu Gln Tyr Asp His Thr Pro Asp Lys Ala Asp Asn Pro Lys
         355                 360                 365

Pro Ser Asn Pro Pro Arg Lys Pro Glu Val His Thr Gly Gly Lys Arg
370                 375                 380

Phe Val Lys Lys Asp Ser Thr Glu Thr Gln Thr Leu Gly Gly Ala Glu
385                 390                 395                 400

Phe Asp Leu Leu Ala Ser Asp Gly Thr Ala Val Lys Trp Thr Asp Ala
                405                 410                 415

Leu Ile Lys Ala Asn Thr Asn Lys Asn Tyr Ile Ala Gly Glu Ala Val
             420                 425                 430
```

```
Thr Gly Gln Pro Ile Lys Leu Lys Ser His Thr Asp Gly Thr Phe Glu
            435                 440                 445

Ile Lys Gly Leu Ala Tyr Ala Val Asp Ala Asn Ala Glu Gly Thr Ala
450                 455                 460

Val Thr Tyr Lys Leu Lys Glu Thr Lys Ala Pro Glu Gly Tyr Val Ile
465                 470                 475                 480

Pro Asp Lys Glu Ile Glu Phe Thr Val Ser Gln Thr Ser Tyr Asn Thr
                    485                 490                 495

Lys Pro Thr Asp Ile Thr Val Asp Ser Ala Asp Ala Thr Pro Asp Thr
                500                 505                 510

Ile Lys Asn Asn Lys Arg Pro Ser
            515                 520

<210> SEQ ID NO 9
<211> LENGTH: 483
<212> TYPE: PRT
<213> ORGANISM: Streptococcus agalactiae

<400> SEQUENCE: 9

Ala Glu Val Ser Gln Glu Arg Pro Ala Lys Thr Thr Val Asn Ile Tyr
1               5                   10                  15

Lys Leu Gln Ala Asp Ser Tyr Lys Ser Glu Ile Thr Ser Asn Gly Gly
            20                  25                  30

Ile Glu Asn Lys Asp Gly Glu Val Ile Ser Asn Tyr Ala Lys Leu Gly
        35                  40                  45

Asp Asn Val Lys Gly Leu Gln Gly Val Gln Phe Lys Arg Tyr Lys Val
    50                  55                  60

Lys Thr Asp Ile Ser Val Asp Glu Leu Lys Lys Leu Thr Thr Val Glu
65                  70                  75                  80

Ala Ala Asp Ala Lys Val Gly Thr Ile Leu Glu Glu Gly Val Ser Leu
                85                  90                  95

Pro Gln Lys Thr Asn Ala Gln Gly Leu Val Val Asp Ala Leu Asp Ser
            100                 105                 110

Lys Ser Asn Val Arg Tyr Leu Tyr Val Glu Asp Leu Lys Asn Ser Pro
        115                 120                 125

Ser Asn Ile Thr Lys Ala Tyr Ala Val Pro Phe Val Leu Glu Leu Pro
    130                 135                 140

Val Ala Asn Ser Thr Gly Thr Gly Phe Leu Ser Glu Ile Asn Ile Tyr
145                 150                 155                 160

Pro Lys Asn Val Val Thr Asp Glu Pro Lys Thr Asp Lys Asp Val Lys
                165                 170                 175

Lys Leu Gly Gln Asp Asp Ala Gly Tyr Thr Ile Gly Glu Glu Phe Lys
            180                 185                 190

Trp Phe Leu Lys Ser Thr Ile Pro Ala Asn Leu Gly Asp Tyr Glu Lys
        195                 200                 205

Phe Glu Ile Thr Asp Lys Phe Ala Asp Gly Leu Thr Tyr Lys Ser Val
    210                 215                 220

Gly Lys Ile Lys Ile Gly Ser Lys Thr Leu Asn Arg Asp Glu His Tyr
225                 230                 235                 240

Thr Ile Asp Glu Pro Thr Val Asp Asn Gln Asn Thr Leu Lys Ile Thr
                245                 250                 255

Phe Lys Pro Glu Lys Phe Lys Glu Ile Ala Glu Leu Leu Lys Gly Met
            260                 265                 270

Thr Leu Val Lys Asn Gln Asp Ala Leu Asp Lys Ala Thr Ala Asn Thr
        275                 280                 285
```

Asp Asp Ala Ala Phe Leu Glu Ile Pro Val Ala Ser Thr Ile Asn Glu
            290                 295                 300

Lys Ala Val Leu Gly Lys Ala Ile Glu Asn Thr Phe Glu Leu Gln Tyr
305                 310                 315                 320

Asp His Thr Pro Asp Lys Ala Asp Asn Pro Lys Pro Ser Asn Pro Pro
                325                 330                 335

Arg Lys Pro Glu Val His Thr Gly Gly Lys Arg Phe Val Lys Lys Asp
            340                 345                 350

Ser Thr Glu Thr Gln Thr Leu Gly Gly Ala Glu Phe Asp Leu Leu Ala
            355                 360                 365

Ser Asp Gly Thr Ala Val Lys Trp Thr Asp Ala Leu Ile Lys Ala Asn
370                 375                 380

Thr Asn Lys Asn Tyr Ile Ala Gly Glu Ala Val Thr Gly Gln Pro Ile
385                 390                 395                 400

Lys Leu Lys Ser His Thr Asp Gly Thr Phe Glu Ile Lys Gly Leu Ala
                405                 410                 415

Tyr Ala Val Asp Ala Asn Ala Glu Gly Thr Ala Val Thr Tyr Lys Leu
                420                 425                 430

Lys Glu Thr Lys Ala Pro Glu Gly Tyr Val Ile Pro Asp Lys Glu Ile
            435                 440                 445

Glu Phe Thr Val Ser Gln Thr Ser Tyr Asn Thr Lys Pro Thr Asp Ile
450                 455                 460

Thr Val Asp Ser Ala Asp Ala Thr Pro Asp Thr Ile Lys Asn Asn Lys
465                 470                 475                 480

Arg Pro Ser

<210> SEQ ID NO 10
<211> LENGTH: 271
<212> TYPE: PRT
<213> ORGANISM: Streptococcus agalactiae

<400> SEQUENCE: 10

Ala Glu Val Ser Gln Glu Arg Pro Ala Lys Thr Thr Val Asn Ile Tyr
1               5                   10                  15

Lys Leu Gln Ala Asp Ser Tyr Lys Ser Glu Ile Thr Ser Asn Gly Gly
            20                  25                  30

Ile Glu Asn Lys Asp Gly Glu Val Ile Ser Asn Tyr Ala Lys Leu Gly
        35                  40                  45

Asp Asn Val Lys Gly Leu Gln Gly Val Gln Phe Lys Arg Tyr Lys Val
    50                  55                  60

Lys Thr Asp Ile Ser Val Asp Glu Leu Lys Lys Leu Thr Thr Val Glu
65                  70                  75                  80

Ala Ala Asp Ala Lys Val Gly Thr Ile Leu Glu Glu Gly Val Ser Leu
                85                  90                  95

Pro Gln Lys Thr Asn Ala Gln Gly Leu Val Val Asp Ala Leu Asp Ser
            100                 105                 110

Lys Ser Asn Val Arg Tyr Leu Tyr Val Glu Asp Leu Lys Asn Ser Pro
        115                 120                 125

Ser Asn Ile Thr Lys Ala Tyr Ala Val Pro Phe Val Leu Glu Leu Pro
    130                 135                 140

Val Ala Asn Ser Thr Gly Thr Gly Phe Leu Ser Glu Ile Asn Ile Tyr
145                 150                 155                 160

Pro Lys Asn Val Val Thr Asp Glu Pro Lys Thr Asp Lys Asp Val Lys
                165                 170                 175

```
Lys Leu Gly Gln Asp Asp Ala Gly Tyr Thr Ile Gly Glu Glu Phe Lys
            180                 185                 190

Trp Phe Leu Lys Ser Thr Ile Pro Ala Asn Leu Gly Asp Tyr Glu Lys
            195                 200                 205

Phe Glu Ile Thr Asp Lys Phe Ala Asp Gly Leu Thr Tyr Lys Ser Val
            210                 215                 220

Gly Lys Ile Lys Ile Gly Ser Lys Thr Leu Asn Arg Asp Glu His Tyr
225                 230                 235                 240

Thr Ile Asp Glu Pro Thr Val Asp Asn Gln Asn Thr Leu Lys Ile Thr
                245                 250                 255

Phe Lys Pro Glu Lys Phe Lys Glu Ile Ala Glu Leu Leu Lys Gly
            260                 265                 270

<210> SEQ ID NO 11
<211> LENGTH: 862
<212> TYPE: PRT
<213> ORGANISM: Streptococcus agalactiae

<400> SEQUENCE: 11

Gly Glu Thr Gln Asp Thr Asn Gln Ala Leu Gly Lys Val Ile Val Lys
1               5                   10                  15

Lys Thr Gly Asp Asn Ala Thr Pro Leu Gly Lys Ala Thr Phe Val Leu
            20                  25                  30

Lys Asn Asp Asn Asp Lys Ser Glu Thr Ser His Glu Thr Val Glu Gly
            35                  40                  45

Ser Gly Glu Ala Thr Phe Glu Asn Ile Lys Pro Gly Asp Tyr Thr Leu
    50                  55                  60

Arg Glu Glu Thr Ala Pro Ile Gly Tyr Lys Lys Thr Asp Lys Thr Trp
65                  70                  75                  80

Lys Val Lys Val Ala Asp Asn Gly Ala Thr Ile Ile Glu Gly Met Asp
                85                  90                  95

Ala Asp Lys Ala Glu Lys Arg Lys Glu Val Leu Asn Ala Gln Tyr Pro
            100                 105                 110

Lys Ser Ala Ile Tyr Glu Asp Thr Lys Glu Asn Tyr Pro Leu Val Asn
            115                 120                 125

Val Glu Gly Ser Lys Val Gly Glu Gln Tyr Lys Ala Leu Asn Pro Ile
            130                 135                 140

Asn Gly Lys Asp Gly Arg Arg Glu Ile Ala Glu Gly Trp Leu Ser Lys
145                 150                 155                 160

Lys Ile Thr Gly Val Asn Asp Leu Asp Lys Asn Lys Tyr Lys Ile Glu
                165                 170                 175

Leu Thr Val Glu Gly Lys Thr Thr Val Glu Thr Lys Glu Leu Asn Gln
            180                 185                 190

Pro Leu Asp Val Val Leu Leu Asp Asn Ser Asn Ser Met Asn Asn
            195                 200                 205

Glu Arg Ala Asn Asn Ser Gln Arg Ala Leu Lys Ala Gly Glu Ala Val
            210                 215                 220

Glu Lys Leu Ile Asp Lys Ile Thr Ser Asn Lys Asp Asn Arg Val Ala
225                 230                 235                 240

Leu Val Thr Tyr Ala Ser Thr Ile Phe Asp Gly Thr Glu Ala Thr Val
                245                 250                 255

Ser Lys Gly Val Ala Asp Gln Asn Gly Lys Ala Leu Asn Asp Ser Val
            260                 265                 270

Ser Trp Asp Tyr His Lys Thr Thr Phe Thr Ala Thr Thr His Asn Tyr
```

```
            275                 280                 285
Ser Tyr Leu Asn Leu Thr Asn Asp Ala Asn Glu Val Asn Ile Leu Lys
290                 295                 300

Ser Arg Ile Pro Lys Glu Ala Glu His Ile Asn Gly Asp Arg Thr Leu
305                 310                 315                 320

Tyr Gln Phe Gly Ala Thr Phe Thr Gln Lys Ala Leu Met Lys Ala Asn
                325                 330                 335

Glu Ile Leu Glu Thr Gln Ser Ser Asn Ala Arg Lys Lys Leu Ile Phe
            340                 345                 350

His Val Thr Asp Gly Val Pro Thr Met Ser Tyr Ala Ile Asn Phe Asn
        355                 360                 365

Pro Tyr Ile Ser Thr Ser Tyr Gln Asn Gln Phe Asn Ser Phe Leu Asn
    370                 375                 380

Lys Ile Pro Asp Arg Ser Gly Ile Leu Gln Glu Asp Phe Ile Ile Asn
385                 390                 395                 400

Gly Asp Asp Tyr Gln Ile Val Lys Gly Asp Gly Glu Ser Phe Lys Leu
                405                 410                 415

Phe Ser Asp Arg Lys Val Pro Val Thr Gly Gly Thr Thr Gln Ala Ala
            420                 425                 430

Tyr Arg Val Pro Gln Asn Gln Leu Ser Val Met Ser Asn Glu Gly Tyr
        435                 440                 445

Ala Ile Asn Ser Gly Tyr Ile Tyr Leu Tyr Trp Arg Asp Tyr Asn Trp
    450                 455                 460

Val Tyr Pro Phe Asp Pro Lys Thr Lys Lys Val Ser Ala Thr Lys Gln
465                 470                 475                 480

Ile Lys Thr His Gly Glu Pro Thr Thr Leu Tyr Phe Asn Gly Asn Ile
                485                 490                 495

Arg Pro Lys Gly Tyr Asp Ile Phe Thr Val Gly Ile Gly Val Asn Gly
            500                 505                 510

Asp Pro Gly Ala Thr Pro Leu Glu Ala Glu Lys Phe Met Gln Ser Ile
        515                 520                 525

Ser Ser Lys Thr Glu Asn Tyr Thr Asn Val Asp Asp Thr Asn Lys Ile
    530                 535                 540

Tyr Asp Glu Leu Asn Lys Tyr Phe Lys Thr Ile Val Glu Glu Lys His
545                 550                 555                 560

Ser Ile Val Asp Gly Asn Val Thr Asp Pro Met Gly Glu Met Ile Glu
                565                 570                 575

Phe Gln Leu Lys Asn Gly Gln Ser Phe Thr His Asp Asp Tyr Val Leu
            580                 585                 590

Val Gly Asn Asp Gly Ser Gln Leu Lys Asn Gly Val Ala Leu Gly Gly
        595                 600                 605

Pro Asn Ser Asp Gly Gly Ile Leu Lys Asp Val Thr Val Thr Tyr Asp
    610                 615                 620

Lys Thr Ser Gln Thr Ile Lys Ile Asn His Leu Asn Leu Gly Ser Gly
625                 630                 635                 640

Gln Lys Val Val Leu Thr Tyr Asp Val Arg Leu Lys Asp Asn Tyr Ile
                645                 650                 655

Ser Asn Lys Phe Tyr Asn Thr Asn Asn Arg Thr Thr Leu Ser Pro Lys
            660                 665                 670

Ser Glu Lys Glu Pro Asn Thr Ile Arg Asp Phe Pro Ile Pro Lys Ile
        675                 680                 685

Arg Asp Val Arg Glu Phe Pro Val Leu Thr Ile Ser Asn Gln Lys Lys
    690                 695                 700
```

Met Gly Glu Val Glu Phe Ile Lys Val Asn Lys Asp Lys His Ser Glu
705                 710                 715                 720

Ser Leu Leu Gly Ala Lys Phe Gln Leu Gln Ile Glu Lys Asp Phe Ser
                725                 730                 735

Gly Tyr Lys Gln Phe Val Pro Glu Gly Ser Asp Val Thr Thr Lys Asn
            740                 745                 750

Asp Gly Lys Ile Tyr Phe Lys Ala Leu Gln Asp Gly Asn Tyr Lys Leu
        755                 760                 765

Tyr Glu Ile Ser Ser Pro Asp Gly Tyr Ile Glu Val Lys Thr Lys Pro
770                 775                 780

Val Val Thr Phe Thr Ile Gln Asn Gly Glu Val Thr Asn Leu Lys Ala
785                 790                 795                 800

Asp Pro Asn Ala Asn Lys Asn Gln Ile Gly Tyr Leu Glu Gly Asn Gly
                805                 810                 815

Lys His Leu Ile Thr Asn Thr Pro Lys Arg Pro Pro Gly Val Phe Pro
            820                 825                 830

Lys Thr Gly Gly Ile Gly Thr Ile Val Tyr Ile Leu Val Gly Ser Thr
        835                 840                 845

Phe Met Ile Leu Thr Ile Cys Ser Phe Arg Arg Lys Gln Leu
    850                 855                 860

<210> SEQ ID NO 12
<211> LENGTH: 851
<212> TYPE: PRT
<213> ORGANISM: Streptococcus agalactiae

<400> SEQUENCE: 12

Met Lys Lys Arg Gln Lys Ile Trp Arg Gly Leu Ser Val Thr Leu Leu
1               5                   10                  15

Ile Leu Ser Gln Ile Pro Phe Gly Ile Leu Val Gln Gly Glu Thr Gln
                20                  25                  30

Asp Thr Asn Gln Ala Leu Gly Lys Val Ile Val Lys Lys Thr Gly Asp
            35                  40                  45

Asn Ala Thr Pro Leu Gly Lys Ala Thr Phe Val Leu Lys Asn Asp Asn
50                  55                  60

Asp Lys Ser Glu Thr Ser His Glu Thr Val Glu Gly Ser Gly Glu Ala
65                  70                  75                  80

Thr Phe Glu Asn Ile Lys Pro Gly Asp Tyr Thr Leu Arg Glu Glu Thr
                85                  90                  95

Ala Pro Ile Gly Tyr Lys Lys Thr Asp Lys Thr Trp Lys Val Lys Val
            100                 105                 110

Ala Asp Asn Gly Ala Thr Ile Ile Glu Gly Met Asp Ala Asp Lys Ala
        115                 120                 125

Glu Lys Arg Lys Glu Val Leu Asn Ala Gln Tyr Pro Lys Ser Ala Ile
130                 135                 140

Tyr Glu Asp Thr Lys Glu Asn Tyr Pro Leu Val Asn Val Glu Gly Ser
145                 150                 155                 160

Lys Val Gly Glu Gln Tyr Lys Ala Leu Asn Pro Ile Asn Gly Lys Asp
                165                 170                 175

Gly Arg Arg Glu Ile Ala Glu Gly Trp Leu Ser Lys Lys Ile Thr Gly
            180                 185                 190

Val Asn Asp Leu Asp Lys Asn Lys Tyr Lys Ile Glu Leu Thr Val Glu
        195                 200                 205

Gly Lys Thr Thr Val Glu Thr Lys Glu Leu Asn Gln Pro Leu Asp Val

```
                 210                 215                 220
Val Val Leu Leu Asp Asn Ser Asn Ser Met Asn Asn Glu Arg Ala Asn
225                 230                 235                 240

Asn Ser Gln Arg Ala Leu Lys Ala Gly Glu Ala Val Glu Lys Leu Ile
                245                 250                 255

Asp Lys Ile Thr Ser Asn Lys Asp Asn Arg Val Ala Leu Val Thr Tyr
                260                 265                 270

Ala Ser Thr Ile Phe Asp Gly Thr Glu Ala Thr Val Ser Lys Gly Val
                275                 280                 285

Ala Asp Gln Asn Gly Lys Ala Leu Asn Asp Ser Val Ser Trp Asp Tyr
                290                 295                 300

His Lys Thr Thr Phe Thr Ala Thr Thr His Asn Tyr Ser Tyr Leu Asn
305                 310                 315                 320

Leu Thr Asn Asp Ala Asn Glu Val Asn Ile Leu Lys Ser Arg Ile Pro
                325                 330                 335

Lys Glu Ala Glu His Ile Asn Gly Asp Arg Thr Leu Tyr Gln Phe Gly
                340                 345                 350

Ala Thr Phe Thr Gln Lys Ala Leu Met Lys Ala Asn Glu Ile Leu Glu
                355                 360                 365

Thr Gln Ser Ser Asn Ala Arg Lys Lys Leu Ile Phe His Val Thr Asp
                370                 375                 380

Gly Val Pro Thr Met Ser Tyr Ala Ile Asn Phe Asn Pro Tyr Ile Ser
385                 390                 395                 400

Thr Ser Tyr Gln Asn Gln Phe Asn Ser Phe Leu Asn Lys Ile Pro Asp
                405                 410                 415

Arg Ser Gly Ile Leu Gln Glu Asp Phe Ile Ile Asn Gly Asp Asp Tyr
                420                 425                 430

Gln Ile Val Lys Gly Asp Gly Glu Ser Phe Lys Leu Phe Ser Asp Arg
                435                 440                 445

Lys Val Pro Val Thr Gly Gly Thr Thr Gln Ala Ala Tyr Arg Val Pro
450                 455                 460

Gln Asn Gln Leu Ser Val Met Ser Asn Glu Gly Tyr Ala Ile Asn Ser
465                 470                 475                 480

Gly Tyr Ile Tyr Leu Tyr Trp Arg Asp Tyr Asn Trp Val Tyr Pro Phe
                485                 490                 495

Asp Pro Lys Thr Lys Lys Val Ser Ala Thr Lys Gln Ile Lys Thr His
                500                 505                 510

Gly Glu Pro Thr Thr Leu Tyr Phe Asn Gly Asn Ile Arg Pro Lys Gly
                515                 520                 525

Tyr Asp Ile Phe Thr Val Gly Ile Gly Val Asn Gly Asp Pro Gly Ala
                530                 535                 540

Thr Pro Leu Glu Ala Glu Lys Phe Met Gln Ser Ile Ser Ser Lys Thr
545                 550                 555                 560

Glu Asn Tyr Thr Asn Val Asp Asp Thr Asn Lys Ile Tyr Asp Glu Leu
                565                 570                 575

Asn Lys Tyr Phe Lys Thr Ile Val Glu Glu Lys His Ser Ile Val Asp
                580                 585                 590

Gly Asn Val Thr Asp Pro Met Gly Glu Met Ile Glu Phe Gln Leu Lys
                595                 600                 605

Asn Gly Gln Ser Phe Thr His Asp Asp Tyr Val Leu Val Gly Asn Asp
                610                 615                 620

Gly Ser Gln Leu Lys Asn Gly Val Ala Leu Gly Gly Pro Asn Ser Asp
625                 630                 635                 640
```

```
Gly Gly Ile Leu Lys Asp Val Thr Val Thr Tyr Asp Lys Thr Ser Gln
            645                 650                 655

Thr Ile Lys Ile Asn His Leu Asn Leu Gly Ser Gly Gln Lys Val Val
            660                 665                 670

Leu Thr Tyr Asp Val Arg Leu Lys Asp Asn Tyr Ile Ser Asn Lys Phe
            675                 680                 685

Tyr Asn Thr Asn Asn Arg Thr Thr Leu Ser Pro Lys Ser Glu Lys Glu
            690                 695                 700

Pro Asn Thr Ile Arg Asp Phe Pro Ile Pro Lys Ile Arg Asp Val Arg
705                 710                 715                 720

Glu Phe Pro Val Leu Thr Ile Ser Asn Gln Lys Lys Met Gly Glu Val
            725                 730                 735

Glu Phe Ile Lys Val Asn Lys Asp Lys His Ser Glu Ser Leu Leu Gly
            740                 745                 750

Ala Lys Phe Gln Leu Gln Ile Glu Lys Asp Phe Ser Gly Tyr Lys Gln
            755                 760                 765

Phe Val Pro Glu Gly Ser Asp Val Thr Thr Lys Asn Asp Gly Lys Ile
            770                 775                 780

Tyr Phe Lys Ala Leu Gln Asp Gly Asn Tyr Lys Leu Tyr Glu Ile Ser
785                 790                 795                 800

Ser Pro Asp Gly Tyr Ile Glu Val Lys Thr Lys Pro Val Val Thr Phe
            805                 810                 815

Thr Ile Gln Asn Gly Glu Val Thr Asn Leu Lys Ala Asp Pro Asn Ala
            820                 825                 830

Asn Lys Asn Gln Ile Gly Tyr Leu Glu Gly Asn Gly Lys His Leu Ile
            835                 840                 845

Thr Asn Thr
    850

<210> SEQ ID NO 13
<211> LENGTH: 823
<212> TYPE: PRT
<213> ORGANISM: Streptococcus agalactiae

<400> SEQUENCE: 13

Gly Glu Thr Gln Asp Thr Asn Gln Ala Leu Gly Lys Val Ile Val Lys
1               5                   10                  15

Lys Thr Gly Asp Asn Ala Thr Pro Leu Gly Lys Ala Thr Phe Val Leu
            20                  25                  30

Lys Asn Asp Asn Asp Lys Ser Glu Thr Ser His Glu Thr Val Glu Gly
            35                  40                  45

Ser Gly Glu Ala Thr Phe Glu Asn Ile Lys Pro Gly Asp Tyr Thr Leu
        50                  55                  60

Arg Glu Glu Thr Ala Pro Ile Gly Tyr Lys Lys Thr Asp Lys Thr Trp
65                  70                  75                  80

Lys Val Lys Val Ala Asp Asn Gly Ala Thr Ile Ile Glu Gly Met Asp
            85                  90                  95

Ala Asp Lys Ala Glu Lys Arg Lys Glu Val Leu Asn Ala Gln Tyr Pro
            100                 105                 110

Lys Ser Ala Ile Tyr Glu Asp Thr Lys Glu Asn Tyr Pro Leu Val Asn
            115                 120                 125

Val Glu Gly Ser Lys Val Gly Glu Gln Tyr Lys Ala Leu Asn Pro Ile
            130                 135                 140

Asn Gly Lys Asp Gly Arg Arg Glu Ile Ala Glu Gly Trp Leu Ser Lys
```

-continued

```
145                 150                 155                 160
Lys Ile Thr Gly Val Asn Asp Leu Asp Lys Asn Lys Tyr Lys Ile Glu
                165                 170                 175
Leu Thr Val Glu Gly Lys Thr Val Glu Thr Lys Glu Leu Asn Gln
            180                 185                 190
Pro Leu Asp Val Val Leu Leu Asp Asn Ser Asn Ser Met Asn Asn
        195                 200                 205
Glu Arg Ala Asn Asn Ser Gln Arg Ala Leu Lys Ala Gly Glu Ala Val
    210                 215                 220
Glu Lys Leu Ile Asp Lys Ile Thr Ser Asn Lys Asp Asn Arg Val Ala
225                 230                 235                 240
Leu Val Thr Tyr Ala Ser Thr Ile Phe Asp Gly Thr Glu Ala Thr Val
                245                 250                 255
Ser Lys Gly Val Ala Asp Gln Asn Gly Lys Ala Leu Asn Asp Ser Val
            260                 265                 270
Ser Trp Asp Tyr His Lys Thr Thr Phe Thr Ala Thr His Asn Tyr
        275                 280                 285
Ser Tyr Leu Asn Leu Thr Asn Asp Ala Asn Glu Val Asn Ile Leu Lys
    290                 295                 300
Ser Arg Ile Pro Lys Glu Ala Glu His Ile Asn Gly Asp Arg Thr Leu
305                 310                 315                 320
Tyr Gln Phe Gly Ala Thr Phe Thr Gln Lys Ala Leu Met Lys Ala Asn
                325                 330                 335
Glu Ile Leu Glu Thr Gln Ser Ser Asn Ala Arg Lys Lys Leu Ile Phe
            340                 345                 350
His Val Thr Asp Gly Val Pro Thr Met Ser Tyr Ala Ile Asn Phe Asn
        355                 360                 365
Pro Tyr Ile Ser Thr Ser Tyr Gln Asn Gln Phe Asn Ser Phe Leu Asn
    370                 375                 380
Lys Ile Pro Asp Arg Ser Gly Ile Leu Gln Glu Asp Phe Ile Ile Asn
385                 390                 395                 400
Gly Asp Asp Tyr Gln Ile Val Lys Gly Asp Gly Glu Ser Phe Lys Leu
                405                 410                 415
Phe Ser Asp Arg Lys Val Pro Val Thr Gly Thr Thr Gln Ala Ala
            420                 425                 430
Tyr Arg Val Pro Gln Asn Gln Leu Ser Val Met Ser Asn Glu Gly Tyr
        435                 440                 445
Ala Ile Asn Ser Gly Tyr Ile Tyr Leu Tyr Trp Arg Asp Tyr Asn Trp
    450                 455                 460
Val Tyr Pro Phe Asp Pro Lys Thr Lys Lys Val Ser Ala Thr Lys Gln
465                 470                 475                 480
Ile Lys Thr His Gly Glu Pro Thr Thr Leu Tyr Phe Asn Gly Asn Ile
                485                 490                 495
Arg Pro Lys Gly Tyr Asp Ile Phe Thr Val Gly Ile Gly Val Asn Gly
            500                 505                 510
Asp Pro Gly Ala Thr Pro Leu Glu Ala Glu Lys Phe Met Gln Ser Ile
        515                 520                 525
Ser Ser Lys Thr Glu Asn Tyr Thr Asn Val Asp Thr Asn Lys Ile
    530                 535                 540
Tyr Asp Glu Leu Asn Lys Tyr Phe Lys Thr Ile Val Glu Glu Lys His
545                 550                 555                 560
Ser Ile Val Asp Gly Asn Val Thr Asp Pro Met Gly Glu Met Ile Glu
                565                 570                 575
```

```
Phe Gln Leu Lys Asn Gly Gln Ser Phe Thr His Asp Tyr Val Leu
            580                 585                 590
Val Gly Asn Asp Gly Ser Gln Leu Lys Asn Gly Val Ala Leu Gly Gly
        595                 600                 605
Pro Asn Ser Asp Gly Gly Ile Leu Lys Asp Val Thr Val Thr Tyr Asp
610                 615                 620
Lys Thr Ser Gln Thr Ile Lys Ile Asn His Leu Asn Leu Gly Ser Gly
625                 630                 635                 640
Gln Lys Val Val Leu Thr Tyr Asp Val Arg Leu Lys Asp Asn Tyr Ile
                645                 650                 655
Ser Asn Lys Phe Tyr Asn Thr Asn Arg Thr Thr Leu Ser Pro Lys
            660                 665                 670
Ser Glu Lys Glu Pro Asn Thr Ile Arg Asp Phe Pro Ile Pro Lys Ile
        675                 680                 685
Arg Asp Val Arg Glu Phe Pro Val Leu Thr Ile Ser Asn Gln Lys Lys
    690                 695                 700
Met Gly Glu Val Glu Phe Ile Lys Val Asn Lys Asp Lys His Ser Glu
705                 710                 715                 720
Ser Leu Leu Gly Ala Lys Phe Gln Leu Gln Ile Glu Lys Asp Phe Ser
                725                 730                 735
Gly Tyr Lys Gln Phe Val Pro Glu Gly Ser Asp Val Thr Thr Lys Asn
            740                 745                 750
Asp Gly Lys Ile Tyr Phe Lys Ala Leu Gln Asp Gly Asn Tyr Lys Leu
        755                 760                 765
Tyr Glu Ile Ser Ser Pro Asp Gly Tyr Ile Glu Val Lys Thr Lys Pro
    770                 775                 780
Val Val Thr Phe Thr Ile Gln Asn Gly Glu Val Thr Asn Leu Lys Ala
785                 790                 795                 800
Asp Pro Asn Ala Asn Lys Asn Gln Ile Gly Tyr Leu Glu Gly Asn Gly
                805                 810                 815
Lys His Leu Ile Thr Asn Thr
            820

<210> SEQ ID NO 14
<211> LENGTH: 1109
<212> TYPE: PRT
<213> ORGANISM: Streptococcus agalactiae

<400> SEQUENCE: 14

Gln Ser Asp Ile Lys Ala Asn Thr Val Thr Glu Asp Thr Pro Ala Thr
1               5                   10                  15
Glu Gln Ala Val Glu Pro Pro Gln Pro Ile Ala Val Ser Glu Glu Ser
            20                  25                  30
Arg Ser Ser Lys Glu Thr Lys Thr Ser Gln Thr Pro Ser Asp Val Gly
        35                  40                  45
Glu Thr Val Ala Asp Asp Ala Asn Asp Leu Ala Pro Gln Ala Pro Ala
    50                  55                  60
Lys Thr Ala Asp Thr Pro Ala Thr Ser Lys Ala Thr Ile Arg Asp Leu
65                  70                  75                  80
Asn Asp Pro Ser His Val Lys Thr Leu Gln Glu Lys Ala Gly Lys Gly
                85                  90                  95
Ala Gly Thr Val Val Ala Val Ile Asp Ala Gly Phe Asp Lys Asn His
            100                 105                 110
Glu Ala Trp Arg Leu Thr Asp Lys Thr Lys Ala Arg Tyr Gln Ser Lys
```

-continued

```
            115                 120                 125
Glu Asn Leu Glu Lys Ala Lys Lys Glu His Gly Ile Thr Tyr Gly Glu
        130                 135                 140

Trp Val Asn Asp Lys Val Ala Tyr Tyr His Asp Tyr Ser Lys Asp Gly
145                 150                 155                 160

Lys Asn Ala Val Asp Gln Glu His Gly Thr His Val Ser Gly Ile Leu
                165                 170                 175

Ser Gly Asn Ala Pro Ser Glu Met Lys Glu Pro Tyr Arg Leu Glu Gly
                180                 185                 190

Ala Met Pro Glu Ala Gln Leu Leu Met Arg Val Glu Ile Val Asn
                195                 200                 205

Gly Leu Ala Asp Tyr Ala Arg Asn Tyr Ala Gln Ala Ile Arg Asp Ala
        210                 215                 220

Val Asn Leu Gly Ala Lys Val Ile Asn Met Ser Phe Gly Asn Ala Ala
225                 230                 235                 240

Leu Ala Tyr Ala Asn Leu Pro Asp Glu Thr Lys Lys Ala Phe Asp Tyr
                245                 250                 255

Ala Lys Ser Lys Gly Val Ser Ile Val Thr Ser Ala Gly Asn Asp Ser
                260                 265                 270

Ser Phe Gly Gly Lys Pro Arg Leu Pro Leu Ala Asp His Pro Asp Tyr
        275                 280                 285

Gly Val Val Gly Thr Pro Ala Ala Ala Asp Ser Thr Leu Thr Val Ala
        290                 295                 300

Ser Tyr Ser Pro Asp Lys Gln Leu Thr Glu Thr Ala Thr Val Lys Thr
305                 310                 315                 320

Asp Asp His Gln Asp Lys Glu Met Pro Val Ile Ser Thr Asn Arg Phe
                325                 330                 335

Glu Pro Asn Lys Ala Tyr Asp Tyr Ala Tyr Ala Asn Arg Gly Thr Lys
                340                 345                 350

Glu Asp Asp Phe Lys Asp Val Glu Gly Lys Ile Ala Leu Ile Glu Arg
        355                 360                 365

Gly Asp Ile Asp Phe Lys Asp Lys Ile Ala Asn Ala Lys Lys Ala Gly
        370                 375                 380

Ala Val Gly Val Leu Ile Tyr Asp Asn Gln Asp Lys Gly Phe Pro Ile
385                 390                 395                 400

Glu Leu Pro Asn Val Asp Gln Met Pro Ala Ala Phe Ile Ser Arg Arg
                405                 410                 415

Asp Gly Leu Leu Leu Lys Asp Asn Pro Pro Lys Thr Ile Thr Phe Asn
                420                 425                 430

Ala Thr Pro Lys Val Leu Pro Thr Ala Ser Gly Thr Lys Leu Ser Arg
                435                 440                 445

Phe Ser Ser Trp Gly Leu Thr Ala Asp Gly Asn Ile Lys Pro Asp Ile
        450                 455                 460

Ala Ala Pro Gly Gln Asp Ile Leu Ser Ser Val Ala Asn Asn Lys Tyr
465                 470                 475                 480

Ala Lys Leu Ser Gly Thr Ser Met Ser Ala Pro Leu Val Ala Gly Ile
                485                 490                 495

Met Gly Leu Leu Gln Lys Gln Tyr Glu Thr Gln Tyr Pro Asp Met Thr
                500                 505                 510

Pro Ser Glu Arg Leu Asp Leu Ala Lys Lys Val Leu Met Ser Ser Ala
                515                 520                 525

Thr Ala Leu Tyr Asp Glu Asp Glu Lys Ala Tyr Phe Ser Pro Arg Gln
                530                 535                 540
```

```
Gln Gly Ala Gly Ala Val Asp Ala Lys Lys Ala Ser Ala Ala Thr Met
545                 550                 555                 560

Tyr Val Thr Asp Lys Asp Asn Thr Ser Ser Lys Val His Leu Asn Asn
            565                 570                 575

Val Ser Asp Lys Phe Glu Val Thr Val Thr Val His Asn Lys Ser Asp
            580                 585                 590

Lys Pro Gln Glu Leu Tyr Tyr Gln Val Thr Val Gln Thr Asp Lys Val
            595                 600                 605

Asp Gly Lys His Phe Ala Leu Ala Pro Lys Ala Leu Tyr Glu Thr Ser
            610                 615                 620

Trp Gln Lys Ile Thr Ile Pro Ala Asn Ser Ser Lys Gln Val Thr Val
625                 630                 635                 640

Pro Ile Asp Ala Ser Arg Phe Ser Lys Asp Leu Leu Ala Gln Met Lys
                645                 650                 655

Asn Gly Tyr Phe Leu Glu Gly Phe Val Arg Phe Lys Gln Asp Pro Thr
                660                 665                 670

Lys Glu Glu Leu Met Ser Ile Pro Tyr Ile Gly Phe Arg Gly Asp Phe
            675                 680                 685

Gly Asn Leu Ser Ala Leu Glu Lys Pro Ile Tyr Asp Ser Lys Asp Gly
690                 695                 700

Ser Ser Tyr Tyr His Glu Ala Asn Ser Asp Ala Lys Asp Gln Leu Asp
705                 710                 715                 720

Gly Asp Gly Leu Gln Phe Tyr Ala Leu Lys Asn Asn Phe Thr Ala Leu
                725                 730                 735

Thr Thr Glu Ser Asn Pro Trp Thr Ile Ile Lys Ala Val Lys Glu Gly
                740                 745                 750

Val Glu Asn Ile Glu Asp Ile Glu Ser Ser Glu Ile Thr Glu Thr Ile
            755                 760                 765

Phe Ala Gly Thr Phe Ala Lys Gln Asp Asp Asp Ser His Tyr Tyr Ile
770                 775                 780

His Arg His Ala Asn Gly Lys Pro Tyr Ala Ala Ile Ser Pro Asn Gly
785                 790                 795                 800

Asp Gly Asn Arg Asp Tyr Val Gln Phe Gln Gly Thr Phe Leu Arg Asn
                805                 810                 815

Ala Lys Asn Leu Val Ala Glu Val Leu Asp Lys Glu Gly Asn Val Val
                820                 825                 830

Trp Thr Ser Glu Val Thr Glu Gln Val Val Lys Asn Tyr Asn Asn Asp
                835                 840                 845

Leu Ala Ser Thr Leu Gly Ser Thr Arg Phe Glu Lys Thr Arg Trp Asp
850                 855                 860

Gly Lys Asp Lys Asp Gly Lys Val Val Ala Asn Gly Thr Tyr Thr Tyr
865                 870                 875                 880

Arg Val Arg Tyr Thr Pro Ile Ser Ser Gly Ala Lys Glu Gln His Thr
                885                 890                 895

Asp Phe Asp Val Ile Val Asp Asn Thr Thr Pro Glu Val Ala Thr Ser
                900                 905                 910

Ala Thr Phe Ser Thr Glu Asp Ser Arg Leu Thr Leu Ala Ser Lys Pro
                915                 920                 925

Lys Thr Ser Gln Pro Val Tyr Arg Glu Arg Ile Ala Tyr Thr Tyr Met
            930                 935                 940

Asp Glu Asp Leu Pro Thr Thr Glu Tyr Ile Ser Pro Asn Glu Asp Gly
945                 950                 955                 960
```

```
Thr Phe Thr Leu Pro Glu Glu Ala Glu Thr Met Glu Gly Ala Thr Val
            965                 970                 975
Pro Leu Lys Met Ser Asp Phe Thr Tyr Val Val Glu Asp Met Ala Gly
        980                 985                 990
Asn Ile Thr Tyr Thr Pro Val Thr Lys Leu Leu Glu Gly His Ser Asn
        995                 1000                1005
Lys Pro Glu Gln Asp Gly Ser Asp Gln Ala Pro Asp Lys Lys Pro Glu
        1010                1015                1020
Ala Lys Pro Glu Gln Asp Gly Ser Gly Gln Thr Pro Asp Lys Lys Lys
1025                1030                1035                1040
Glu Thr Lys Pro Glu Lys Asp Ser Ser Gly Gln Thr Pro Gly Lys Thr
            1045                1050                1055
Pro Gln Lys Gly Gln Ser Ser Arg Thr Leu Glu Lys Arg Ser Ser Lys
            1060                1065                1070
Arg Ala Leu Ala Thr Lys Ala Ser Thr Arg Asp Gln Leu Pro Thr Thr
            1075                1080                1085
Asn Asp Lys Asp Thr Asn Arg Leu His Leu Leu Lys Val Met Thr
            1090                1095                1100
Thr Phe Phe Leu Gly
1105

<210> SEQ ID NO 15
<211> LENGTH: 1103
<212> TYPE: PRT
<213> ORGANISM: Streptococcus agalactiae

<400> SEQUENCE: 15

Met Arg Lys Lys Gln Lys Leu Pro Phe Asp Lys Leu Ala Ile Ala Leu
1               5                   10                  15
Ile Ser Thr Ser Ile Leu Leu Asn Ala Gln Ser Asp Ile Lys Ala Asn
            20                  25                  30
Thr Val Thr Glu Asp Thr Pro Ala Thr Glu Gln Ala Val Glu Pro Pro
        35                  40                  45
Gln Pro Ile Ala Val Ser Glu Glu Ser Arg Ser Ser Lys Glu Thr Lys
    50                  55                  60
Thr Ser Gln Thr Pro Ser Asp Val Gly Glu Thr Val Ala Asp Asp Ala
65                  70                  75                  80
Asn Asp Leu Ala Pro Gln Ala Pro Ala Lys Thr Ala Asp Thr Pro Ala
            85                  90                  95
Thr Ser Lys Ala Thr Ile Arg Asp Leu Asn Asp Pro Ser His Val Lys
        100                 105                 110
Thr Leu Gln Glu Lys Ala Gly Lys Gly Ala Gly Thr Val Val Ala Val
        115                 120                 125
Ile Asp Ala Gly Phe Asp Lys Asn His Glu Ala Trp Arg Leu Thr Asp
    130                 135                 140
Lys Thr Lys Ala Arg Tyr Gln Ser Lys Glu Asn Leu Glu Lys Ala Lys
145                 150                 155                 160
Lys Glu His Gly Ile Thr Tyr Gly Glu Trp Val Asn Asp Lys Val Ala
            165                 170                 175
Tyr Tyr His Asp Tyr Ser Lys Asp Gly Lys Asn Ala Val Asp Gln Glu
        180                 185                 190
His Gly Thr His Val Ser Gly Ile Leu Ser Gly Asn Ala Pro Ser Glu
        195                 200                 205
Met Lys Glu Pro Tyr Arg Leu Glu Gly Ala Met Pro Glu Ala Gln Leu
    210                 215                 220
```

```
Leu Leu Met Arg Val Glu Ile Val Asn Gly Leu Ala Asp Tyr Ala Arg
225                 230                 235                 240

Asn Tyr Ala Gln Ala Ile Arg Asp Ala Val Asn Leu Gly Ala Lys Val
            245                 250                 255

Ile Asn Met Ser Phe Gly Asn Ala Ala Leu Ala Tyr Ala Asn Leu Pro
        260                 265                 270

Asp Glu Thr Lys Lys Ala Phe Asp Tyr Ala Lys Ser Lys Gly Val Ser
    275                 280                 285

Ile Val Thr Ser Ala Gly Asn Asp Ser Ser Phe Gly Gly Lys Pro Arg
290                 295                 300

Leu Pro Leu Ala Asp His Pro Asp Tyr Gly Val Val Gly Thr Pro Ala
305                 310                 315                 320

Ala Ala Asp Ser Thr Leu Thr Val Ala Ser Tyr Ser Pro Asp Lys Gln
            325                 330                 335

Leu Thr Glu Thr Ala Thr Val Lys Thr Asp His Gln Asp Lys Glu
        340                 345                 350

Met Pro Val Ile Ser Thr Asn Arg Phe Glu Pro Asn Lys Ala Tyr Asp
    355                 360                 365

Tyr Ala Tyr Ala Asn Arg Gly Thr Lys Glu Asp Phe Lys Asp Val
370                 375                 380

Glu Gly Lys Ile Ala Leu Ile Glu Arg Gly Asp Ile Asp Phe Lys Asp
385                 390                 395                 400

Lys Ile Ala Asn Ala Lys Lys Ala Gly Ala Val Gly Val Leu Ile Tyr
            405                 410                 415

Asp Asn Gln Asp Lys Gly Phe Pro Ile Glu Leu Pro Asn Val Asp Gln
        420                 425                 430

Met Pro Ala Ala Phe Ile Ser Arg Arg Asp Gly Leu Leu Leu Lys Asp
    435                 440                 445

Asn Pro Pro Lys Thr Ile Thr Phe Asn Ala Thr Pro Lys Val Leu Pro
450                 455                 460

Thr Ala Ser Gly Thr Lys Leu Ser Arg Phe Ser Ser Trp Gly Leu Thr
465                 470                 475                 480

Ala Asp Gly Asn Ile Lys Pro Asp Ile Ala Ala Pro Gly Gln Asp Ile
            485                 490                 495

Leu Ser Ser Val Ala Asn Asn Lys Tyr Ala Lys Leu Ser Gly Thr Ser
        500                 505                 510

Met Ser Ala Pro Leu Val Ala Gly Ile Met Gly Leu Leu Gln Lys Gln
    515                 520                 525

Tyr Glu Thr Gln Tyr Pro Asp Met Thr Pro Ser Glu Arg Leu Asp Leu
530                 535                 540

Ala Lys Lys Val Leu Met Ser Ser Ala Thr Ala Leu Tyr Asp Glu Asp
545                 550                 555                 560

Glu Lys Ala Tyr Phe Ser Pro Arg Gln Gln Gly Ala Gly Ala Val Asp
            565                 570                 575

Ala Lys Lys Ala Ser Ala Ala Thr Met Tyr Val Thr Asp Lys Asp Asn
        580                 585                 590

Thr Ser Ser Lys Val His Leu Asn Asn Val Ser Asp Lys Phe Glu Val
    595                 600                 605

Thr Val Thr Val His Asn Lys Ser Asp Lys Pro Gln Glu Leu Tyr Tyr
610                 615                 620

Gln Val Thr Val Gln Thr Asp Lys Val Asp Gly Lys His Phe Ala Leu
625                 630                 635                 640
```

```
Ala Pro Lys Ala Leu Tyr Glu Thr Ser Trp Gln Lys Ile Thr Ile Pro
                645                 650                 655

Ala Asn Ser Ser Lys Gln Val Thr Val Pro Ile Asp Ala Ser Arg Phe
            660                 665                 670

Ser Lys Asp Leu Leu Ala Gln Met Lys Asn Gly Tyr Phe Leu Glu Gly
        675                 680                 685

Phe Val Arg Phe Lys Gln Asp Pro Thr Lys Glu Glu Leu Met Ser Ile
    690                 695                 700

Pro Tyr Ile Gly Phe Arg Gly Asp Phe Gly Asn Leu Ser Ala Leu Glu
705                 710                 715                 720

Lys Pro Ile Tyr Asp Ser Lys Asp Gly Ser Ser Tyr Tyr His Glu Ala
                725                 730                 735

Asn Ser Asp Ala Lys Asp Gln Leu Asp Gly Asp Gly Leu Gln Phe Tyr
            740                 745                 750

Ala Leu Lys Asn Asn Phe Thr Ala Leu Thr Thr Glu Ser Asn Pro Trp
        755                 760                 765

Thr Ile Ile Lys Ala Val Lys Glu Gly Val Glu Asn Ile Glu Asp Ile
    770                 775                 780

Glu Ser Ser Glu Ile Thr Glu Thr Ile Phe Ala Gly Thr Phe Ala Lys
785                 790                 795                 800

Gln Asp Asp Asp Ser His Tyr Tyr Ile His Arg His Ala Asn Gly Lys
                805                 810                 815

Pro Tyr Ala Ala Ile Ser Pro Asn Gly Asp Gly Asn Arg Asp Tyr Val
            820                 825                 830

Gln Phe Gln Gly Thr Phe Leu Arg Asn Ala Lys Asn Leu Val Ala Glu
        835                 840                 845

Val Leu Asp Lys Glu Gly Asn Val Val Trp Thr Ser Glu Val Thr Glu
    850                 855                 860

Gln Val Val Lys Asn Tyr Asn Asn Asp Leu Ala Ser Thr Leu Gly Ser
865                 870                 875                 880

Thr Arg Phe Glu Lys Thr Arg Trp Asp Gly Lys Asp Lys Asp Gly Lys
                885                 890                 895

Val Val Ala Asn Gly Thr Tyr Thr Tyr Arg Val Arg Tyr Thr Pro Ile
            900                 905                 910

Ser Ser Gly Ala Lys Glu Gln His Thr Asp Phe Asp Val Ile Val Asp
        915                 920                 925

Asn Thr Thr Pro Glu Val Ala Thr Ser Ala Thr Phe Ser Thr Glu Asp
    930                 935                 940

Ser Arg Leu Thr Leu Ala Ser Lys Pro Lys Thr Ser Gln Pro Val Tyr
945                 950                 955                 960

Arg Glu Arg Ile Ala Tyr Thr Tyr Met Asp Glu Asp Leu Pro Thr Thr
                965                 970                 975

Glu Tyr Ile Ser Pro Asn Glu Asp Gly Thr Phe Thr Leu Pro Glu Glu
            980                 985                 990

Ala Glu Thr Met Glu Gly Ala Thr Val Pro Leu Lys Met Ser Asp Phe
        995                 1000                1005

Thr Tyr Val Val Glu Asp Met Ala Gly Asn Ile Thr Tyr Thr Pro Val
    1010                1015                1020

Thr Lys Leu Leu Glu Gly His Ser Asn Lys Pro Glu Gln Asp Gly Ser
1025                1030                1035                1040

Asp Gln Ala Pro Asp Lys Lys Pro Glu Ala Lys Pro Glu Gln Asp Gly
                1045                1050                1055

Ser Gly Gln Thr Pro Asp Lys Lys Lys Glu Thr Lys Pro Glu Lys Asp
```

-continued

```
                  1060                1065                1070
Ser Ser Gly Gln Thr Pro Gly Lys Thr Pro Gln Lys Gly Gln Ser Ser
        1075                1080                1085
Arg Thr Leu Glu Lys Arg Ser Ser Lys Arg Ala Leu Ala Thr Lys
        1090                1095                1100

<210> SEQ ID NO 16
<211> LENGTH: 1078
<212> TYPE: PRT
<213> ORGANISM: Streptococcus agalactiae

<400> SEQUENCE: 16

Gln Ser Asp Ile Lys Ala Asn Thr Val Thr Glu Asp Thr Pro Ala Thr
1               5                   10                  15

Glu Gln Ala Val Glu Pro Pro Gln Pro Ile Ala Val Ser Glu Glu Ser
            20                  25                  30

Arg Ser Ser Lys Glu Thr Lys Thr Ser Gln Thr Pro Ser Asp Val Gly
        35                  40                  45

Glu Thr Val Ala Asp Asp Ala Asn Asp Leu Ala Pro Gln Ala Pro Ala
    50                  55                  60

Lys Thr Ala Asp Thr Pro Ala Thr Ser Lys Ala Thr Ile Arg Asp Leu
65                  70                  75                  80

Asn Asp Pro Ser His Val Lys Thr Leu Gln Glu Lys Ala Gly Lys Gly
                85                  90                  95

Ala Gly Thr Val Val Ala Val Ile Asp Ala Gly Phe Asp Lys Asn His
            100                 105                 110

Glu Ala Trp Arg Leu Thr Asp Lys Thr Lys Ala Arg Tyr Gln Ser Lys
        115                 120                 125

Glu Asn Leu Glu Lys Ala Lys Lys Glu His Gly Ile Thr Tyr Gly Glu
    130                 135                 140

Trp Val Asn Asp Lys Val Ala Tyr Tyr His Asp Tyr Ser Lys Asp Gly
145                 150                 155                 160

Lys Asn Ala Val Asp Gln Glu His Gly Thr His Val Ser Gly Ile Leu
                165                 170                 175

Ser Gly Asn Ala Pro Ser Glu Met Lys Glu Pro Tyr Arg Leu Glu Gly
            180                 185                 190

Ala Met Pro Glu Ala Gln Leu Leu Leu Met Arg Val Glu Ile Val Asn
        195                 200                 205

Gly Leu Ala Asp Tyr Ala Arg Asn Tyr Ala Gln Ala Ile Arg Asp Ala
    210                 215                 220

Val Asn Leu Gly Ala Lys Val Ile Asn Met Ser Phe Gly Asn Ala Ala
225                 230                 235                 240

Leu Ala Tyr Ala Asn Leu Pro Asp Glu Thr Lys Lys Ala Phe Asp Tyr
                245                 250                 255

Ala Lys Ser Lys Gly Val Ser Ile Val Thr Ser Ala Gly Asn Asp Ser
            260                 265                 270

Ser Phe Gly Gly Lys Pro Arg Leu Pro Leu Ala Asp His Pro Asp Tyr
        275                 280                 285

Gly Val Val Gly Thr Pro Ala Ala Ala Asp Ser Thr Leu Thr Val Ala
    290                 295                 300

Ser Tyr Ser Pro Asp Lys Gln Leu Thr Glu Thr Ala Thr Val Lys Thr
305                 310                 315                 320

Asp Asp His Gln Asp Lys Glu Met Pro Val Ile Ser Thr Asn Arg Phe
                325                 330                 335
```

-continued

```
Glu Pro Asn Lys Ala Tyr Asp Tyr Ala Tyr Ala Asn Arg Gly Thr Lys
            340                 345                 350

Glu Asp Asp Phe Lys Asp Val Glu Gly Lys Ile Ala Leu Ile Glu Arg
        355                 360                 365

Gly Asp Ile Asp Phe Lys Asp Lys Ile Ala Asn Ala Lys Lys Ala Gly
    370                 375                 380

Ala Val Gly Val Leu Ile Tyr Asp Asn Gln Asp Lys Gly Phe Pro Ile
385                 390                 395                 400

Glu Leu Pro Asn Val Asp Gln Met Pro Ala Ala Phe Ile Ser Arg Arg
            405                 410                 415

Asp Gly Leu Leu Leu Lys Asp Asn Pro Pro Lys Thr Ile Thr Phe Asn
        420                 425                 430

Ala Thr Pro Lys Val Leu Pro Thr Ala Ser Gly Thr Lys Leu Ser Arg
    435                 440                 445

Phe Ser Ser Trp Gly Leu Thr Ala Asp Gly Asn Ile Lys Pro Asp Ile
450                 455                 460

Ala Ala Pro Gly Gln Asp Ile Leu Ser Ser Val Ala Asn Asn Lys Tyr
465                 470                 475                 480

Ala Lys Leu Ser Gly Thr Ser Met Ser Ala Pro Leu Val Ala Gly Ile
            485                 490                 495

Met Gly Leu Leu Gln Lys Gln Tyr Glu Thr Gln Tyr Pro Asp Met Thr
        500                 505                 510

Pro Ser Glu Arg Leu Asp Leu Ala Lys Lys Val Leu Met Ser Ser Ala
    515                 520                 525

Thr Ala Leu Tyr Asp Glu Asp Glu Lys Ala Tyr Phe Ser Pro Arg Gln
530                 535                 540

Gln Gly Ala Gly Ala Val Asp Ala Lys Lys Ala Ser Ala Ala Thr Met
545                 550                 555                 560

Tyr Val Thr Asp Lys Asp Asn Thr Ser Ser Lys Val His Leu Asn Asn
            565                 570                 575

Val Ser Asp Lys Phe Glu Val Thr Val Thr Val His Asn Lys Ser Asp
        580                 585                 590

Lys Pro Gln Glu Leu Tyr Tyr Gln Val Thr Val Gln Thr Asp Lys Val
    595                 600                 605

Asp Gly Lys His Phe Ala Leu Ala Pro Lys Ala Leu Tyr Glu Thr Ser
610                 615                 620

Trp Gln Lys Ile Thr Ile Pro Ala Asn Ser Ser Lys Gln Val Thr Val
625                 630                 635                 640

Pro Ile Asp Ala Ser Arg Phe Ser Lys Asp Leu Leu Ala Gln Met Lys
            645                 650                 655

Asn Gly Tyr Phe Leu Glu Gly Phe Val Arg Phe Lys Gln Asp Pro Thr
        660                 665                 670

Lys Glu Glu Leu Met Ser Ile Pro Tyr Ile Gly Phe Arg Gly Asp Phe
    675                 680                 685

Gly Asn Leu Ser Ala Leu Glu Lys Pro Ile Tyr Asp Ser Lys Asp Gly
690                 695                 700

Ser Ser Tyr Tyr His Glu Ala Asn Ser Asp Ala Lys Asp Gln Leu Asp
705                 710                 715                 720

Gly Asp Gly Leu Gln Phe Tyr Ala Leu Lys Asn Asn Phe Thr Ala Leu
            725                 730                 735

Thr Thr Glu Ser Asn Pro Trp Thr Ile Ile Lys Ala Val Lys Glu Gly
        740                 745                 750

Val Glu Asn Ile Glu Asp Ile Glu Ser Ser Glu Ile Thr Glu Thr Ile
```

```
                    755                 760                 765
Phe Ala Gly Thr Phe Ala Lys Gln Asp Asp Ser His Tyr Tyr Ile
    770                 775                 780

His Arg His Ala Asn Gly Lys Pro Tyr Ala Ala Ile Ser Pro Asn Gly
785                 790                 795                 800

Asp Gly Asn Arg Asp Tyr Val Gln Phe Gln Gly Thr Phe Leu Arg Asn
                805                 810                 815

Ala Lys Asn Leu Val Ala Glu Val Leu Asp Lys Glu Gly Asn Val Val
            820                 825                 830

Trp Thr Ser Glu Val Thr Glu Gln Val Val Lys Asn Tyr Asn Asn Asp
        835                 840                 845

Leu Ala Ser Thr Leu Gly Ser Thr Arg Phe Glu Lys Thr Arg Trp Asp
    850                 855                 860

Gly Lys Asp Lys Asp Gly Lys Val Val Ala Asn Gly Thr Tyr Thr Tyr
865                 870                 875                 880

Arg Val Arg Tyr Thr Pro Ile Ser Ser Gly Ala Lys Glu Gln His Thr
                885                 890                 895

Asp Phe Asp Val Ile Val Asp Asn Thr Thr Pro Glu Val Ala Thr Ser
            900                 905                 910

Ala Thr Phe Ser Thr Glu Asp Ser Arg Leu Thr Leu Ala Ser Lys Pro
        915                 920                 925

Lys Thr Ser Gln Pro Val Tyr Arg Glu Arg Ile Ala Tyr Thr Tyr Met
    930                 935                 940

Asp Glu Asp Leu Pro Thr Thr Glu Tyr Ile Ser Pro Asn Glu Asp Gly
945                 950                 955                 960

Thr Phe Thr Leu Pro Glu Glu Ala Glu Thr Met Gly Ala Thr Val
                965                 970                 975

Pro Leu Lys Met Ser Asp Phe Thr Tyr Val Val Glu Asp Met Ala Gly
            980                 985                 990

Asn Ile Thr Tyr Thr Pro Val Thr Lys Leu Leu Glu Gly His Ser Asn
        995                 1000                1005

Lys Pro Glu Gln Asp Gly Ser Asp Gln Ala Pro Asp Lys Lys Pro Glu
    1010                1015                1020

Ala Lys Pro Glu Gln Asp Gly Ser Gly Gln Thr Pro Asp Lys Lys Lys
1025                1030                1035                1040

Glu Thr Lys Pro Glu Lys Asp Ser Ser Gly Gln Thr Pro Gly Lys Thr
                1045                1050                1055

Pro Gln Lys Gly Gln Ser Ser Arg Thr Leu Glu Lys Arg Ser Ser Lys
            1060                1065                1070

Arg Ala Leu Ala Thr Lys
        1075

<210> SEQ ID NO 17
<211> LENGTH: 392
<212> TYPE: PRT
<213> ORGANISM: Streptococcus agalactiae

<400> SEQUENCE: 17

Asp Leu Val Lys Gln Asp Asn Lys Ser Ser Tyr Thr Val Lys Tyr Gly
1               5                   10                  15

Asp Thr Leu Ser Val Ile Ser Glu Ala Met Ser Ile Asp Met Asn Val
                20                  25                  30

Leu Ala Lys Ile Asn Asn Ile Ala Asp Ile Asn Leu Ile Tyr Pro Glu
            35                  40                  45
```

```
Thr Thr Leu Thr Val Thr Tyr Asp Gln Lys Ser His Thr Ala Thr Ser
 50                  55                  60

Met Lys Ile Glu Thr Pro Ala Thr Asn Ala Ala Gly Gln Thr Thr Ala
 65                  70                  75                  80

Thr Val Asp Leu Lys Thr Asn Gln Val Ser Val Ala Asp Gln Lys Val
                 85                  90                  95

Ser Leu Asn Thr Ile Ser Glu Gly Met Thr Pro Glu Ala Ala Thr Thr
                100                 105                 110

Ile Val Ser Pro Met Lys Thr Tyr Ser Ser Ala Pro Ala Leu Lys Ser
                115                 120                 125

Lys Glu Val Leu Ala Gln Glu Gln Ala Val Ser Gln Ala Ala Ala Asn
130                 135                 140

Glu Gln Val Ser Pro Ala Pro Val Lys Ser Ile Thr Ser Glu Val Pro
145                 150                 155                 160

Ala Ala Lys Glu Glu Val Lys Pro Thr Gln Thr Ser Val Ser Gln Ser
                165                 170                 175

Thr Thr Val Ser Pro Ala Ser Val Ala Ala Glu Thr Pro Ala Pro Val
                180                 185                 190

Ala Lys Val Ala Pro Val Arg Thr Val Ala Ala Pro Arg Val Ala Ser
                195                 200                 205

Val Lys Val Val Thr Pro Lys Val Glu Thr Gly Ala Ser Pro Glu His
210                 215                 220

Val Ser Ala Pro Ala Val Pro Val Thr Thr Thr Ser Pro Ala Thr Asp
225                 230                 235                 240

Ser Lys Leu Gln Ala Thr Glu Val Lys Ser Val Pro Val Ala Gln Lys
                245                 250                 255

Ala Pro Thr Ala Thr Pro Val Ala Gln Pro Ala Ser Thr Thr Asn Ala
                260                 265                 270

Val Ala Ala His Pro Glu Asn Ala Gly Leu Gln Pro His Val Ala Ala
                275                 280                 285

Tyr Lys Glu Lys Val Ala Ser Thr Tyr Gly Val Asn Glu Phe Ser Thr
                290                 295                 300

Tyr Arg Ala Gly Asp Pro Gly Asp His Gly Lys Gly Leu Ala Val Asp
305                 310                 315                 320

Phe Ile Val Gly Thr Asn Gln Ala Leu Gly Asn Lys Val Ala Gln Tyr
                325                 330                 335

Ser Thr Gln Asn Met Ala Ala Asn Asn Ile Ser Tyr Val Ile Trp Gln
                340                 345                 350

Gln Lys Phe Tyr Ser Asn Thr Asn Ser Ile Tyr Gly Pro Ala Asn Thr
                355                 360                 365

Trp Asn Ala Met Pro Asp Arg Gly Gly Val Thr Ala Asn His Tyr Asp
370                 375                 380

His Val His Val Ser Phe Asn Lys
385                 390

<210> SEQ ID NO 18
<211> LENGTH: 869
<212> TYPE: PRT
<213> ORGANISM: Streptococcus agalactiae

<400> SEQUENCE: 18

Met Arg Lys Tyr Gln Lys Phe Ser Lys Ile Leu Thr Leu Ser Leu Phe
 1                   5                  10                  15

Cys Leu Ser Gln Ile Pro Leu Asn Thr Asn Val Leu Gly Glu Ser Thr
                 20                  25                  30
```

```
Val Pro Glu Asn Gly Ala Lys Gly Lys Leu Val Lys Lys Thr Asp
            35                  40                  45
Asp Gln Asn Lys Pro Leu Ser Lys Ala Thr Phe Val Leu Lys Thr Thr
 50                  55                  60
Ala His Pro Glu Ser Lys Ile Glu Lys Val Thr Ala Glu Leu Thr Gly
 65                  70                  75                  80
Glu Ala Thr Phe Asp Asn Leu Ile Pro Gly Asp Tyr Thr Leu Ser Glu
                85                  90                  95
Glu Thr Ala Pro Glu Gly Tyr Lys Lys Thr Asn Gln Thr Trp Gln Val
                100                 105                 110
Lys Val Glu Ser Asn Gly Lys Thr Thr Ile Gln Asn Ser Gly Asp Lys
            115                 120                 125
Asn Ser Thr Ile Gly Gln Asn Gln Glu Leu Asp Lys Gln Tyr Pro
            130                 135                 140
Pro Thr Gly Ile Tyr Glu Asp Thr Lys Glu Ser Tyr Lys Leu Glu His
 145                 150                 155                 160
Val Lys Gly Ser Val Pro Asn Gly Lys Ser Glu Ala Lys Ala Val Asn
                165                 170                 175
Pro Tyr Ser Ser Glu Gly Glu His Ile Arg Glu Ile Pro Glu Gly Thr
                180                 185                 190
Leu Ser Lys Arg Ile Ser Glu Val Gly Asp Leu Ala His Asn Lys Tyr
            195                 200                 205
Lys Ile Glu Leu Thr Val Ser Gly Lys Thr Ile Val Lys Pro Val Asp
 210                 215                 220
Lys Gln Lys Pro Leu Asp Val Val Phe Val Leu Asp Asn Ser Asn Ser
 225                 230                 235                 240
Met Asn Asn Asp Gly Pro Asn Phe Gln Arg His Asn Lys Ala Lys Lys
                245                 250                 255
Ala Ala Glu Ala Leu Gly Thr Ala Val Lys Asp Ile Leu Gly Ala Asn
                260                 265                 270
Ser Asp Asn Arg Val Ala Leu Val Thr Tyr Gly Ser Asp Ile Phe Asp
            275                 280                 285
Gly Arg Ser Val Asp Val Lys Gly Phe Lys Glu Asp Asp Lys Tyr
 290                 295                 300
Tyr Gly Leu Gln Thr Lys Phe Thr Ile Gln Thr Glu Asn Tyr Ser His
 305                 310                 315                 320
Lys Gln Leu Thr Asn Asn Ala Glu Glu Ile Ile Lys Arg Ile Pro Thr
            325                 330                 335
Glu Ala Pro Lys Ala Lys Trp Gly Ser Thr Thr Asn Gly Leu Thr Pro
                340                 345                 350
Glu Gln Gln Lys Glu Tyr Tyr Leu Ser Lys Val Gly Thr Phe Thr
            355                 360                 365
Met Lys Ala Phe Met Glu Ala Asp Asp Ile Leu Ser Gln Val Asn Arg
 370                 375                 380
Asn Ser Gln Lys Ile Ile Val His Val Thr Asp Gly Val Pro Thr Arg
 385                 390                 395                 400
Ser Tyr Ala Ile Asn Asn Phe Lys Leu Gly Ala Ser Tyr Glu Ser Gln
                405                 410                 415
Phe Glu Gln Met Lys Lys Asn Gly Tyr Leu Asn Lys Ser Asn Phe Leu
                420                 425                 430
Leu Thr Asp Lys Pro Glu Asp Ile Lys Gly Asn Gly Glu Ser Tyr Phe
            435                 440                 445
```

-continued

```
Leu Phe Pro Leu Asp Ser Tyr Gln Thr Gln Ile Ile Ser Gly Asn Leu
450                 455                 460

Gln Lys Leu His Tyr Leu Asp Leu Asn Leu Asn Tyr Pro Lys Gly Thr
465                 470                 475                 480

Ile Tyr Arg Asn Gly Pro Val Lys Glu His Gly Thr Pro Thr Lys Leu
                485                 490                 495

Tyr Ile Asn Ser Leu Lys Gln Lys Asn Tyr Asp Ile Phe Asn Phe Gly
            500                 505                 510

Ile Asp Ile Ser Gly Phe Arg Gln Val Tyr Asn Glu Glu Tyr Lys Lys
        515                 520                 525

Asn Gln Asp Gly Thr Phe Gln Lys Leu Lys Glu Glu Ala Phe Lys Leu
530                 535                 540

Ser Asp Gly Glu Ile Thr Glu Leu Met Arg Ser Phe Ser Ser Lys Pro
545                 550                 555                 560

Glu Tyr Tyr Thr Pro Ile Val Thr Ser Ala Asp Thr Ser Asn Asn Glu
                565                 570                 575

Ile Leu Ser Lys Ile Gln Gln Gln Phe Glu Thr Ile Leu Thr Lys Glu
            580                 585                 590

Asn Ser Ile Val Asn Gly Thr Ile Glu Asp Pro Met Gly Asp Lys Ile
        595                 600                 605

Asn Leu Gln Leu Gly Asn Gly Gln Thr Leu Gln Pro Ser Asp Tyr Thr
610                 615                 620

Leu Gln Gly Asn Asp Gly Ser Val Met Lys Asp Gly Ile Ala Thr Gly
625                 630                 635                 640

Gly Pro Asn Asn Asp Gly Gly Ile Leu Lys Gly Val Lys Leu Glu Tyr
                645                 650                 655

Ile Gly Asn Lys Leu Tyr Val Arg Gly Leu Asn Leu Gly Glu Gly Gln
            660                 665                 670

Lys Val Thr Leu Thr Tyr Asp Val Lys Leu Asp Asp Ser Phe Ile Ser
        675                 680                 685

Asn Lys Phe Tyr Asp Thr Asn Gly Arg Thr Thr Leu Asn Pro Lys Ser
690                 695                 700

Glu Asp Pro Asn Thr Leu Arg Asp Phe Pro Ile Pro Lys Ile Arg Asp
705                 710                 715                 720

Val Arg Glu Tyr Pro Thr Ile Thr Ile Lys Asn Glu Lys Lys Leu Gly
                725                 730                 735

Glu Ile Glu Phe Ile Lys Val Asp Lys Asp Asn Asn Lys Leu Leu Leu
            740                 745                 750

Lys Gly Ala Thr Phe Glu Leu Gln Glu Phe Asn Glu Asp Tyr Lys Leu
        755                 760                 765

Tyr Leu Pro Ile Lys Asn Asn Asn Ser Lys Val Val Thr Gly Glu Asn
770                 775                 780

Gly Lys Ile Ser Tyr Lys Asp Leu Lys Asp Gly Lys Tyr Gln Leu Ile
785                 790                 795                 800

Glu Ala Val Ser Pro Glu Asp Tyr Gln Lys Ile Thr Asn Lys Pro Ile
                805                 810                 815

Leu Thr Phe Glu Val Val Lys Gly Ser Ile Lys Asn Ile Ile Ala Val
            820                 825                 830

Asn Lys Gln Ile Ser Glu Tyr His Glu Glu Gly Asp Lys His Leu Ile
        835                 840                 845

Thr Asn Thr His Ile Pro Pro Lys Gly Ile Ile Pro Met Thr Gly Gly
850                 855                 860

Lys Gly Ile Leu Ser
```

<210> SEQ ID NO 19
<211> LENGTH: 858
<212> TYPE: PRT
<213> ORGANISM: Streptococcus agalactiae

<400> SEQUENCE: 19

Met Arg Lys Tyr Gln Lys Phe Ser Lys Ile Leu Thr Leu Ser Leu Phe
1               5                   10                  15

Cys Leu Ser Gln Ile Pro Leu Asn Thr Asn Val Leu Gly Glu Ser Thr
            20                  25                  30

Val Pro Glu Asn Gly Ala Lys Gly Lys Leu Val Val Lys Lys Thr Asp
        35                  40                  45

Asp Gln Asn Lys Pro Leu Ser Lys Ala Thr Phe Val Leu Lys Thr Thr
    50                  55                  60

Ala His Pro Glu Ser Lys Ile Glu Lys Val Thr Ala Glu Leu Thr Gly
65                  70                  75                  80

Glu Ala Thr Phe Asp Asn Leu Ile Pro Gly Asp Tyr Thr Leu Ser Glu
                85                  90                  95

Glu Thr Ala Pro Glu Gly Tyr Lys Lys Thr Asn Gln Thr Trp Gln Val
            100                 105                 110

Lys Val Glu Ser Asn Gly Lys Thr Thr Ile Gln Asn Ser Gly Asp Lys
        115                 120                 125

Asn Ser Thr Ile Gly Gln Asn Gln Glu Glu Leu Asp Lys Gln Tyr Pro
    130                 135                 140

Pro Thr Gly Ile Tyr Glu Asp Thr Lys Glu Ser Tyr Lys Leu Glu His
145                 150                 155                 160

Val Lys Gly Ser Val Pro Asn Gly Lys Ser Glu Ala Lys Ala Val Asn
                165                 170                 175

Pro Tyr Ser Ser Glu Gly Glu His Ile Arg Glu Ile Pro Glu Gly Thr
            180                 185                 190

Leu Ser Lys Arg Ile Ser Glu Val Gly Asp Leu Ala His Asn Lys Tyr
        195                 200                 205

Lys Ile Glu Leu Thr Val Ser Gly Lys Thr Ile Val Lys Pro Val Asp
    210                 215                 220

Lys Gln Lys Pro Leu Asp Val Val Phe Val Leu Asp Asn Ser Asn Ser
225                 230                 235                 240

Met Asn Asn Asp Gly Pro Asn Phe Gln Arg His Asn Lys Ala Lys Lys
                245                 250                 255

Ala Ala Glu Ala Leu Gly Thr Ala Val Lys Asp Ile Leu Gly Ala Asn
            260                 265                 270

Ser Asp Asn Arg Val Ala Leu Val Thr Tyr Gly Ser Asp Ile Phe Asp
        275                 280                 285

Gly Arg Ser Val Asp Val Val Lys Gly Phe Lys Glu Asp Asp Lys Tyr
    290                 295                 300

Tyr Gly Leu Gln Thr Lys Phe Thr Ile Gln Thr Glu Asn Tyr Ser His
305                 310                 315                 320

Lys Gln Leu Thr Asn Asn Ala Glu Glu Ile Ile Lys Arg Ile Pro Thr
                325                 330                 335

Glu Ala Pro Lys Ala Lys Trp Gly Ser Thr Thr Asn Gly Leu Thr Pro
            340                 345                 350

Glu Gln Gln Lys Glu Tyr Tyr Leu Ser Lys Val Gly Thr Phe Thr
        355                 360                 365

```
Met Lys Ala Phe Met Glu Ala Asp Asp Ile Leu Ser Gln Val Asn Arg
370                 375                 380

Asn Ser Gln Lys Ile Ile Val His Val Thr Asp Gly Val Pro Thr Arg
385                 390                 395                 400

Ser Tyr Ala Ile Asn Asn Phe Lys Leu Gly Ala Ser Tyr Glu Ser Gln
        405                 410                 415

Phe Glu Gln Met Lys Lys Asn Gly Tyr Leu Asn Lys Ser Asn Phe Leu
            420                 425                 430

Leu Thr Asp Lys Pro Glu Asp Ile Lys Gly Asn Gly Glu Ser Tyr Phe
        435                 440                 445

Leu Phe Pro Leu Asp Ser Tyr Gln Thr Gln Ile Ile Ser Gly Asn Leu
450                 455                 460

Gln Lys Leu His Tyr Leu Asp Leu Asn Leu Asn Tyr Pro Lys Gly Thr
465                 470                 475                 480

Ile Tyr Arg Asn Gly Pro Val Lys Glu His Gly Thr Pro Thr Lys Leu
            485                 490                 495

Tyr Ile Asn Ser Leu Lys Gln Lys Asn Tyr Asp Ile Phe Asn Phe Gly
        500                 505                 510

Ile Asp Ile Ser Gly Phe Arg Gln Val Tyr Asn Glu Glu Tyr Lys Lys
        515                 520                 525

Asn Gln Asp Gly Thr Phe Gln Lys Leu Lys Glu Glu Ala Phe Lys Leu
530                 535                 540

Ser Asp Gly Glu Ile Thr Glu Leu Met Arg Ser Phe Ser Ser Lys Pro
545                 550                 555                 560

Glu Tyr Tyr Thr Pro Ile Val Thr Ser Ala Asp Thr Ser Asn Asn Glu
            565                 570                 575

Ile Leu Ser Lys Ile Gln Gln Phe Glu Thr Ile Leu Thr Lys Glu
        580                 585                 590

Asn Ser Ile Val Asn Gly Thr Ile Glu Asp Pro Met Gly Asp Lys Ile
        595                 600                 605

Asn Leu Gln Leu Gly Asn Gly Gln Thr Leu Gln Pro Ser Asp Tyr Thr
        610                 615                 620

Leu Gln Gly Asn Asp Gly Ser Val Met Lys Asp Gly Ile Ala Thr Gly
625                 630                 635                 640

Gly Pro Asn Asn Asp Gly Gly Ile Leu Lys Gly Val Lys Leu Glu Tyr
            645                 650                 655

Ile Gly Asn Lys Leu Tyr Val Arg Gly Leu Asn Leu Gly Glu Gly Gln
            660                 665                 670

Lys Val Thr Leu Thr Tyr Asp Val Lys Leu Asp Ser Phe Ile Ser
            675                 680                 685

Asn Lys Phe Tyr Asp Thr Asn Gly Arg Thr Thr Leu Asn Pro Lys Ser
        690                 695                 700

Glu Asp Pro Asn Thr Leu Arg Asp Phe Pro Ile Pro Lys Ile Arg Asp
705                 710                 715                 720

Val Arg Glu Tyr Pro Thr Ile Thr Ile Lys Asn Glu Lys Lys Leu Gly
            725                 730                 735

Glu Ile Glu Phe Ile Lys Val Asp Lys Asp Asn Asn Lys Leu Leu Leu
            740                 745                 750

Lys Gly Ala Thr Phe Glu Leu Gln Glu Phe Asn Glu Asp Tyr Lys Leu
        755                 760                 765

Tyr Leu Pro Ile Lys Asn Asn Asn Ser Lys Val Val Thr Gly Glu Asn
770                 775                 780

Gly Lys Ile Ser Tyr Lys Asp Leu Lys Asp Gly Lys Tyr Gln Leu Ile
```

```
              785                 790                 795                 800
Glu Ala Val Ser Pro Glu Asp Tyr Gln Lys Ile Thr Asn Lys Pro Ile
                805                 810                 815

Leu Thr Phe Glu Val Val Lys Gly Ser Ile Lys Asn Ile Ile Ala Val
                820                 825                 830

Asn Lys Gln Ile Ser Glu Tyr His Glu Glu Gly Asp Lys His Leu Ile
                835                 840                 845

Thr Asn Thr His Ile Pro Pro Lys Gly Ile
                850                 855
```

CONJUGATION OF STREPTOCOCCAL CAPSULAR SACCHARIDES

All documents cited herein are incorporated by reference in their entirety.

This application is a divisional of U.S. application Ser. No. 11/883,614, filed Mar. 18, 2008, now allowed, which is a U.S. National Stage application under 35 U.S.C. §371 of International Application PCT/IB2006/000756 (published as WO 2006/082530 A1), filed Feb. 1, 2006, which claims priority to Application GB 0502095.3, filed Feb. 1, 2005. Benefit of the filing date of each of these prior applications is hereby claimed. Each of these prior applications is hereby incorporated by reference in its entirety.

This application incorporates by reference the contents of a 117 kb text file created on Jul. 22, 2013 and named "SN13912919sequencelisting.txt," which is the sequence listing for this application.

TECHNICAL FIELD

This invention is in the field of conjugating bacterial capsular saccharides to carriers in order to form glycoconjugates. The glycoconjugates are useful for immunisation.

BACKGROUND ART

The capsular saccharides of bacteria have been used for many years in vaccines against capsulated bacteria. As saccharides are T-independent antigens, however, they are poorly immunogenic. Conjugation to a carrier can convert T-independent antigens into T-dependent antigens, thereby enhancing memory responses and allowing protective immunity to develop. The most effective saccharide vaccines are therefore based on glycoconjugates, and the prototype conjugate vaccine was against *Haemophilus influenzae* type b ('Hib') [e.g. see chapter 14 of ref. 78].

Another bacterium for which conjugate vaccines have been described is *Streptococcus agalactiae*, also known as 'group B streptococcus', or simply as 'GBS'. Much of this work has been performed by Dennis Kasper and colleagues, and is described in documents such as references 1 to 9. The Kasper process for GBS saccharide conjugation typically involves reductive amination of a purified saccharide to a carrier protein such as tetanus toxoid (TT) or CRM197 [2]. The reductive amination involves an amine group on the side chain of an amino acid in the carrier and an aldehyde group in the saccharide. As GBS capsular saccharides do not include an aldehyde group in their natural form then this is generated before conjugation by periodate oxidation of a portion of the saccharides sialic acid residues, as shown in FIG. 1 [2,10].

Although conjugate vaccines prepared in this manner for each of GBS serotypes Ia, Ib, II, III, and V have been shown to be safe and immunogenic in humans [11], there remains a need for further and better ways of preparing conjugates of GBS capsular saccharides.

DISCLOSURE OF THE INVENTION

The invention is based on three conjugation methods that can be used in place of the direct reductive amination disclosed in the prior art, all of which aim (a) to retain sialic acid residues in a form that is closer than the prior art to the form see in the native polysaccharide, and (b) to allow the use of a linker in the conjugation reaction, in order to improve coupling to carriers:

In the first method, reductive amination of oxidised sialic acid residue side chains is used, but the aldehyde groups are first aminated, and then the amine is coupled to a carrier via a linker. This method is illustrated in 'route A' of FIG. 2.

In the second method, sialic acid residues and/or N-acetylglucosamine residues are de-N-acetylated to give amine groups, and the amine groups are coupled to a carrier protein via a linker. This method is illustrated in 'route B' of FIG. 2.

In the third method, linkage is via galactose residues in the capsular saccharide rather than sialic acid residues. This method avoids disrupting key epitopes formed by sialic acid residues.

In a first aspect, therefore, the invention provides a process for preparing a conjugate of a *S. agalactiae* capsular saccharide and a carrier molecule, comprising the steps of: (a) oxidising a *S. agalactiae* capsular saccharide in order to introduce an aldehyde group into at least one terminal sialic acid residue in the saccharide; (b) subjecting the aldehyde group to reductive amination with ammonia or a primary amine, to give a —$CH_2$—linked amine; (c) reacting the —$CH_2$—linked amine with a bifunctional linker, to give an activated saccharide; and (d) reacting the activated saccharide with a carrier molecule, thereby giving the conjugate. The invention also provides a conjugate, wherein the conjugate comprises a *S. agalactiae* capsular saccharide moiety joined to a carrier via a linker moiety, and wherein the linker moiety is attached to a sialic acid residue in the capsular saccharide moiety.

In a second aspect, the invention provides a process for preparing a conjugate of a *S. agalactiae* capsular saccharide and a carrier molecule, comprising the steps of: (a) de-N-acetylating the capsular saccharide, to give a de-N-acetylated saccharide; (b) reacting the de-N-acetylated saccharide with a bifunctional linker, to give an activated saccharide; and (c) reacting the activated saccharide with a carrier molecule, thereby giving the conjugate. Between steps (a) and (b), the process may involve a step of partial re-N-acetylation of the saccharide.

In a third aspect, the invention provides a process for preparing a conjugate of a capsular saccharide and a carrier molecule, comprising the steps of: (a) oxidising a capsular saccharide in order to introduce an aldehyde group into at least one galactose residue in the saccharide, to give a modified galactose residue; and (b) coupling the modified galactose residue to a carrier molecule. The coupling in step (b) may be direct, or may be via a linker molecule. The invention also provides a conjugate, wherein the conjugate comprises a capsular saccharide moiety joined to a carrier via a linker moiety, and wherein the linker moiety is attached to a galactose residue in the capsular saccharide moiety. Oxidation of galactose residues is particularly useful for conjugation of *S. agalactiae* capsular saccharides, but is also suitable for use with other bacteria that have galactose-containing capsular saccharides e.g. in *Neisseria meningitidis* (serogroup W135), *Vibrio cholerae* (including O139), *Klebsiella pneumoniae* (including K21), *Escherichia coli* (including K52), *Streptococcus pneumoniae* (including type 18C), etc. This process can also be used with galactose-containing lipopolysaccharides and lipooligosaccharides. It is particularly useful where the galactose is a terminal residue of the saccharide.

The Capsular Saccharide

The invention is based on the capsular saccharide of *Streptococcus agalactiae*. The capsular polysaccharide is covalently linked to the peptidoglycan backbone of GBS, and is distinct from the group B antigen, which is another saccharide that is attached to the peptidoglycan backbone.

The GBS capsular polysaccharides are chemically related, but are antigenically very different. All GBS capsular polysaccharides share the following trisaccharide core:

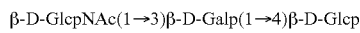

The various GBS serotypes differ by the way in which this core is modified. The difference between serotypes Ia and III, for instance, arises from the use of either the GlcNAc (Ia) or the Gal (III) in this core for linking consecutive trisaccharide cores (FIG. 4). Serotypes Ia and Ib both have a [α-D-NeupNAc(2→3)β-D-Galp-(1→] disaccharide linked to the GlcNAc in the core, but the linkage is either 1→4 (Ia) or 1→3 (Ib).

GBS-related disease arises primarily from serotypes Ia, Ib, II, III, IV, V, VI, VII, and VIII, with over 90% being caused by five serotypes: Ia, Ib, II, III & V. The invention preferably uses a saccharide from one of these five serotypes. As shown in FIG. 3, the capsular saccharides of each of these five serotypes include: (a) a terminal N-acetyl-neuraminic acid (NeuNAc) residue (commonly referred to as sialic acid), which in all cases is linked 2→3 to a galactose residue; and (b) a N-acetyl-glucosamine residue (GlcNAc) within the trisaccharide core.

All five saccharides include galactose residues within the trisaccharide core, but serotypes Ia, Ib, II & III also contain additional galactose residues in each repeating unit, with the serotype II saccharide containing three galactose residues per repeating unit. In the third aspect of the invention, the galactose residues involved in the conjugation reactions may be a residue in the trisaccharide core or a residue outside the trisaccharide core. Where a single saccharide molecule is linked to multiple carrier molecules, it is preferred that the linkages involve the same-positioned galactose in the various linked repeating units, but it is also possible to link to differently-positioned galactose residues in different repeating units.

Saccharides used according to the invention may be in their native form, or may have been modified. For example, the saccharide may be shorter than the native capsular saccharide, or may be chemically modified.

Thus the saccharide used according to the invention may be a substantially full-length capsular polysaccharide, as found in nature, or it may be shorter than the natural length. Full-length polysaccharides may be depolymerised to give shorter fragments for use with the invention e.g. by hydrolysis in mild acid, by heating, by sizing chromatography, etc. Chain length has been reported to affect immunogenicity of GBS saccharides in rabbits [4]

Depolymerisation of the serotype III capsular saccharide by endo-β-galactosidase has been reported [refs. 1 & 4-6], including using the depolymerised material to form conjugates with a tetanus toxoid carrier. Ozonolysis of capsular polysaccharides from GBS serotypes II, III and VIII has also been used for depolymerisation [12]. It is preferred to use saccharides with MW>30 kDa, and substantially full-length capsular polysaccharides can be used. For serotype Ia, it is preferred to use polysaccharides with a MW up to ~145 kDa. For serotype Ib, it is preferred to use polysaccharides with a MW up to ~50 kDa. For serotype III, it is preferred to use polysaccharides with a MW up to ~50 kDa. These molecular masses can be measured by gel filtration relative to dextran standards, such as those available from Polymer Standard Service [13].

The saccharide may be chemically modified relative to the capsular saccharide as found in nature. For example, the saccharide may be de-O-acetylated (partially or fully), de-N-acetylated (partially or fully), N-propionated (partially or fully), etc. De-acetylation may occur before, during or after conjugation, but preferably occurs before conjugation. Depending on the particular saccharide, de-acetylation may or may not affect immunogenicity e.g. the NeisVac-C™ vaccine uses a de-O-acetylated saccharide, whereas Menjugate™ is acetylated, but both vaccines are effective. The relevance of O-acetylation on GBS saccharides in various serotypes is discussed in reference 14, and it is preferred to retain O-acetylation of sialic acid residues at positions 7, 8 and/or 9 before during and after conjugation e.g. by protection/de-protection, by re-acetylation, etc. The effect of de-acetylation etc. can be assessed by routine assays.

Capsular saccharides can be purified by known techniques, as described in the references herein. A typical process involves base extraction, centrifugation, filtration, RNase/DNase treatment, protease treatment, concentration, size exclusion chromatography, ultrafiltration, anion exchange chromatography, and further ultrafiltration. Treatment of GBS cells with the enzyme mutanolysin, which cleaves the bacterial cell wall to free the cell wall components, is also useful.

As an alternative, the purification process described in reference 15 can be used. This involves base extraction, ethanol/$CaCl_2$ treatment, CTAB precipitation, and re-solubilisation.

The invention is not limited to saccharides purified from natural sources, however, and the saccharides may be obtained by other methods, such as total or partial synthesis.

The Carrier

The invention involves the use of carrier molecules, which are typically proteins. In general, covalent conjugation of saccharides to carriers enhances the immunogenicity of saccharides as it converts them from T-independent antigens to T-dependent antigens, thus allowing priming for immunological memory. Conjugation is particularly useful for paediatric vaccines [e.g. ref. 16] and is a well known technique [e.g. reviewed in refs. 17 to 25].

Preferred carrier proteins are bacterial toxins or toxoids, such as diphtheria toxoid or tetanus toxoid. The CRM197 mutant of diphtheria toxin [26-28] is a particularly preferred carrier for, as is a diphtheria toxoid. Other suitable carrier proteins include the N. Meningitidis outer membrane protein [29], synthetic peptides [30,31], heat shock proteins [32,33], pertussis proteins [34,35], cytokines [36], lymphokines [36], hormones [36], growth factors [36], human serum albumin (preferably recombinant), artificial proteins comprising multiple human $CD4^+$ T cell epitopes from various pathogen-derived antigens [37] such as N19 [38], protein D from H. influenzae [39,40], pneumococcal surface protein PspA [41], pneumolysin [42], iron-uptake proteins [43], toxin A or B from C. difficile [44], a GBS protein (see below; particularly GBS67) [195], etc.

Attachment to the carrier is preferably via a —$NH_2$ group e.g. in the side chain of a lysine residue in a carrier protein, or of an arginine residue. Where a saccharide has a free aldehyde group then this can react with an amine in the carrier to form a conjugate by reductive amination. The third aspect of the invention may be based on reductive amination involving an oxidised galactose in the saccharide (from which an aldehyde is formed) and an amine in the carrier or in the linker. Attachment may also be via a —SH group e.g. in the side chain of a cysteine residue.

It is possible to use more than one carrier protein e.g. to reduce the risk of carrier suppression. Thus different carrier proteins can be used for different GBS serotypes e.g. serotype Ia saccharides might be conjugated to CRM197 while serotype Ib saccharides might be conjugated to tetanus toxoid. It is also possible to use more than one carrier protein for a particular saccharide antigen e.g. serotype III saccharides might be in two groups, with some conjugated to CRM197 and others conjugated to tetanus toxoid. In general, however, it is preferred to use the same carrier protein for all saccharides.

A single carrier protein might carry more than one saccharide antigen [45,46]. For example, a single carrier protein might have conjugated to it saccharides from serotypes Ia and Ib. To achieve this goal, different saccharides can be mixed prior to the conjugation reaction. In general, however, it is preferred to have separate conjugates for each serogroup, with the different saccharides being mixed after conjugation. The separate conjugates may be based on the same carrier.

Conjugates with a saccharide:protein ratio (w/w) of between 1:5 (i.e. excess protein) and 5:1 (i.e. excess saccharide) are preferred. Ratios between 1:2 and 5:1 are preferred, as are ratios between 1:1.25 and 1:2.5. Ratios between 1:1 and 4:1 are also preferred. With longer saccharide chains, a weight excess of saccharide is typical. As shown in the examples, a weight ratio between 1:1 and 4:1, and particularly 1:1 and 3:1, can readily be achieved. In general, the invention provides a conjugate, wherein the conjugate comprises a S. agalactiae capsular saccharide moiety joined to a carrier, wherein the weight ratio of saccharide:carrier is at least 2:1.

Compositions may include a small amount of free carrier [47]. When a given carrier protein is present in both free and conjugated form in a composition of the invention, the unconjugated form is preferably no more than 5% of the total amount of the carrier protein in the composition as a whole, and more preferably present at less than 2% by weight.

After conjugation, free and conjugated saccharides can be separated. There are many suitable methods, including hydrophobic chromatography, tangential ultrafiltration, diafiltration etc. [see also refs. 48 & 49, etc.].

Where the composition of the invention includes a depolymerised oligosaccharide, it is preferred that depolymerisation precedes conjugation.

Introduction of Aldehyde Groups

The first aspect of the invention involves oxidation of sialic acid to form an aldehyde, and the third aspect involves oxidation of galactose to form an aldehyde. The aldehyde can then be used for reactions such as reductive amination.

Oxidation of hydroxyls to give aldehydes can be achieved chemically or enzymatically. These reactions will typically take place in aqueous conditions.

Methods for oxidation of sialic acids in GBS saccharides in order to introduce aldehyde groups for reductive amination are known in the art [e.g. ref. 50]. Typical reactions to produce aldehydes in sialic acids include the use of periodate salts, and particularly meta-periodates (e.g. sodium or potassium meta-periodate e.g. NaIO$_4$), to oxidise vicinal hydroxides [10]. Periodate oxidation has been reported for at least serogroups II [3,50], III [2] and V [50]. Other oxidation conditions can be used e.g. use of osmium tetroxide, etc.

In the third aspect of the invention, the —OH that is oxidised is preferably the primary —OH (i.e. not the secondary or anomeric —OH groups), which is attached to C-6. Thus it is preferred to convert galactose into galactohexodialose. This can conveniently be achieved using a galactose oxidase enzyme, from any suitable source (e.g. from *Fusarium* fungi, or *Dactylium dendroides*). The enzyme can be used in recombinant form, or purified from its native source. The galactose oxidase enzyme has EC number 1.1.3.9, and is also known as D-Galactose:oxygen 6-oxidoreductase. The enzyme uses a copper ion cofactor and can be inhibited by cyanide, diethyldithiocarbamate, azide and hydroxylamine, so use of these reagents prior to oxidation is preferably avoided. The pH optimum for the *D. dendroides* is around neutral, which is thus the preferred pH for oxidation. A product of the enzymatic reaction is $H_2O_2$ (reduced oxygen), and the concentration of this product can be controlled e.g. if its presence is damaging to the saccharide.

For both sialic acid and galactose, therefore, the preferred oxidation reactions involve the terminal carbon atoms in the monosaccharides i.e. the highest-numbered carbons by standard nomenclature.

The proportion of monosaccharide subunits in a saccharide chain that are converted to include an aldehyde group can be controlled by varying reaction conditions. For example, reference 50 reports that controlled periodate oxidation of serotype II GBS polysaccharide resulted in the modification of 7% of sialic acid residues as determined by gas chromatography-mass spectrometry analysis, with a higher percentage being seen for serotype V GBS polysaccharide. Reference 2 reports 25% conversion for serotype III. Preliminary studies of reaction conditions (e.g. time, temperature, concentrations, etc.) can be performed to find optimum conditions for any desired end result.

In general, it is typical to introduce aldehyde groups into between 5% and 50% (e.g. 10-40%, preferably between 15%-30%; or between 5% and 20%) of the total sialic acid or galactose monosaccharide units within a saccharide. Higher percentages lead to saccharides that are more difficult to handle, without any corresponding increase in immunogenicity, Reductive Amination In the first aspect of the invention, reductive amination of the new aldehyde group is used to give a group for attachment of the linker. Reductive amination can also be used in the third aspect of the invention after the aldehyde group has been produced, either to attach a linker or for direct linkage to a carrier. Reductive amination is a standard technique in organic chemistry, and has been used extensively in the production of conjugates of capsular saccharides for vaccine use.

In the first aspect, the reductive amination involves either ammonia or a primary amine (NH$_2$R). This can conveniently be achieved by using an ammonium salt (e.g. ammonium chloride) in combination with an appropriate reducing agent (e.g. cyanoborohydrides, such as sodium cyanoborohydride NaBH$_3$CN; borane-pyridine; sodium triacetoxyborohydride; borohydride exchange resin; etc.). The result of reductive amination is that C-8 in the sialic acid carries —NHR rather than =O. This group can then be used for attachment of a bifunctional linker for conjugation.

In the third aspect, the oxidised galactose has an aldehyde group on C-6. This group can be coupled to a bifunctional linker by reductive amination in the same way as described above i.e. involving ammonia or a primary amine. As an alternative, reductive amination can be used to link the aldehyde to a carrier directly, without use of a linker, by utilising an amine group on the carrier.

Reductive amination will generally be carried out in a polar protic solvent, such as water or alcohol.

Bifunctional Linker

The first and second aspects of the invention (and, optionally, the third aspect) involve the use of a bifunctional linker. A bifunctional linker is used to provide a first group for coupling to an amine group in the modified capsular saccharide and a second group for coupling to the carrier (typically for coupling to an amine in the carrier).

The first group in the bifunctional linker is thus able to react with the amine group (—NHR) on the modified sialic acid (or galactose) residue. This reaction will typically involve an electrophilic substitution of the amine's hydrogen. The second group in the bifunctional linker is able to react with the amine group on the carrier. This reaction will again typically involve an electrophilic substitution of the amine. The invention can use both heterobifunctional linkers and homobifunctional linkers.

Where the reactions with both the saccharide and the carrier involve amines then it is preferred to use a bifunctional linker of the formula X-L-X, where: the two X groups are the same as each other and can react with the amines; and where L is a linking moiety in the linker. A preferred X group is N-oxysuccinimide. L preferably has formula -L'-$L^2$-L'-, where L' is carbonyl. Preferred $L^2$ groups are straight chain alkyls with 1 to 10 carbon atoms (e.g. $C_1$, $C_2$, $C_3$, $C_4$, $C_5$, $C_6$, $C_7$, $C_8$, $C_9$, $C_{10}$) e.g. —$(CH_2)_4$—. A preferred linker is thus adipic acid N-hydroxysuccinimide diester (SIDEA):

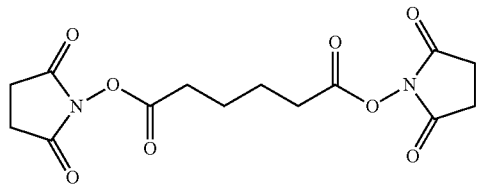 [SMILES: O=C(CCCCC(=O)ON1C(=O)CCC1=O)ON1C(=O)CCC1=O]

Other X groups are those which form esters when combined with HO-L-OH, such as norborane, p-nitrobenzoic acid, and sulfo-N-hydroxysuccinimide.

Further bifunctional linkers reactive with amines for use with the invention include acryloyl halides (e.g. chloride) [54], haloacylhalides [55], disuccinimidyl glutarate, disuccinimidyl suberate, ethylene glycol bis[succinimidylsuccinate], etc.

The linker will generally be added in molar excess to modified saccharide.

The linker/saccharide reaction will generally take place in an aprotic solvent (e.g. DMSO, ethanol acetate, etc.), as the linkers are typically insoluble in water. Where water-soluble linkers are used, however, then a wider range of solvents is available, including protic solvents such as water. Suitable linkers include sulphonated forms, such as sulphonated SIDEA:

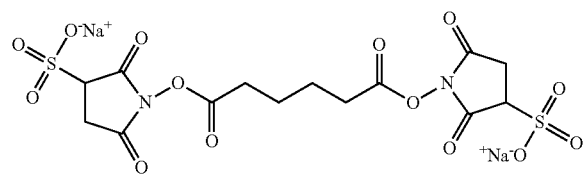

De-N-acetylation and re-N-acetylation

The sialic acid residues in GBS capsular saccharides are N-acetylated, as are the glucosamine residues within the trisaccharide core. Whereas the first aspect of the invention introduces amine groups in at C-8 of the sialic acid via an aldehyde intermediate, the second aspect of the invention uses amine groups produced by de-N-acetylation of the sialic acid and/or N-acetyl-glucosamine residues. The reaction schemes for amines produced in this way are generally the same as described for the first aspect of the invention.

De-N-acetylation of GBS saccharides can conveniently be achieved by treating the saccharide with a base. As GBS saccharides can be purified by a process involving base extraction [51] then de-N-acetylation may be a side-reaction during purification.

Because N-acetyl groups may be part of important epitopes in GBS saccharides, complete de-N-acetylation may not be desirable, but this process is difficult to control. If the extent of de-N-acetylation is greater than desired, therefore, the invention may involve a step of controlled re-N-acetylation. Re—N-acetylation can conveniently be performed using a reagent such as acetic anhydride $(CH_3CO)_2O$ e.g. in 5% ammonium bicarbonate [52]. Rather than use re-N-acetylation, however, the inventors have found that base extraction of the saccharide from bacteria can, if performed quickly enough without prolonged storage of the saccharide, give a saccharide with less than 25% de-N-acetylation.

The result of de-N-acetylation and optional re-N-acetylation is a saccharide in which at least 1 sialic acid residue or glucosamine is de-N-acetylated. Typically, at least 60% of the sialic acid residues and glucosamine residues in the GBS saccharide are N-acetylated e.g. ≥70%, ≥75%, ≥80%, ≥85%, ≥90%, etc. The remaining de-N-acetylated groups (i.e. —$NH_2$ groups) can be used for conjugation in the same way as described for the first aspect of the invention, except that the —NH— in the final conjugate will be derived from the original saccharide rather than being added during the conjugation reaction.

These de- and re-acetylation reactions can be performed in aqueous conditions.

In embodiments of the first and third aspects of the invention where the aldehyde is reductively aminated, it is preferred that the saccharide is substantially totally re-N-acetylated prior to the reductive amination (preferably prior to oxidation of galactose in the third aspect), in order to avoid the presence of free amine groups on sialic acids that would otherwise offer alternative linking groups to the aminated aldehyde.

The Conjugate

Conjugates of the invention are formed by mixing the modified GBS saccharide with the carrier under suitable reaction conditions. In general, two types of conjugate can be made, as shown in FIG. 5: (a) a conjugate where an individual saccharide is attached to a single carrier e.g. through its reducing terminus; and (b) a conjugate where an individual saccharide is attached to multiple carriers e.g. because several monosaccharide subunits are reactive. In both situations a single carrier protein can link to multiple saccharide molecules because it can have multiple exposed lysine side chains.

Conjugates of type (b) are more typical in the present invention, because the modified sialic acid or galactose residues of the invention occur at multiple sites along a single saccharide [50]. In preferred conjugates of the invention, therefore, a single saccharide molecule is coupled on average to more than one carrier molecule.

In the first and third methods of the invention, where oxidised saccharides are used for conjugation, the number of carrier molecules attached to a saccharide will depend on the number of free aldehyde groups that are present. As mentioned above, it is preferred that 5-50% of sialic acid (first method) or galactose (third method) residues in the saccharide are oxidised.

In the first and second aspects of the invention (and optionally in the third) the conjugates will include a linker moiety. This linker moiety originates neither in the saccharide nor the carrier, but is a third molecule used during conjugate preparation, and can readily be distinguished from both the saccharide and carrier protein in a final conjugate product.

The linker moiety may include atoms such as carbon, hydrogen, oxygen and/or nitrogen. Linkers that comprise carbon and hydrogen are preferred, and linkers that further comprise oxygen and/or nitrogen are also preferred. Linkers that include nitrogen atoms may include a carbon atom bonded to a nitrogen atom, which in turn is bonded to a second carbon atom (—C—N—C—). Linkers that include an oxygen atom preferably include it as part of a carbonyl group. Linker moieties with a molecular weight of between 30-500 Da are preferred. Linkers containing two carbonyl groups are preferred.

A particularly preferred linker moiety is —NH—C(O)—$(CH_2)_n$—C(O)—, wherein n is 1, 2, 3, 4, 5, 6, 7, 8, 9 or 10. The value of n is preferably 4. The terminal —NH— in this linker is preferably attached to a carbon atom from the saccharide moiety. The terminal —C(O)— is preferably attached to a nitrogen atom in an amino acid side chain in the carrier. The preferred linker moiety can conveniently be introduced by a process involving: reductive amination of an aldehyde in an oxidised sialic acid; reaction of the resulting —$NH_2$ group with a bifunctional linker that is a diester (e.g. a disuccinimidyl ester) of a dioic acid (e.g. of adipic acid, HOOC—$(CH_2)_4$—COOH); and reductive amination of the product (see FIG. 6).

Other chemistries that can be used to attach a linker to a terminal —$NH_2$ in a saccharide, which may have been introduced (as in the first aspect of the invention) or may be part of a de-N-acetylated monosaccharide residue (as in the second aspect of the invention), include:

acryloylation (e.g. by reaction with acryloyl chloride), followed by Michael-type addition to either the $\epsilon$-$NH_2$ of an amino acid side chain or to a —SH of a cysteine side chain [54]. The resulting linker is —NH—C(O)—$(CH_2)_2$— (propionamido), as shown in FIG. 8, or —C(O)—$(CH_2)_2$— if an existing —$NH_2$ takes part in the reaction.

reaction with a haloacylhalide, followed by reaction with the $\epsilon$-$NH_2$ of an amino acid side chain or to a —SH of a cysteine side chain [55]. The linker is —NH—C(O)—$CH_2$— (as shown in FIG. 9) or —C(O)—$CH_2$—, depending on whether an existing or added —$NH_2$ takes part in the reaction.

Another preferred linker moiety is —C(O)—$(CH_2)_n$—C(O)—, wherein n is 1, 2, 3, 4, 5, 6, 7, 8, 9 or 10. The value of n is preferably 4. One terminal —C(O)— in this linker is preferably attached to a nitrogen carbon atom from the saccharide moiety, and the other terminal —C(O)— is preferably attached to a nitrogen atom in an amino acid side chain in the carrier. The preferred linker moiety can conveniently be introduced by a process involving: reaction of a —$NH_2$ group in a de-N-acetylated monosaccharide unit with a bifunctional linker that is a diester (e.g. a disuccinimidyl ester) of a dioic acid (e.g. of adipic acid, HOOC—$(CH_2)_4$—COOH); and reductive amination of the product (FIG. 7). Other options include conjugating via hydroxyl groups in the saccharide. Hydroxyls can be activated (e.g. by CNBr or CDAP) and then subjected to conjugation.

Combinations of Conjugates and Other Antigens

As well as providing individual conjugates as described above, the invention provides a composition comprising a conjugate of the invention and one or more further antigens.

The further antigen(s) may comprise further conjugates of the invention, and so the invention provides a composition comprising more than one conjugate of the invention. The further antigen(s) may be GBS saccharide conjugates prepared by methods other than those of the invention, and so the invention provides a composition comprising a first GBS saccharide conjugate and a second GBS saccharide conjugate, wherein the first conjugate is a conjugate of the invention and the second conjugate is not a conjugate of the invention.

The different GBS conjugates may include different types of conjugate from the same GBS serotype and/or conjugates from different GBS serotypes. For example, the invention provides a composition comprising conjugates from two or three of serotypes Ia, Ib and III. The composition will be produced by preparing separate conjugates (e.g. a different conjugate for each serotype) and then combining the conjugates.

The further antigen(s) may comprise GBS amino acid sequences, as set out below.

The further antigen(s) may comprise antigens from non-GBS pathogens. Thus the compositions of the invention may further comprise one or more non-GBS antigens, including additional bacterial, viral or parasitic antigens. These may be selected from the following:

a protein antigen from *N. meningitidis* serogroup B, such as those in refs. 56 to 62, with protein '287' (see below) and derivatives (e.g. 'ΔG287') being particularly preferred.

an outer-membrane vesicle (OMV) preparation from *N. meningitidis* serogroup B, such as those disclosed in refs. 63, 64, 65, 66 etc.

a saccharide antigen from *N. meningitidis* serogroup A, C, W135 and/or Y, such as the oligosaccharide disclosed in ref. 67 from serogroup C or the oligosaccharides of ref 68.

a saccharide antigen from *Streptococcus pneumoniae* [e.g. refs. 69-71; chapters 22 & 23 of ref. 78].

an antigen from hepatitis A virus, such as inactivated virus [e.g. 72, 73; chapter 15 of ref. 78].

an antigen from hepatitis B virus, such as the surface and/or core antigens [e.g. 73,74; chpater 16 of ref. 78].

an antigen from hepatitis C virus [e.g. 75], an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 76 & 77; chapter 21 of ref. 78].

a diphtheria antigen, such as a diphtheria toxoid [e.g. chapter 13 of ref. 78].

a tetanus antigen, such as a tetanus toxoid [e.g. chapter 27 of ref. 78].

a saccharide antigen from *Haemophilus influenzae* B [e.g. chapter 14 of ref. 78]

an antigen from *N. gonorrhoeae* [e.g. 56, 57, 58].

an antigen from *Chlamydia pneumoniae* [e.g. 79, 80, 81, 82, 83, 84, 85].

an antigen from *Chlamydia trachomatis* [e.g. 86].

an antigen from *Porphyromonas gingivalis* [e.g. 87].

polio antigen(s) [e.g. 88, 89; chapter 24 of ref. 78] such as IPV.

rabies antigen(s) [e.g. 90] such as lyophilised inactivated virus [e.g.91, RabAvert™].

measles, mumps and/or rubella antigens [e.g. chapters 19, 20 and 26 of ref. 78].

influenza antigen(s) [e.g. chapters 17 & 18 of ref. 78], such as the haemagglutinin and/or neuraminidase surface proteins.

an antigen from *Moraxella catarrhalis* [e.g. 92].

an antigen from *Streptococcus pyogenes* (group A *streptococcus*) [e.g. 93, 94, 95].

an antigen from *Staphylococcus aureus* [e.g. 96].

Where a saccharide or carbohydrate antigen is used, it is preferably conjugated to a carrier in order to enhance immunogenicity. Conjugation of *H. influenzae* B, meningococcal and pneumococcal saccharide antigens is well known.

Toxic protein antigens may be detoxified where necessary (e.g. detoxification of pertussis toxin by chemical and/or genetic means [77]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens.

Antigens may be adsorbed to an aluminium salt.

One type of preferred composition includes further antigens from sexually-transmitted pathogens, such as: herpesvirus; *N. gonorrhoeae*; papillomavirus; *C. trachomatis*; etc. Another type of preferred composition includes further antigens that affect the elderly and/or the immunocompromised, and so the GBS antigens of the invention can be combined with one or more antigens from the following non-GBS pathogens: influenza virus, *Enterococcus faecalis, Staphylococcus aureus, Staphylococcus epidermis, Pseudomonas aeruginosa, Legionella pneumophila, Listeria monocytogenes, Neisseria meningitidis*, and parainfluenza virus.

Antigens in the composition will typically be present at a concentration of at least 1 μg/ml each. In general, the concentration of any given antigen will be sufficient to elicit an immune response against that antigen.

As an alternative to using proteins antigens in the composition of the invention, nucleic acid encoding the antigen may be used [e.g. refs. 97 to 105]. Protein components of the compositions of the invention may thus be replaced by nucleic acid (preferably DNA e.g. in the form of a plasmid) that encodes the protein.

In practical terms, there may be an upper limit to the number of antigens included in compositions of the invention. The number of antigens (including GBS antigens) in a composition of the invention may be less than 20, less than 19, less than 18, less than 17, less than 16, less than 15, less than 14, less than 13, less than 12, less than 11, less than 10, less than 9, less than 8, less than 7, less than 6, less than 5, less than 4, or less than 3. The number of GBS antigens in a composition of the invention may be less than 6, less than 5, or less than 4.

Pharmaceutical Compositions and Methods

The invention provides a pharmaceutical composition comprising (a) a conjugate of the invention and (b) a pharmaceutically acceptable carrier. Typical 'pharmaceutically acceptable carriers' include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose [106], trehalose [107], lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable excipients is available in reference 108.

Compositions of the invention may be in aqueous form (i.e. solutions or suspensions) or in a dried form (e.g. lyophilised). If a dried vaccine is used then it will be reconstituted into a liquid medium prior to injection. Lyophilisation of conjugate vaccines is known in the art e.g. the Menjugate™ product is presented in lyophilised form, whereas NeisVac-C™ and Meningitec™ are presented in aqueous form. To stabilise conjugates during lyophilisation, it may be preferred to include a sugar alcohol (e.g. mannitol) or a disaccharide (e.g. sucrose or trehalose) e.g. at between 1 mg/ml and 30 mg/ml (e.g. about 25 mg/ml) in the composition.

Compositions may be presented in vials, or they may be presented in ready-filled syringes. The syringes may be supplied with or without needles. A syringe will include a single dose of the composition, whereas a vial may include a single dose or multiple doses.

Aqueous compositions of the invention are also suitable for reconstituting other vaccines from a lyophilised form. Where a composition of the invention is to be used for such extemporaneous reconstitution, the invention provides a kit, which may comprise two vials, or may comprise one ready-filled syringe and one vial, with the contents of the syringe being used to reactivate the contents of the vial prior to injection.

Compositions of the invention may be packaged in unit dose form or in multiple dose form. For multiple dose forms; vials are preferred to pre-filled syringes. Effective dosage volumes can be routinely established, but a typical human dose of the composition has a volume of 0.5 ml e.g. for intramuscular injection.

The pH of the composition is preferably between 6 and 8, preferably about 7. Stable pH may be maintained by the use of a buffer. If a composition comprises an aluminium hydroxide salt, it is preferred to use a histidine buffer [109]. The composition may be sterile and/or pyrogen-free. Compositions of the invention may be isotonic with respect to humans.

Compositions of the invention are immunogenic, and are more preferably vaccine compositions. Vaccines according to the invention may either be prophylactic (i.e. to prevent infection) or therapeutic (i.e. to treat infection), but will typically be prophylactic. Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

Within each dose, the quantity of an individual saccharide antigen will generally be between 1-50 μg (measured as mass of saccharide) e.g. about 1 μg, about 2.5 μg, about 4 μg, about 5 μg, or about 10 μg.

GBS affects various areas of the body and so the compositions of the invention may be prepared in various forms. For example, the compositions may be prepared as injectables, either as liquid solutions or suspensions. The composition may be prepared for pulmonary administration e.g. as an inhaler, using a fine powder or a spray. The composition may be prepared as a suppository or pessary. The composition may be prepared for nasal, aural or ocular administration e.g. as spray, drops, gel or powder [e.g. refs 110 & 111]. Success with nasal administration of pneumococcal saccharides [112, 113], Hib saccharides [114], MenC saccharides [115], and mixtures of Hib and MenC saccharide conjugates [116] has been reported.

Compositions of the invention may include an antimicrobial, particularly when packaged in multiple dose format.

Compositions of the invention may comprise detergent e.g. a Tween (polysorbate), such as Tween 80. Detergents are generally present at low levels e.g. <0.01%.

Compositions of the invention may include sodium salts (e.g. sodium chloride) to give tonicity. A concentration of 10±2 mg/ml NaCl is typical.

Compositions of the invention will generally include a buffer. A phosphate buffer is typical.

Compositions of the invention will generally be administered in conjunction with other immunoregulatory agents. In particular, compositions will usually include one or more adjuvants. Such adjuvants include, but are not limited to:

A. Mineral-Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref. 117], or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being preferred. The mineral containing compositions may also be formulated as a particle of metal salt [118].

Aluminum salts may be included in vaccines of the invention such that the dose of $Al^{3+}$ is between 0.2 and 1.0 mg per dose.

A typical aluminium phosphate adjuvant is amorphous aluminium hydroxyphosphate with $PO_4/Al$ molar ratio between 0.84 and 0.92, included at 0.6 mg $Al^{3+}$/ml. Adsorption with a low dose of aluminium phosphate may be used e.g. between 50 and 100 µg $Al^{3+}$ per conjugate per dose. Where an aluminium phosphate it used and it is desired not to adsorb an antigen to the adjuvant, this is favoured by including free phosphate ions in solution (e.g. by the use of a phosphate buffer).

B. Oil Emulsions

Oil emulsion compositions suitable for use as adjuvants in the invention include squalene-water emulsions, such as MF59 (5% Squalene, 0.5% Tween 80, and 0.5% Span 85, formulated into submicron particles using a microfluidizer) [Chapter 10 of ref. 117; see also refs. 119-121]. MF59 is used as the adjuvant in the FLUAD™ influenza virus trivalent subunit vaccine.

Particularly preferred adjuvants for use in the compositions are submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v Tween 80 (polyoxyelthylenesorbitan monooleate), and/or 0.25-1.0% Span 85 (sorbitan trioleate), and, optionally, N-acetylmuramyl-L-alanyl-D-isogluatminyl-L-alanine-2-(1'-2'-dipalmitoyl-sn-glycero-3-hydroxyphosphosphoryloxy)-ethylamine (MTP-PE). Submicron oil-in-water emulsions, methods of making the same and immunostimulating agents, such as muramyl peptides, for use in the compositions, are described in detail in references 119 & 122-123. Complete Freund's adjuvant (CFA) and incomplete Freund's adjuvant (IFA) may also be used as adjuvants in the invention.

C. Saponin Formulations [Chapter 22 of Ref 117]

Saponin formulations may also be used as adjuvants in the invention. Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 124. Saponin formulations may also comprise a sterol, such as cholesterol [125].

Combinations of saponins and cholesterols can be used to form unique particles called immunostimulating complexs (ISCOMs) [chapter 23 of ref. 117]. ISCOMs typically also include a phospholipid such as phosphatidylethanolamine or phosphatidylcholine. Any known saponin can be used in ISCOMs. Preferably, the ISCOM includes one or more of QuilA, QHA and QHC. ISCOMs are further described in refs. 125-127. Optionally, the ISCOMS may be devoid of additional detergent(s) [128].

A review of the development of saponin based adjuvants can be found in refs. 129 & 130.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 131-136. Virosomes are discussed further in, for example, ref. 137

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof. Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 138. Such "small particles" of 3dMPL are small enough to be sterile filtered through a 0.22 µm membrane [138]. Other non-toxic LPS derivatives include monophosphoryl lipid A mimics, such as aminoalkyl glucosaminide phosphate derivatives e.g. RC-529 [139,140].

Lipid A derivatives include derivatives of lipid A from *Escherichia coli* such as OM-174. OM-174 is described for example in refs. 141 & 142.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 143, 144 and 145 disclose possible analog substitutions e.g. replacement of guanosine with 2'-deoxy-7-deazaguanosine. The adjuvant effect of CpG oligonucleotides is further discussed in refs. 146-151.

The CpG sequence may be directed to TLR9, such as the motif GTCGTT or TTCGTT [152]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 153-155. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 152 & 156-158.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 159 and as parenteral adjuvants in ref. 160. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivaties thereof, particularly LT-K63 and LT-R72, as adjuvants can be found in refs. 161-168. Numerical reference for amino acid substitutions is preferably based on the alignments of the A and B subunits of ADP-ribosylating toxins set forth in ref. 169, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 [170], etc.) [171], interferons (e.g. interferon-γ), macrophage colony stimulating factor, and tumor necrosis factor.

G. Bioadhesives and Mucoadhesives

Bioadhesives and mucoadhesives may also be used as adjuvants in the invention. Suitable bioadhesives include esterified hyaluronic acid microspheres [172] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [173].

H. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of Ref 117)

Examples of liposome formulations suitable for use as adjuvants are described in refs. 174-176.

J. Polyoxyethylene Ether and Polyoxyethylene Ester Formulations

Adjuvants suitable for use in the invention include polyoxyethylene ethers and polyoxyethylene esters [177]. Such formulations further include polyoxyethylene sorbitan ester surfactants in combination with an octoxynol [178] as well as polyoxyethylene alkyl ethers or ester surfactants in combination with at least one additional non-ionic surfactant such as an octoxynol [179]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Polyphosphazene (PCPP)

PCPP formulations are described, for example, in refs. 180 and 181.

L. Muramyl peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds.

Examples of imidazoquinolone compounds suitable for use adjuvants in the invention include Imiquamod and its homologues (e.g. "Resiquimod 3M"), described further in refs. 182 and 183.

N. Thiosemicarbazone Compounds.

Examples of thiosemicarbazone compounds, as well as methods of formulating, manufacturing, and screening for compounds all suitable for use as adjuvants in the invention include those described in ref. 184. The thiosemicarbazones are particularly effective in the stimulation of human peripheral blood mononuclear cells for the production of cytokines, such as TNF-α.

O. Tryptanthrin Compounds.

Examples of tryptanthrin compounds, as well as methods of formulating, manufacturing, and screening for compounds all suitable for use as adjuvants in the invention include those described in ref. 185. The tryptanthrin compounds are particularly effective in the stimulation of human peripheral blood mononuclear cells for the production of cytokines, such as TNF-α.

The invention may also comprise combinations of aspects of one or more of the adjuvants identified above. For example, the following combinations may be used as adjuvant compositions in the invention: (1) a saponin and an oil-in-water emulsion [186]; (2) a saponin (e.g. QS21)+a non-toxic LPS derivative (e.g. 3dMPL) [187]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [188]; (5) combinations of 3dMPL with, for example, QS21 and/or oil-in-water emulsions [189]; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+

CWS (Detox™); and (8) one or more mineral salts (such as an aluminum salt)+a non-toxic derivative of LPS (such as 3dMPL).

Other substances that act as immunostimulating agents are disclosed in chapter 7 of ref. 117.

The use of aluminium salt adjuvants is particularly preferred, and antigens are generally adsorbed to such salts. The Menjugate™ and NeisVac™ conjugates use a hydroxide adjuvant, whereas Meningitec™ uses a phosphate adjuvant. It is possible in compositions of the invention to adsorb some antigens to an aluminium hydroxide but to have other antigens in association with an aluminium phosphate. In general, however, it is preferred to use only a single salt e.g. a hydroxide or a phosphate, but not both. Not all conjugates need to be adsorbed i.e. some or all can be free in solution.

Methods of Treatment

The invention also provides a method for raising an immune response in a mammal, comprising administering a pharmaceutical composition of the invention to the mammal. The immune response is preferably protective and preferably involves antibodies. The method may raise a booster response.

The mammal is preferably a human. Where the vaccine is for prophylactic use, the human is preferably a child (e.g. a toddler or infant) or a teenager; where the vaccine is for therapeutic use, the human is preferably an adult. A vaccine intended for children may also be administered to adults e.g. to assess safety, dosage, immunogenicity, etc. A preferred class of humans for treatment are females of child-bearing age (e.g. teenagers and above). Another preferred class is pregnant females.

The invention also provides a composition of the invention for use as a medicament. The medicament is preferably able to raise an immune response in a mammal (i.e. it is an immunogenic composition) and is more preferably a vaccine.

The invention also provides the use of a conjugate of the invention in the manufacture of a medicament for raising an immune response in a mammal.

These uses and methods are preferably for the prevention and/or treatment of a disease caused by S. agalactiae e.g. neonatal sepsis or bacteremia, neonatal pneumonia, neonatal meningitis, endometritis, osteomyelitis, septic arthritis, etc.

The subject in which disease is prevented may not be the same as the subject that receives the conjugate of the invention. For instance, a conjugate may be administered to a female (before or during pregnancy) in order to protect offspring (so-called 'maternal immunisation' [190-192]).

One way of checking efficacy of therapeutic treatment involves monitoring GBS infection after administration of the composition of the invention. One way of checking efficacy of prophylactic treatment involves monitoring immune responses against the GBS antigens after administration of the composition.

Preferred compositions of the invention can confer an antibody titre in a patient that is superior to the criterion for seroprotection for each antigenic component for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is 0.5 ml.

The invention may be used to elicit systemic and/or mucosal immunity.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

GBS Protein Antigens

As mentioned above, GBS proteins can be included in compositions of the invention. These may be used as carrier proteins for conjugates of the invention, carrier proteins for other conjugates, or as unconjugated protein antigens.

GBS protein antigens for use with the invention include those disclosed in references 93 and 193-195. Five preferred GBS protein antigens for use with the invention are known as: GBS67; GBS80; GBS104; GBS276; and GBS322 [see ref. 93]. Further details of these five antigens are given below.

The full-length sequences for these five GBS proteins are SEQ ID NOs 1 to 5 herein. Compositions of the invention may thus include (a) a polypeptide comprising an amino acid sequence selected from SEQ ID NOs 1 to 5, and/or (b) a polypeptide comprising (i) an amino acid sequence that has sequence identity to one or more of SEQ ID NOs 1 to 5 and/or (ii) a fragment of SEQ ID NOs 1 to 5.

Depending on the particular SEQ ID NO, the degree of sequence identity in (i) is preferably greater than 50% (e.g. 60%, 70%, 75%, 80%, 85%, 90%, 91%, 92%, 93%, 94%, 95%, 96%, 97%, 98%, 99% or more). These polypeptides include homologs, orthologs, allelic variants and functional mutants. Typically, 50% identity or more between two polypeptide sequences is considered to be an indication of functional equivalence. Identity between polypeptides is preferably determined by the Smith-Waterman homology search algorithm as implemented in the MPSRCH program (Oxford Molecular), using an affine gap search with parameters gap open penalty=12 and gap extension penalty=1.

Depending on the particular SEQ ID NO, the fragments of (ii) should comprise at least n consecutive amino acids from the sequences and, depending on the particular sequence, n is 7 or more (e.g. 8, 10, 12, 14, 16, 18, 20, 22, 24, 26, 28, 30, 35, 40, 45, 50, 60, 70, 80, 90, 100 or more). The fragment may comprise at least one T-cell or, preferably, a B-cell epitope of the sequence. T- and B-cell epitopes can be identified empirically (e.g. using PEPSCAN [196,197] or similar methods), or they can be predicted (e.g. using the Jameson-Wolf antigenic index [198], matrix-based approaches [199], TEPITOPE [200], neural networks [201], OptiMer & EpiMer [202, 203], ADEPT [204], Tsites [205], hydrophilicity [206], antigenic index [207] or the methods disclosed in reference 208 etc.). Other preferred fragments are SEQ ID NOs 1 to 5 without their N-terminal amino acid residue or without their N-terminal signal peptide. Removal of one or more domains, such as a leader or signal sequence region, a transmembrane region, a cytoplasmic region or a cell wall anchoring motif can be used. Preferred fragments are given below (SEQ ID NOs 6 to 19).

These polypeptide may, compared to SEQ ID NOs 1 to 5, include one or more (e.g. 1, 2, 3, 4, 5, 6, 7, 8, 9, 10, etc.) conservative amino acid replacements i.e. replacements of one amino acid with another which has a related side chain. Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cystine, serine, threonine, tyrosine. Phenylalanine, tryptophan, and tyrosine are sometimes classified jointly as aromatic amino acids. In general, substitution of single amino acids within these families does not have a major effect on the biological activity. The polypeptides may also include one or more (e.g. 1, 2, 3, 4, 5, 6, 7, 8, 9, 10, etc.) single amino acid deletions relative to SEQ ID NOs 1 to 5. The polypeptides may also include one or more (e.g. 1, 2, 3, 4, 5, 6, 7, 8, 9, 10, etc.) insertions (e.g. each of 1, 2, 3, 4 or 5 amino acids) relative to the SEQ ID NOs 1 to 5.

Polypeptides of the invention can be prepared in many ways e.g. by chemical synthesis (in whole or in part), by digesting longer polypeptides using proteases, by translation from RNA, by purification from cell culture (e.g. from recombinant expression), from the organism itself (e.g. after bacterial culture, or direct from patients), etc. A preferred method for production of peptides <40 amino acids long involves in vitro chemical synthesis [209,210]. Solid-phase peptide synthesis is particularly preferred, such as methods based on tBoc or Fmoc [211] chemistry. Enzymatic synthesis [212] may also be used in part or in full. As an alternative to chemical synthesis, biological synthesis may be used e.g. the polypeptides may be produced by translation. This may be carried out in vitro or in vivo. Biological methods are in general restricted to the production of polypeptides based on L-amino acids, but manipulation of translation machinery (e.g. of aminoacyl tRNA molecules) can be used to allow the introduction of D-amino acids (or of other non natural amino acids, such as iodotyrosine or methylphenylalanine, azidohomoalanine, etc.) [213]. Where D-amino acids are included, however, it is preferred to use chemical synthesis. Polypeptides of the invention may have covalent modifications at the C-terminus and/or N-terminus.

If these GBS proteins are included in compositions of the invention then they can take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.). They are preferably used in purified or substantially purified form i.e. substantially free from other polypeptides (e.g. free from naturally-occurring polypeptides), particularly from other GBS or host cell polypeptides).

GBS67

Nucleotide and amino acid sequence of GBS67 sequenced from serotype V strain 2603 V/R are set forth in ref. 93 as SEQ ID NOs 3745 & 3746. The amino acid sequence is SEQ ID NO:1 herein:

MRKYQKFSKILTLSLFCLSQIPLNTNVLGESTVPENGAKGKLVVKKTDDQ

NKPLSKATFVLKTTAHPESKIEKVTAELTGEATFDNLIPGDYTLSEETAP

EGYKKTNQTWQVKVESNGKTTIQNSGDKNSTIGQNQEELDKQYPPTGIYE

DTKESYKLEHVKGSVPNGKSEAKAVNPYSSEGEHIREIPEGTLSKRISEV

GDLAHNKYKIELTVSGKTIVKPVDKQKPLDVVFVLDNSNSMNNDGPNFQR

HNKAKKAAEALGTAVKDILGANSDNRVALVTYGSDIFDGRSVDVVKGFKE

DDKYYGLQTKFTIQTENYSHKQLTNNAEEIIKRIPTEAPKAKWGSTTNGL

TPEQQKEYYLSKVGETFTMKAFMEADDILSQVNRNSQKIIVHVTDGVPTR

SYAINNFKLGASYESQFEQMKKNGYLNKSNFLLTDKPEDIKGNGESYFLF

PLDSYQTQIISGNLQKLHYLDLNLNYPKGTIYRNGPVKEHGTPTKLYINS

LKQKNYDIFNFGIDISGFRQVYNEEYKKNQDGTFQKLKEEAFKLSDGEIT

ELMRSFSSKPEYYTPIVTSADTSNNEILSKIQQQFETILTKENSIVNGTI

EDPMGDKINLQLGNGQTLQPSDYTLQGNDGSVMKDGIATGGPNNDGGILK

GVKLEYIGNKLYVRGLNLGEGQKVTLTYDVKLDDSFISNKFYDTNGRTTL

NPKSEDPNTLRDFPIPKIRDVREYPTITIKNEKKLGEIEFIKVDKDNNKL

LLKGATFELQEFNEDYKLYLPIKNNNSKVVTGENGKISYKDLKDGKYQLI

EAVSPEDYQKITNKPILTFEVVKGSIKNIIAVNKQISEYHEEGDKHLITN

THIPPKGI*IPMTGGKGILS*<u>FILIGGAMMSIAGGIYI</u>WKRYKKSSDMSIKK

D

GBS67 contains a C-terminus transmembrane region which is indicated by the underlined region closest to the C-terminus of SEQ ID NO: 1 above. One or more amino acids from the transmembrane region may be removed, or the amino acid may be truncated before the transmembrane region. An example of such a GBS67 fragment is set forth below as SEQ ID NO: 18.

MRKYQKFSKILTLSLFCLSQIPLNTNVLGESTVPENGAKGKLVVKKTDDQ

NKPLSKATFVLKTTAHPESKIEKVTAELTGEATFDNLIPGDYTLSEETAP

EGYKKTNQTWQVKVESNGKTTIQNSGDKNSTIGQNQEELDKQYPPTGIYE

DTKESYKLEHVKGSVPNGKSEAKAVNPYSSEGEHIRETPEGTLSKRISEV

GDLAHNKYKIELTVSGKTIVKPVDKQKPLDVVFVLDNSNSMNNDGPNFQR

HNKAKKAAEALGTAVKDILGANSDNRVALVTYGSDIFDGRSVDVVKGFKE

DDKYYGLQTKFTIQTENYSHKQLTNNAEEIIKRIPTEAPKAKWGSTTNGL

TPEQQKEYYLSKVGETFTMKAFMEADDILSQVNRNSQKIIVHVTDGVPTR

SYAINNFKLGASYESQFEQMKKNGYLNKSNFLLTDKPEDIKGNGESYFLF

PLDSYQTQIISGNLQKLHYLDLNLNYPKGTIYRNGPVKEHGTPTKLYINS

LKQKNYDIFNFGIDISGFRQVYNEEYKKNQDGTFQKLKEEAFKLSDGEIT

ELMRSFSSKPEYYTPIVTSADTSNNEILSKIQQQFETILTKENSIVNGTI

EDPMGDKINLQLGNGQTLQPSDYTLQGNDGSVMKDGIATGGPNNDGGILK

GVKLEYIGNKLYVRGLNLGEGQKVTLTYDVKLDDSFISNKFYDTNGRTTL

NPKSEDPNTLRDFPIPKIRDVREYPTITIKNEKKLGEIEFIKVDKDNNKL

LLKGATFELQEFNEDYKLYLPIKNNNSKVVTGENGKISYKDLKDGKYQLI

EAVSPEDYQKITNKPILTFEVVKGSIKNIIAVNKQISEYHEEGDKHLITN

THIPPKGIIPMTGGKGILS

GBS67 contains an amino acid motif indicative of a cell wall anchor, shown in italics in SEQ ID NO: 1 above. In some recombinant host cell systems, it may be preferable to remove this motif to facilitate secretion of a recombinant GBS67 protein from the host cell. Accordingly, in one preferred fragment of GBS67 for use in the invention, the transmembrane and the cell wall anchor motif are removed from GBS67. An example of such a GBS67 fragment is set forth below as SEQ ID NO: 19.

MRKYQKFSKILTLSLFCLSQIPLNTNVLGESTVPENGAKGKLVVKKTDDQ
NKPLSKATFVLKTTAHPESKIEKVTAELTGEATEDNLIPGDYTLSEETAP
EGYKKTNQTWQVKVESNGKTTIQNSGDKNSTIGQNQEELDKQYPPTGIYE
DTKESYKLEHVKGSVPNGKSEAKAVNPYSSEGEHIREIPEGTLSKRISEV
GDLAHNKYKIELTVSGKTIVKPVDKQKPLDVVFVLDNSNSMNNDGPNFQR
HNKAKKAAEALGTAVKDILGANSDNRVALVTYGSDIFDGRSVDVVKGFKE
DDKYYGLQTKFTIQTENYSHKQLTNNAEEIIKRIPTEAPKAKWGSTTNGL
TPEQQKEYYLSKVGETFTMKAFMEADDILSQVNRNSQKIIVHVTDGVPTR
SYAINNFKLGASYESQFEQMKKNGYLNKSNFLLTDKPEDIKGNGESYFLF
PLDSYQTQIISGNLQKLHYLDLNLNYPKGTIYRNGPVKEHGTPTKLYINS
LKQKNYDIFNFGIDISGFRQVYNEEYKKNQDGTFQKLKEEAFKLSDGEIT
ELMRSFSSKPEYYTPIVTSADTSNNEILSKIQQQFETILTKENSIVNGTI
EDPMGDKINLQLGNGQTLQPSDYTLQGNDGSVMKDGIATGGPNNDGGILK
GVKLEYIGNKLYVRGLNLGEGQKVTLTYDVKLDDSFISNKFYDTNGRTTL
NPKSEDPNTLRDFPIPKIRDVREYPTITIKNEKKLGEIEFIKVDKDNNKL
LLKGATFELQEFNEDYKLYLPIKNNNSKVVTGENGKISYKDLKDGKYQLI
EAVSPEDYQKITNKPILTFEVVKGSIKNIIAVNKQISEYHEEGDKHLITN
THIPPKGI

MKLSKKLLFSAAVLTMVAGSTVEPVAQFATGMSIVRAAEVSQERPAKTTV
NIYKLQADSYKSEITSNGGIENKDGEVISNYAKLGDNVKGLQGVQFKRYK
VKTDISVDELKKLTTVEAADAKVGTILEEGVSLPQKTNAQGLVVDALDSK
SNVRYLYVEDLKNSPSNITKAYAVPFVLELPVANSTGTGFLSEINIYPKN
VVTDEPKTDKDVKKLGQDDAGYTIGEEFKWFLKSTIPANLGDYEKFEITD
KFADGLTYKSVGKIKIGSKTLNRDEHYTIDEPTVDNQNTLKITFKPEKFK
EIAELLKGMTLVKNQDALDKATANTDDAAFLEIPVASTINEKAVLGKAIE
NTFELQYDHTPDKADNPKPSNPPRKPEVHTGGKRFVKKDSTETQTLGGAE
FDLLASDGTAVKWTDALIKANTNKNYIAGEAVTGQPIKLKSHTDGTFEIK
GLAYAVDANAEGTAVTYKLKETKAPEGYVIPDKEIEFTVSQTSYNTKPTD
ITVDSADATPDTIKNNKRPS*IPNTG*GIGTAIFVAIGAAVMAFA VKGMKRR
TKDN

GBS80 contains a N-terminal leader or signal sequence region which is indicated by the underlined sequence above. One or more amino acids from the leader or signal sequence region of GBS80 can be removed. An example of such a GBS80 fragment is set forth below as SEQ ID NO: 6:

AEVSQERPAKTTVNIYKLQADSYKSEITSNGGIENKDGEVISNYAKLGDNVKGLQGVQFKRYKVKTDISVDELKKLTTV
EAADAKVGTILEEGVSLPQKTNAQGLVVDALDSKSNVRYLYVEDLKNSPSNITKAYAVPFVLELPVANSTGTGFLSEIN
IYPKNVVTDEPKTDKDVKKLGQDDAGYTIGEEFKWFLKSTIPANLGDYEKFEITDKFADGLTYKSVGKIKIGSKTLNRD
EHYTIDEPTVDNQNTLKITFKPEKFKEIAELLKGMTLVKNQDALDKATANTDDAAFLEIPVASTINEKAVLGKAIENTF
ELQYDHTPDKADNPKPSNPPRKPEVHTGGKRFVKKDSTETQTLGGAEFDLLASDGTAVKWTDALIKANTNKNYIAGEAV
TGQPIKLKSHTDGTFEIKGLAYAVDANAEGTAVTYKLKETKAPEGYVIPDKEIEFTVSQTSYNTKPTDITVDSADATPD
TIKNNKRPSIPNTGGIGTAIFVAIGAAVMAFAVKGMKRRTKDN

GBS80

GBS80 refers to a putative cell wall surface anchor family protein. Nucleotide and amino acid sequence of GBS80 sequenced from serotype V isolated strain 2603 V/R are set forth in ref. 93 as SEQ ID NOs 8779 & 8780. The amino acid sequence is set forth below as SEQ ID NO: 2:

GBS80 contains a C-terminal transmembrane region which is indicated by the underlined sequence near the end of SEQ ID NO: 2 above. One or more amino acids from the transmembrane region and/or a cytoplasmic region may be removed. An example of such a fragment is set forth below as SEQ ID NO:7:

MKLSKKLLFSAAVLTMVAGSTVEPVAQFATGMSIVRAAEVSQERPAKTTVNIYKLQADSYKSEITSNGGIENKDGEVIS
NYAKLGDNVKGLQGVQFKRYKVKTDISVDELKKLTTVEAADAKVGTILEEGVSLPQKTNAQGLVVDALDSKSNVRYLYV
EDLKNSPSNITKAYAVPFVLELPVANSTGTGFLSEINTYPKNVVTDEPKTDKDVKKLGQDDAGYTIGEEFKWFLKSTIP
ANLGDYEKFEITDKFADGLTYKSVGKIKIGSKTLNRDEHYTIDEPTVDNQNTLKITFKPEKFKEIAELLKGMTLVKNQD
ALDKATANTDDAAFLEIPVASTINEKAVLGKAIENTFELQYDHTPDKADNPKPSNPPRKPEVHTGGKRFVKKDSTETQT
LGGAEFDLLASDGTAVKWTDALIKANTNKNYIAGEAVTGQPIKLKSHTDGTFEIKGLAYAVDANAEGTAVTYKLKETKA
PEGYVIPDKEIEFTVSQTSYNTKPTDITVDSADATPDTIKNNKRPS*IPNTG*

GBS80 contains an amino acid motif indicative of a cell wall anchor, shown in italics in SEQ ID NO: 2 above. In some recombinant host cell systems, it may be preferable to remove this motif to facilitate secretion of a recombinant GBS80 protein from the host cell. Thus the transmembrane and/or cytoplasmic regions and the cell wall anchor motif may be removed from GBS80. An example of such a fragment is set forth below as SEQ ID NO: 8.

MKLSKKLLFSAAVLTMVAGSTVEPVAQFATGMSIVRAAEVSQERPAKTTVNIYKLQADSYKSEITSNGGIENKDGEVIS

NYAKLGDNVKGLQGVQFKRYKVKTDISVDELKKLTTVEAADAKVGTILEEGVSLPQKTNAQGLVVDALDSKSNVRYLYV

EDLKNSPSNITKAYAVPFVLELPVANSTGTGFLSEINIYPKNVVTDEPKTDKDVKKLGQDDAGYTIGEEFKWFLKSTIP

ANLGDYEKFEITDKFADGLTYKSVGKIKIGSKTLNRDEHYTIDEPTVDNQNTLKITFKPEKFKEIAELLKGMTLVKNQD

ALDKATANTDDAAFLEIPVASTINEKAVLGKAIENTFELQYDHTPDKADNPKPSNPPRKPEVHTGGKRFVKKDSTETQT

LGGAEFDLLASDGTAVKWTDALIKANTNKNYIAGEAVTGQPIKLKSHTDGTFEIKGLAYAVDANAEGTAVTYKLKETKA

PEGYVIPDKEIEFTVSQTSYNTKPTDITVDSADATPDTIKNNKRPS

Alternatively, in some recombinant host cell systems, it may be preferable to use the cell wall anchor motif to anchor the recombinantly expressed protein to the cell wall. The extracellular domain of the expressed protein may be cleaved during purification or the recombinant protein may be left attached to either inactivated host cells or cell membranes in the final composition.

In one embodiment, the leader or signal sequence region, the transmembrane and cytoplasmic regions and the cell wall anchor motif are removed from the GBS80 sequence. An example of such a GBS80 fragment is set forth below as SEQ ID NO: 9:

AEVSQERPAKTTVNIYKLQADSYKSEITSNGGIENKDGEVISNYAKLGDNVKGLQGVQFKRYKVKTDISVDELKKLTTV

EAADAKVGTILEEGVSLPQKTNAQGLVVDALDSKSNVRYLYVEDLKNSPSNITKAYAVPFVLELPVANSTGTGFLSEIN

IYPKNVVTDEPKTDKDVKKLGQDDAGYTIGEEFKWFLKSTIPANLGDYEKFEITDKFADGLTYKSVGKIKIGSKTLNRD

EHYTIDEPTVDNQNTLKITFKPEKFKEIAELLKGMTLVKNQDALDKATANTDDAAFLEIPVASTINEKAVLGKAIENTF

ELQYDHTPDKADNPKPSNPPRKPEVHTGGKRFVKKDSTETQTLGGAEFDLLASDGTAVKWTDALIKANTNKNYIAGEAV

TGQPIKLKSHTDGTFEIKGLAYAVDANAEGTAVTYKLKETKAPEGYVIPDKEIEFTVSQTSYNTKPTDITVDSADATPD

TIKNNKRPS

A particularly immunogenic fragment of GBS80 is located towards the N-terminus of the protein, and is given herein as SEQ ID NO: 10:

AEVSQERPAKTTVNIYKLQADSYKSEITSNGGIENKDGEVISNYAKLGDNVKGLQGVQFKRYKVKTDISVDELKKLTTV

EAADAKVGTILEEGVSLPQKTNAQGLVVDALDSKSNVRYLYVEDLKNSPSNITKAYAVPFVLELPVANSTGTGFLSEIN

TYPKNVVTDEPKTDKDVKKLGQDDAGYTIGEEFKWFLKSTIPANLGDYEKFEITDKFADGLTYKSVGKIKIGSKTLNRD

EHYTIDEPTVDNQNTLKITFKPEKFKEIAELLKG

GBS104

GBS104 refers to a putative cell wall surface anchor family protein. It has been referred to as emaA. Nucleotide and amino acid sequences of GBS104 sequenced from serotype V isolated strain 2603 V/R are set forth in Ref. 93 as SEQ ID 8777 and SEQ ID 8778. The amino acid sequence is SEQ ID NO: 3 herein:

MKKRQKIWRGLSVTLLILSQIPFGILVQGETQDTNQALGKVIVKKTGDNATPLGKATFVLKNDNDKSETSHETVEGSGE

ATFENIKPGDYTLREETAPIGYKKTDKTWKVKVADNGATIIEGMDADKAEKRKEVLNAQYPKSAIYEDTKENYPLVNVE

GSKVGEQYKALNPINGKDGRREIAEGWLSKKITGVNDLDKNKYKIELTVEGKTTVETKELNQPLDVVVLLDNSNSMNNE

RANNSQRALKAGEAVEKLIDKITSNKDNRVALVTYASTIFDGTEATVSKGVADQNGKALNDSVSWDYHKTTFTATTHNY

SYLNLTNDANEVNILKSRIPKEAEHINGDRTLYQFGATFTQKALMKANEILETQSSNARKKLIFHVTDGVPTMSYAINF

NPYISTSYQNQFNSFLNKIPDRSGILQEDFIINGDDYQIVKGDGESFKLFSDRKVPVTGGTTQAAYRVPQNQLSVMSNE

GYAINSGYIYLYWRDYNWVYPFDPKTKKVSATKQIKTHGEPTTLYFNGNIRPKGYDIFTVGIGVNGDPGATPLEAEKFM

QSISSKTENYTNVDDTNKIYDELNKYFKTIVEEKHSIVDGNVTDPMGEMIEFQLKNGQSFTHDDYVLVGNDGSQLKNGV

ALGGPNSDGGILKDVTVTYDKTSQTIKINHLNLGSGQKVVLTYDVRLKDNYISNKFYNTNNRTTLSPKSEKEPNTIRDF

PIPKIRDVREFPVLTISNQKKMGEVEFIKVNKDKHSESLLGAKFQLQIEKDFSGYKQFVPEGSDVTTKNDGKIYFKALQ

DGNYKLYEISSPDGYIEVKTKPVVTFTIQNGEVTNLKADPNANKNQIGYLEGNGKHLITNTPKRPPGVFPKTGGIGTIV

YILVGSTFMILTICSFRRKQL

GBS104 contains an N-terminal leader or signal sequence region which is indicated by the underlined sequence at the beginning of SEQ ID NO: 3 above. One or more amino acids from the leader or signal sequence region of GBS104 may be removed. An example of such a GBS104 fragment is set forth below as SEQ ID NO 11.

GETQDTNQALGKVIVKKTGDNATPLGKATFVLKNDNDKSETSHETVEGSGEATFENIKPGDYTLREETAPIGYKKTDKT

WKVKVADNGATIIEGMDADKAEKRKEVLNAQYPKSAIYEDTKENYPLVNVEGSKVGEQYKALNPINGKDGRREIAEGWL

SKKITGVNDLDKNKYKIELTVEGKTTVETKELNQPLDVVVLLDNSNSMNNERANNSQRALKAGEAVEKLIDKITSNKDN

RVALVTYASTIFDGTEATVSKGVADQNGKALNDSVSWDYHKTTFTATTHNYSYLNLTNDANEVNILKSRIPKEAEHING

DRTLYQFGATFTQKALMKANEILETQSSNARKKLIFHVTDGVPTMSYAINFNPYISTSYQNQFNSFLNKIPDRSGILQE

DFIINGDDYQIVKGDGESFKLFSDRKVPVTGGTTQAAYRVPQNQLSVMSNEGYAINSGYIYLYWRDYNWVYPFDPKTKK

VSATKQIKTHGEPTTLYFNGNIRPKGYDIFTVGIGVNGDPGATPLEAEKFMQSISSKTENYTNVDDTNKIYDELNKYFK

TIVEEKHSIVDGNVTDPMGEMIEFQLKNGQSFTHDDYVLVGNDGSQLKNGVALGGPNSDGGILKDVTVTYDKTSQTIKI

NHLNLGSGQKVVLTYDVRLKDNYISNKFYNTNNRTTLSPKSEKEPNTIRDFPIPKIRDVREFPVLTISNQKKMGEVEFI

KVNKDKHSESLLGAKFQLQIEKDFSGYKQFVPEGSDVTTKNDGKIYFKALQDGNYKLYEISSPDGYIEVKTKPVVTFTI

QNGEVTNLKADPNANKNQIGYLEGNGKHLITNTPKRPPGVFPKTGGIGTIVYILVGSTFMILTICSFRRKQL

GBS104 contains a C-terminal transmembrane and/or cytoplasmic region which is indicated by the underlined region near the end of SEQ ID NO:3 above. One or more amino acids from the transmembrane or cytoplasmic regions may be removed. An example of such a GBS104 fragment is set forth below as SEQ ID NO 12:

MKKRQKIWRGLSVTLLILSQIPFGILVQGETQDTNQALGKVIVKKTGDNATPLGKATFVLKNDNDKSETSHETVEGSGE

ATFENIKPGDYTLREETAPIGYKKTDKTWKVKVADNGATIIEGMDADKAEKRKEVLNAQYPKSAIYEDTKENYPLVNVE

GSKVGEQYKALNPINGKDGRREIAEGWLSKKITGVNDLDKNKYKIELTVEGKTTVETKELNQPLDVVVLLDNSNSMNNE

RANNSQRALKAGEAVEKLIDKITSNKDNRVALVTYASTIFDGTEATVSKGVADQNGKALNDSVSWDYHKTTFTATTHNY

SYLNLTNDANEVNILKSRIPKEAEHINGDRTLYQFGATFTQKALMKANEILETQSSNARKKLIFHVTDGVPTMSYAINF

NPYISISYQNQFNSFLNKIPDRSGILQEDFIINGDDYQIVKGDGESFKLFSDRKVPVTGGTTQAAYRVPQNQLSVMSNE

GYAINSGYIYLYWRDYNWVYPFDPKTKKVSATKQIKTHGEPTTLYFNGNIRPKGYDIFTVGIGVNGDPGATPLEAEKFM

QSISSKTENYTNVDDTNKIYDELNKYFKTIVEEKHSIVDGNVTDPMGEMIEFQLKNGQSFTHDDYVLVGNDGSQLKNGV

ALGGPNSDGGILKDVTVTYDKTSQTIKINHLNLGSGQKVVLTYDVRLKDNYISNKFYNTNNRTTLSPKSEKEPNTIRDF

PIPKIRDVREFPVLTISNQKKMGEVEFIKVNKDKHSESLLGAKFQLQIEKDFSGYKQFVPEGSDVTTKNDGKIYFKALQ

DGNYKLYEISSPDGYIEVKTKPVVTFTIQNGEVTNLKADPNANKNQIGYLEGNGKHLITNT

One or more amino acids from the leader or signal sequence region and one or more amino acids from the transmembrane or cytoplasmic regions may be removed. An example of such a GBS104 fragment is set forth below as SEQ ID NO 13:

GETQDTNQALGKVIVKKTGDNATPLGKATFVLKNDNDKSETSHETVEGSGEATFENIKPGDYTLREETAPIGYKKTDKT

WKVKVADNGATIIEGMDADKAEKRKEVLNAQYPKSAIYEDTKENYPLVNVEGSKVGEQYKALNPINGKDGRREIAEGWL

SKKITGVNDLDKNKYKIELTVEGKTTVETKELNQPLDVVVLLDNSNSMNNERANNSQRALKAGEAVEKLIDKITSNKDN

RVALVTYASTIFDGTEATVSKGVADQNGKALNDSVSWDYHKTTFTATTHNYSYLNLTNDANEVNILKSRIPKEAEHING

DRTLYQFGATFTQKALMKANEILETQSSNARKKLIFHVTDGVPTMSYAINFNPYISTSYQNQFNSFLNKIPDRSGILQE

DFIINGDDYQIVKGDGESFKLFSDRKVPVTGGTTQAAYRVPQNQLSVMSNEGYAINSGYIYLYWRDYNWVYPFDPKTKK

VSATKQIKTHGEPTTLYFNGNIRPKGYDIFTVGIGVNGDPGATPLEAEKFMQSISSKTENYTNVDDTNKIYDELNKYFK

TIVEEKHSIVDGNVTDPMGEMIEFQLKNGQSFTHDDYVLVGNDGSQLKNGVALGGPNSDGGILKDVTVTYDKTSQTIKI

NHLNLGSGQKVVLTYDVRLKDNYISNKFYNTNNRTTLSPKSEKEPNTIRDFPIPKIRDVREFPVLTISNQKKMGEVEFI

KVNKDKHSESLLGAKFQLQIEKDFSGYKQFVPEGSDVTTKNDGKIYFKALQDGNYKLYEISSPDGYIEVKTKPVVTFTI

QNGEVTNLKADPNANKNQIGYLEGNGKHLITNT

Further fragments of GBS104 include an 830 amino acid fragment of GBS104 of amino acids 28-858 (numbered by SEQ ID NO: 3), a 359 amino acid fragment of GBS104 of amino acids 28-387, a 581 amino acid fragment of GBS104 of amino acids 28-609, or a 740 amino acid fragment of GBS104 of amino acids 28-768.

GBS276

GBS276 refers to a C5a peptidase. Further description of GBS276 can be found in references 214-217. Nucleotide and amino acid sequences of GBS276 sequenced from serotype V isolated strain 2603 V/R are set forth in Ref. 93 as SEQ ID NOs 8941 & 8942. The amino acid sequence is SEQ ID NO: 4 herein:

MRKKQKLPFDKIAIALISTSILLNAQSDIKANTVTEDTPATEQAVEPPQPIAVSEESRSSKETKTSQTPSDVGETVADD

ANDLAPQAPAKTADTPATSKATIRDLNDPSHVKTLQEKAGKGAGTVVAVIDAGFDKNHEAWRLTDKTKARYQSKENLEK

AKKEHGITYGEWVNDKVAYYHDYSKDGKNAVDQEHGTHVSGILSGNAPSEMKEPYRLEGAMPEAQLLLMRVEIVNGLAD

YARNYAQAIRDAVNLGAKVINMSFGNAALAYANLPDETKKAFDYAKSKGVSIVTSAGNDSSFGGKPRLPLADHPDYGVV

GTPAAADSTLTVASYSPDKQLTETATVKTDDHQDKEMPVISTNRFEPNKAYDYAYANRGTKEDDFKDVEGKIALIERGD

IDFKDKIANAKKAGAVGVLIYDNQDKGFPIELPNVDQMPAAFISRRDGLLLKDNPPKTITFNATPKVLPTASGTKLSRF

SSWGLTADGNIKPDIAAPGQDILSSVANNKYAKLSGTSMSAPLVAGIMGLLQKQYETQYPDMTPSERLDLAKKVLMSSA

TALYDEDEKAYFSPRQQGAGAVDAKKASAATMYVTDKDNTSSKVHLNNVSDKFEVTVTVHNKSDKPQELYYQVTVQTDK

VDGKHFALAPKALYETSWQKITIPANSSKQVTVPIDASRFSKDLLAQMKNGYFLEGFVRFKQDPTKEELMSIPYIGFRG

DFGNLSALEKPIYDSKDGSSYYHEANSDAKDQLDGDGLQFYALKNNFTALTTESNPWTIIKAVKEGVENIEDIESSEIT

ETIFAGTFAKQDDDSHYYIHRHANGKPYAAISPNGDGNRDYVQFQGTFLRNAKNLVAEVLDKEGNVVWTSEVTEQVVKN

YNNDLASTLGSTRFEKTRWDGKDKDGKVVANGTYTYRVRYTPISSGAKEQHTDFDVIVDNTTPEVATSATFSTEDSRLT

LASKPKTSQPVYRERIAYTYMDEDLPTTEYTSPNEDGTFTLPEEAETMEGATVPLKMSDFTYVVEDMAGNITYTPVTKL

LEGHSNKPEQDGSDQAPDKKPEAKPEQDGSGQTPDKKKETKPEKDSSGQTPGKTPQKGQSSRTLEKRSSKRALATKAST

RDQLPTTNDKDTNRLHLLKLVMTTFFLG

GBS276 contains an N-terminal leader or signal sequence region which is indicated by the underlined sequence at the beginning of SEQ ID NO: 4 above. One or more amino acids from the leader or signal sequence region of GBS276 may be removed. An example of such a GBS276 fragment is set forth below as SEQ ID NO: 14:

QSDIKANTVTEDTPATEQAVEPPQPIAVSEESRSSKETKTSQTPSDVGETVADDANDLAPQAPAKTADTPATSKATIRD

LNDPSHVKTLQEKAGKGAGTVVAVIDAGFDKNHEAWRLTDKTKARYQSKENLEKAKKEHGITYGEWVNDKVAYYHDYSK

DGKNAVDQEHGTHVSGILSGNAPSEMKEPYRLEGAMPEAQLLLMRVEIVNGLADYARNYAQAIRDAVNLGAKVINMSFG

NAALAYANLPDETKKAFDYAKSKGVSIVTSAGNDSSFGGKPRLPLADHPDYGVVGTPAAADSTLTVASYSPDKQLTETA

TVKTDDHQDKEMPVISTNRFEPNKAYDYAYANRGTKEDDFKDVEGKIALIERGDIDFKDKIANAKKAGAVGVLIYDNQD

KGFPIELPNVDQMPAAFISPRDGLLLKDNPPKTITFNATPKVLPTASGTKLSRFSSWGLTADGNIKPDIAAPGQDILSS

VANNKYAKLSGTSMSAPLVAGIMGLLQKQYETQYPDMTPSERLDLAKKVLMSSATALYDEDEKAYFSPRQQGAGAVDAK

KASAATMYVTDKDNTSSKVHLNNVSDKFEVTVTVHNKSDKPQELYYQVTVQTDKVDGKHFALAPKALYETSWQKITIPA

NSSKQVTVPIDASRFSKDLLAQMKNGYFLEGFVRFKQDPTKEELMSIPYIGFRGDFGNLSALEKPIYDSKDGSSYYHEA

NSDAKDQLDGDGLQFYALKNNFTALTTESNPWTIIKAVKEGVENIEDIESSEITETIFAGTFAKQDDDSHYYIHRHANG

KPYAAISPNGDGNRDYVQFQGTFLRNAKNLVAEVLDKEGNVVWTSEVTEQVVKNYNNDLASTLGSTRFEKTRWDGKDKD

GKVVANGTYTYRVRYTPISSGAKEQHTDFDVIVDNTTPEVATSATFSTEDSRLTLASKPKTSQPVYRERIAYTYMDEDL

PTTEYISPNEDGTFTLPEEAETMEGATVPLKMSDFTYVVEDMAGNITYTPVTKLLEGHSNKPEQDGSDQAPDKKPEAKP

EQDGSGQTPDKKKETKPEKDSSGQTPGKTPQKGQSSRTLEKRSSKRALATKASTRDQLPTTNDKDTNRLHLLKLVMTTF

FLG

GBS276 contains a C-terminal transmembrane and/or cytoplasmic region which is indicated by the underlined sequence near the end of SEQ ID NO: 4 above. One or more amino acids from the transmembrane or cytoplasmic regions of GBS276 may be removed. An example of such a GBS276 fragment is set forth below as SEQ ID NO: 15:

MRKKQKLPFDKLAIALISTSILLNAQSDIKANTVTEDTPATEQAVEPPQPIAVSEESRSSKETKTSQTPSDVGETVADD

ANDLAPQAPAKTADTPATSKATIRDLNDPSHVKTLQEKAGKGAGTVVAVIDAGFDKNHEAWRLTDKTKARYQSKENLEK

AKKEHGITYGEWVNDKVAYYHDYSKDGKNAVDQEHGTHVSGILSGNAPSEMKEPYRLEGAMPEAQLLLMRVEIVNGLAD

YARNYAQAIRDAVNLGAKVINMSFGNAALAYANLPDETKKAFDYAKSKGVSIVTSAGNDSSFGGKPRLPLADHPDYGVV

GTPAAADSTLTVASYSPDKQLTETATVKTDDHQDKEMPVTSTNRFEPNKAYDYAYANRGTKEDDFKDVEGKIALIERGD

IDFKDKIANAKKAGAVGVLIYDNQDKGFPIELPNVDQMPRAFISRRDGLLLKDNPPKTITFNATPKVLPTASGTKLSRF

SSWGLTADGNTKPDIAAPGQDILSSVANNKYAKLSGTSMSAPLVAGIMGLLQKQYETQYPDMTPSERLDLAKKVLMSSA

TALYDEDEKAYFSPRQQGAGAVDAKKASAATMYVTDKDNTSSKVHLNNVSDKFEVTVTVHNKSDKPQELYYQVTVQTDK

VDGKHFALAPKALYETSWQKITIPANSSKQVTVPIDASRFSKDLLAQMKNGYFLEGFVRFKQDPTKEELMSIPYIGFRG

DFGNLSALEKPIYDSKDGSSYYHEANSDAKDQLDGDGLQFYALKNNFTALTTESNPWTIIKAVKEGVENIEDIESSEIT

ETIFAGTFAKQDDDSHYYIHRHANGKPYAAISPNGDGNRDYVQFQGTFLRNAKNLVAEVLDKEGNVVWTSEVTEQVVKN

YNNDLASTLGSTRFEKTRWDGKDKDGKVVANGTYTYRVRYTPISSGAKEQHTDFDVIVDNTTPEVATSATFSTEDSRLT

LASKPKTSQPVYRERIAYTYMDEDLPTTEYISPNEDGTFTLPEEAETMEGATVPLKMSDFTYVVEDMAGNITYTPVTKL

LEGHSNKPEQDGSDQAPDKKPEAKPEQDGSGQTPDKKKETKPEKDSSGQTPGKTPQKGQSSRTLEKRSSKRALATK
                               35

One or more amino acids from the leader or signal sequence region and one or more amino acids from the transmembrane or cytoplasmic regions of GBS276 may be removed. An example of such a GBS276 fragment is set forth below as SEQ ID NO: 16:

QSDIKANTVTEDTPATEQAVEPPQPIAVSEESRSSKETKTSQTPSDVGETVADDANDLAPQAPAKTADTPATSKATIRD

LNDPSHVKTLQEKAGKGAGTVVAVIDAGFDKNHEAWRLTDKTKARYQSKENLEKAKKEHGITYGEWVNDKVAYYHDYSK

DGKNAVDQEHGTHVSGILSGNAPSEMKEPYRLEGAMPEAQLLLMRVEIVNGLADYARNYAQAIRDAVNLGAKVINMSFG

NAALAYANLPDETKKAFDYAKSKGVSIVTSAGNDSSFGGKPRLPLADHPDYGVVGTPAAADSTLTVASYSPDKQLTETA

TVKTDDHQDKEMPVISTNRFEPNKAYDYAYANRGTKEDDFKDVEGKIALIERGDIDFKDKIANAKKAGAVGVLIYDNQD

KGFPIELPNVDQMPAAFISRRDGLLLKDNPPKTITFNATPKVLPTASGTKLSRFSSWGLTADGNIKPDIAAPGQDILSS

VANNKYAKLSGTSMSAPLVAGIMGLLQKQYETQYPDMTPSERLDLAKKVLMSSATALYDEDEKAYFSPRQQGAGAVDAK

KASAATMYVTDKDNTSSKVHLNNVSDKFEVTVTVHNKSDKPQELYYQVTVQTDRVDGKHFALAPKALYETSWQKITIPA

NSSKQVTVPIDASRFSKDLLAQMKNGYFLEGFVRFKQDPTKEELMSIPYIGFRGDFGNLSALEKPIYDSKDGSSYYHEA

NSDAKDQLDGDGLQFYALKNNFTALTTESNPWTIIKAVKEGVENIEDIESSEITETIFAGTFAKQDDDSHYYIHRHANG

KPYAAISPNGDGNRDYVQFQGTFLRNAKNLVAEVLDKEGNVVWTSEVTEQVVKNYNNDLASTLGSTRFEKTRWDGKDKD

GKVVANGTYTYRVRYTPISSGAKEQHTDFDVIVDNTTPEVATSATFSTEDSRLTLASKPKTSQPVYRERIRYTYMDEDL

PTTEYISPNEDGTFTLPEEAETMEGATVPLKMSDFTYVVEDMAGNITYTPVTKLLEGHSNKPEQDGSDQAPDKKPEAKP

EQDGSGQTPDKKKETKPEKDSSGQTPGKTPQKGQSSRTLEKRSSKRALATK

GBS322.

GBS322 refers to a surface immunogenic protein, also referred to as 'sip'. Nucleotide and amino acid sequences of GBS322 sequenced from serotype V isolated strain 2603 V/R are set forth in Ref. 93 as SEQ ID NOs 8539 & 8540. The amino acid sequence is SEQ ID NO: 5 herein:

MNKKVLLTSTMAASLLSVASVQAQETDTTWTARTVSEVKADLVKQDNKSSYTVKYGDTLSVISEAMSIDMNVLAKINNI

ADINLIYPETTLTVTYDQKSHTATSMKIETPATNAAGQTTATVDLKTNQVSVADQKVSLNTISEGMTPEAATTIVSPMK

TYSSAPALKSKEVLAQEQAVSQAAANEQVSPAPVKSITSEVPAAKEEVKPTQTSVSQSTTVSPASVAAETPAPVAKVAP

VRTVAAPRVASVKVVTPKVETGASPEHVSAPAVPVTTTSPATDSKLQATEVKSVPVAQKAPTATPVAQPASTTNAVAAH

PENAGLQPHVAAYKEKVASTYGVNEFSTYRAGDPGDHGKGLAVDFIVGTNQALGNKVAQYSTQNMAANNISYVIWQQKF

YSNTNSIYGPANTWNAMPDRGGVTANHYDHVHVSFNK

GBS322 contains a N-terminal leader or signal sequence region which is indicated by the underlined sequence near the beginning of SEQ ID NO: 5. One or more amino acids from the leader or signal sequence region of GBS322 may be removed. An example of such a GBS322 fragment is set forth below as SEQ ID NO: 17:

DLVKQDNKSSYTVKYGDTLSVISEAMSIDMNVLAKINNIADINLIYPETTLTVTYDQKSHTATSMKIETPATNAAGQTT

ATVDLKTNQVSVADQKVSLNTISEGMTPEAATTIVSPMKTYSSAPALKSKEVLAQEQAVSQAAANEQVSPAPVKSITSE

VPAAKEEVKPTQTSVSQSTTVSPASVAAETPAPVAKVAPVRTVAAPRVASVKVVTPKVETGASPEHVSAPAVPVTTTSP

ATDSKLQATEVKSVPVAQKAPTATPVAQPASTTNAVAAHPENAGLQPHVRAYKEKVASTYGVNEFSTYRAGDPGDHGKG

LAVDFIVGTNQALGNKVAQYSTQNMAANNISYVIWQQKFYSNTNSIYGPANTWNAMPDRGGVTANHYDHVHVSFNK

General

The term "comprising" encompasses "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

Where the invention provides a process involving multiple sequential steps, the invention can also provide a process involving less than the total number of steps. In the first aspect of the invention, for instance, the invention provides a process comprising the steps of: (a) oxidising a GBS capsular saccharide in order to introduce an aldehyde group into a terminal sialic acid residue; and (b) subjecting the aldehyde group to reductive amination. The further steps (c) and (d) need not be performed in order to fall within the scope of the invention, as the product of steps (a) and (b) has utility as an intermediate in conjugate preparation, and may be used, stored, exported, etc. for separate and later use e.g. in steps (c) and (d).

Similarly, where a starting saccharide material is already partially processed then the invention encompasses processes involving only the later steps of a method. In the third aspect of the invention, for instance, the invention encompasses a process comprising a step of coupling a modified galactose residue to a carrier molecule, in which the starting material for the process is a saccharide that was previously oxidised to introduce an aldehyde group into a galactose residue.

These different steps can be performed at very different times by different people in different places (e.g. in different countries).

It will be appreciated that sugar rings can exist in open and closed form and that, whilst closed forms are shown in structural formulae herein, open forms are also encompassed by the invention. Similarly, it will be appreciated that sugars can exist in pyranose and furanose forms and that, whilst pyranose forms are shown in structural formulae herein, furanose forms are also encompassed. Different anomeric forms of sugars are also encompassed.

A primary amine can be represented by formula $NH_2R$. The R group will preferably be electron donating, and includes $C_{1-8}$hydrocarbyl, more preferably $C_{1-8}$alkyl, especially methyl. R is preferably —$CH_3$, —$C_2H_5$ or —$C_3H_7$. The hydrocarbyl may be substituted with one or more groups, such as: halogen (e.g. Cl, Br, F, I), trihalomethyl, $NO_2$, —CN, —$N^+$ $(C_{1-6}alkyl)_2O^-$, —$SO_3H$, —$SOC_{1-6}alkyl$, —$SO_2C_{1-6}$alkyl, $SO_3C_{1-6}alkyl$, —$OC(=O)OC_{1-6}alkyl$, —$C(=O)H$, $C(=O)C_{1-6}alkyl$, $OC(=O)C_{1-6}alkyl$, —$N(C_{1-6}alkyl)_2$, $C_{1-6}alkyl$, —$N(C_{1-6}alkyl)_2$, $C(=O)N(C_{1-6}alkyl)_2$, —$N(C_{1-6}alkyl)C(=O)O(C_{1-6}alkyl)$, —$N(C_{1-6}alkyl)C(=O)N(C_{1-6}alkyl)_2$, $CO_2H$, —$OC(=O)N(C_{1-6}alkyl)_2$, —$N(C_{1-6}alkyl)C(=O)C_{1-6}alkyl$, $N(C_{1-6}alkyl)C(=S)C_{1-6}alkyl$, —$N(C_{1-6}alkyl)SO_2N(C_{1-6}alkyl)_2$, —$CO_2C_{1-6}alkyl$, —$SO_2N(C_{1-6}alkyl)_2$, —$C(=O)NH_2$, —$C(=S)N(C_{1-6}alkyl)_2$, —$N(C_{1-6}alkyl)SO_2C_{1-6}alkyl$, —$N(C_{1-6}alkyl)C(=S)N(C_{1-6}alkyl)_2$, —NH—$C_{1-6}alkyl$, —S—$C_{1-6}alkyl$ or —O—$C_{1-6}alkyl$. The term 'hydrocarbyl' includes linear, branched or cyclic monovalent groups consisting of carbon and hydrogen. Hydrocarbyl groups thus include alkyl, alkenyl and alkynyl groups, cycloalkyl (including polycycloalkyl), cycloalkenyl and aryl groups and combinations thereof, e.g. alkylcyloalkyl, alkylpolycycloalkyl, alkylaryl, alkenylaryl, cycloalkylaryl, cycloalkenylaryl, cycloalkylalkyl, polycycloalkylalkyl, arylalkyl, lalkenyl, arylcycloalkyl and arylcycloalkenyl groups. Preferred hydrocarbyl are CJ.J4 hydrocarbyl, more preferably $C_{1-8}$ hydrocarbyl.

BRIEF DESCRIPTION OF DRAWINGS

FIG. 3 shows the repeating structures of capsular saccharides in GBS serotypes Ia, Ib, II, III & V.

FIG. 5A, example of a conjugate in which an individual saccharide is attached to a single carrier. FIG. 5B, example of a conjugate in which an individual saccharide is attached to multiple carriers.

MODES FOR CARRYING OUT THE INVENTION

Conjugate Production and Characterisation

Figure 1:
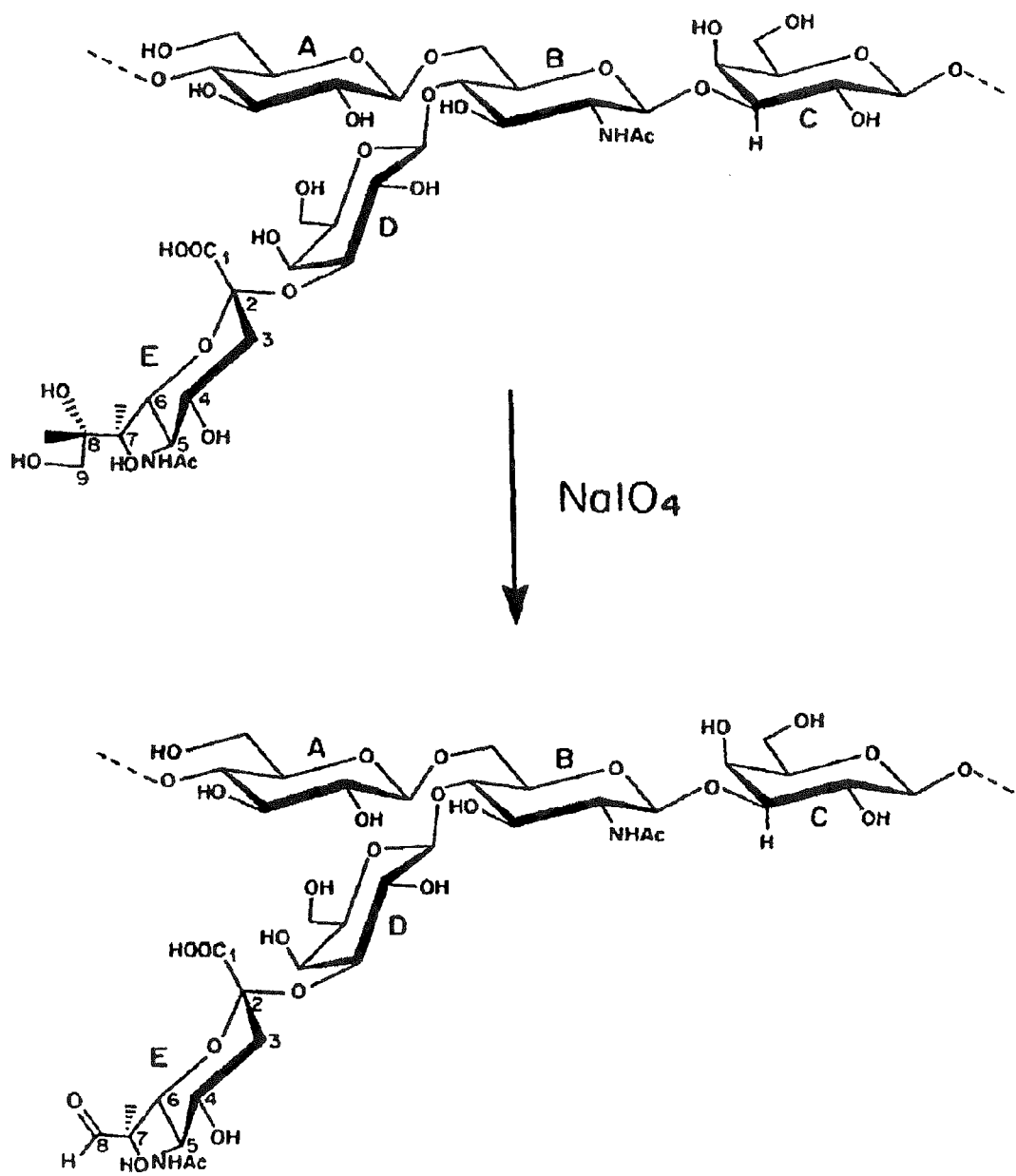
FIG. 1 shows periodate oxidation of a terminal sialic acid residue.
Figure 2:
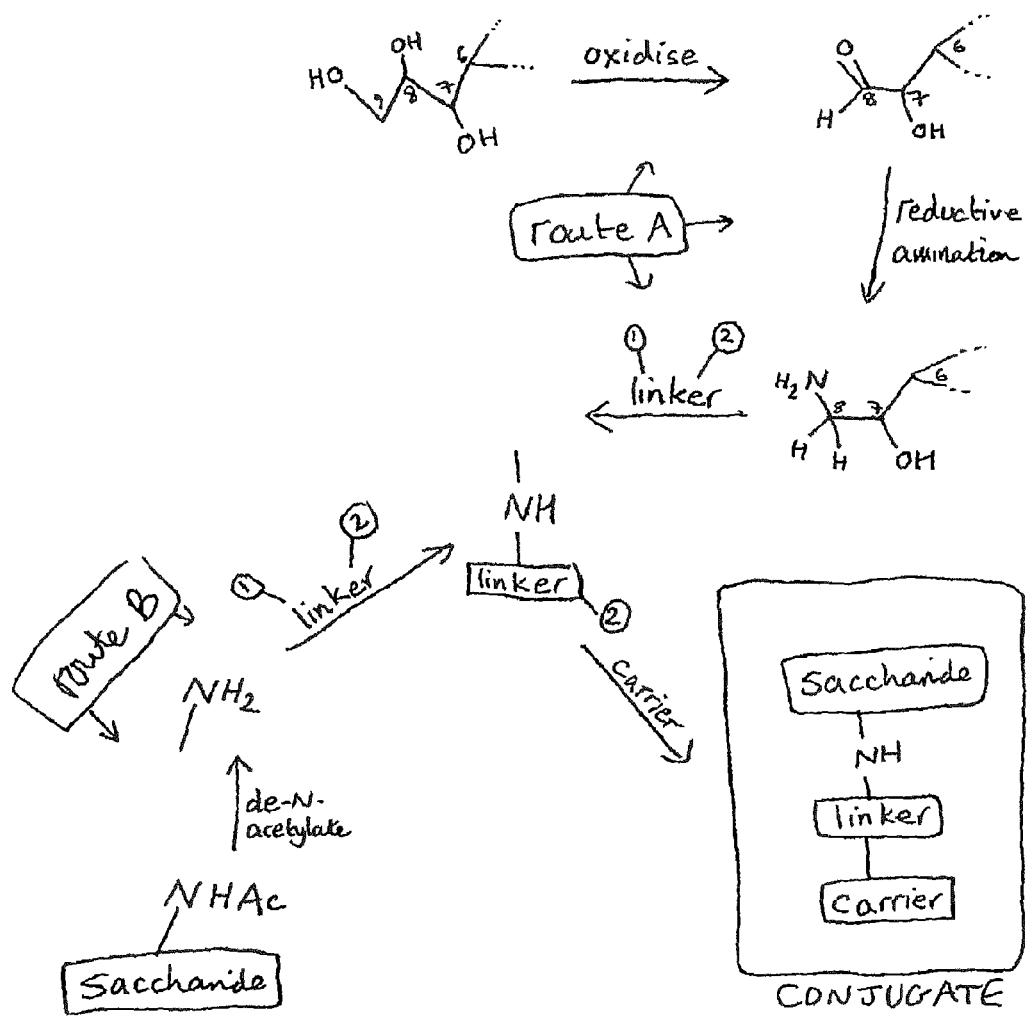
FIG. 2 illustrates the first (route A) and second (route B) aspects of the invention. The numbers at either end of the linkers designate a first group ("1") for coupling to an amine group in the modified capsular saccharide and a second group ("2") for coupling to the carrier. Numbering in the chemical structures refers to the identifying numbers of the depicted carbon atoms.
Figure 4:
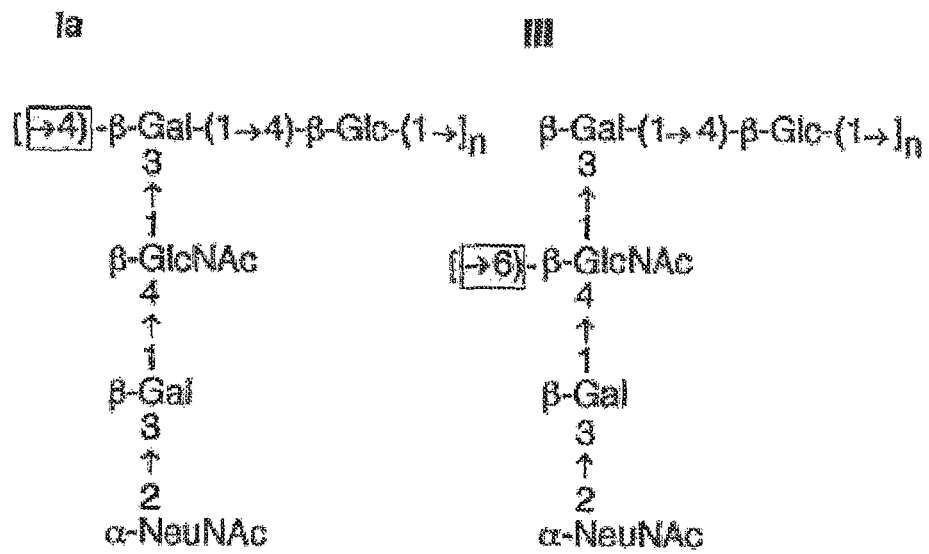
FIG. 4 shows the difference between the repeating structures in GBS serotypes Ia and III.
Figure 5:
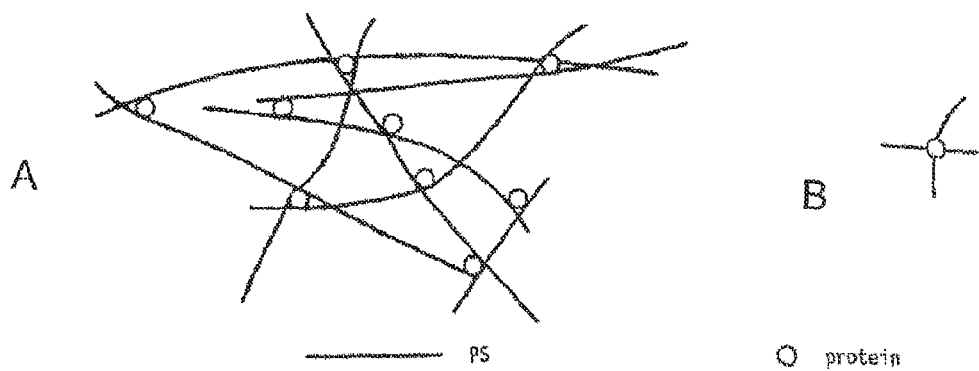
FIGS. 5A-B show two types of conjugate that can be prepared.
Figure 6:
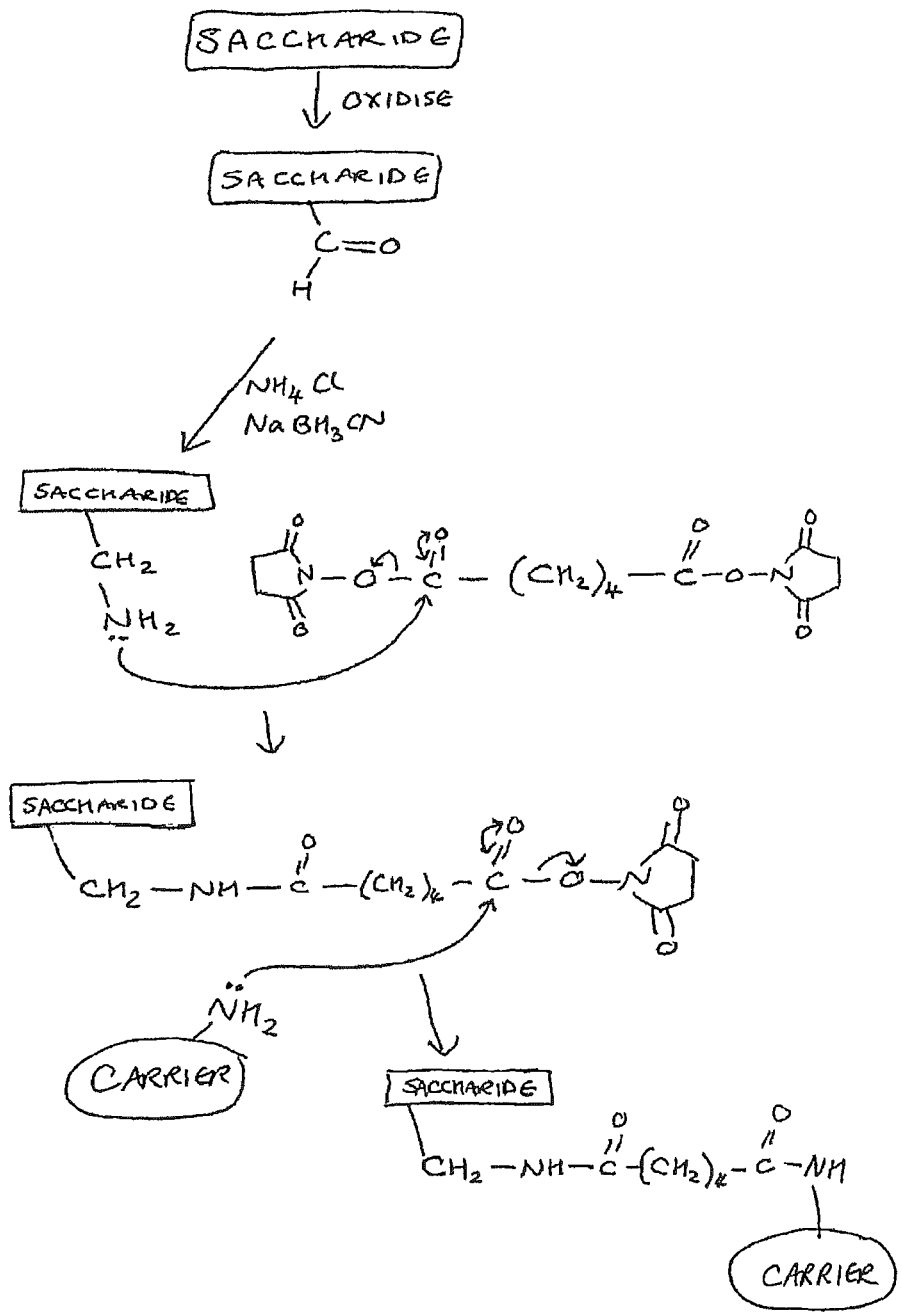
FIG. 6 shows a preferred conjugation reaction using the succinimidyl diester of adipic acid, according to the first aspect of the invention.
Figure 7:
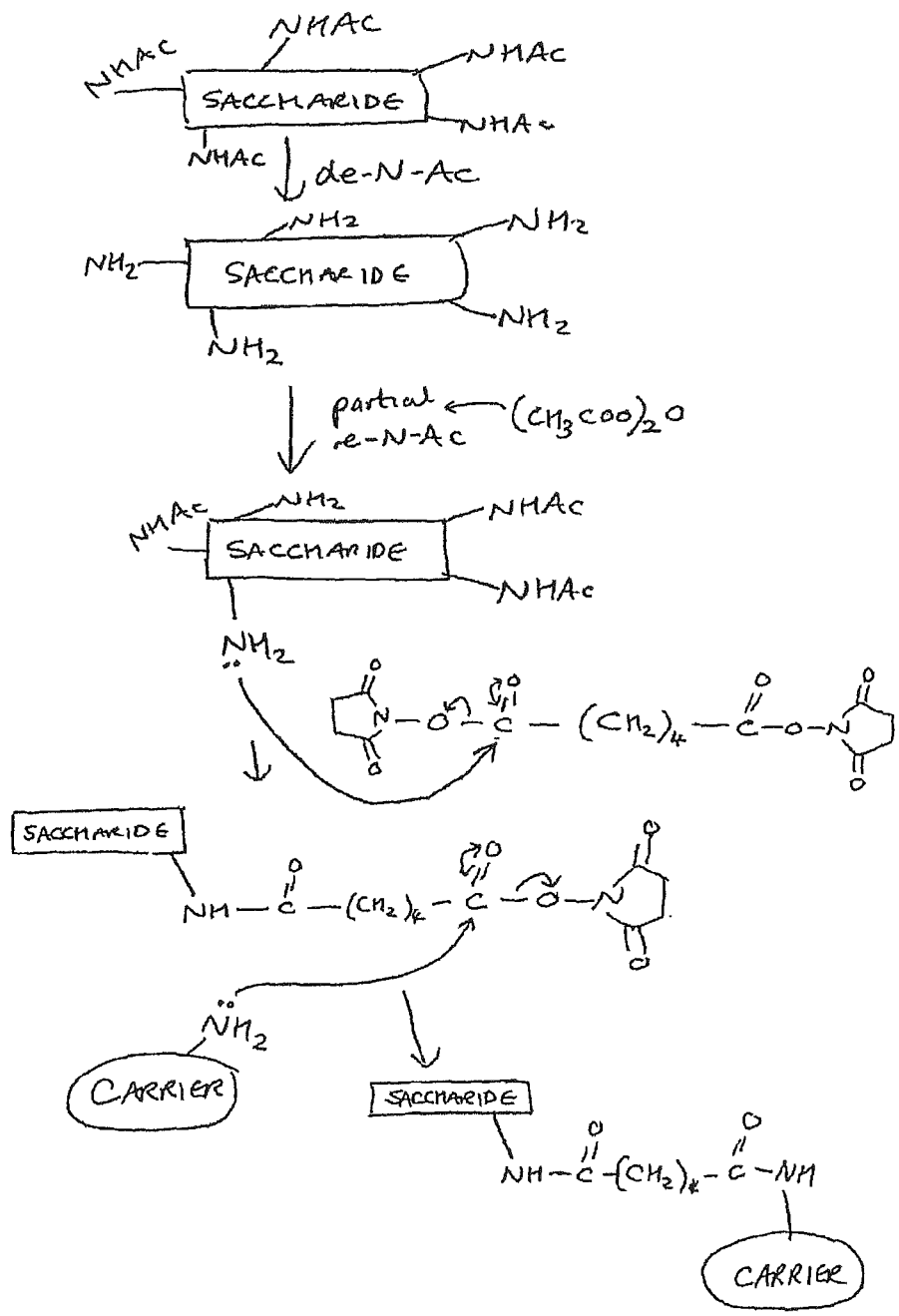
FIG. 7 shows a preferred conjugation reaction using the succiriimidyl diester of adipic acid, according to the second aspect of the invention.
Figure 8:
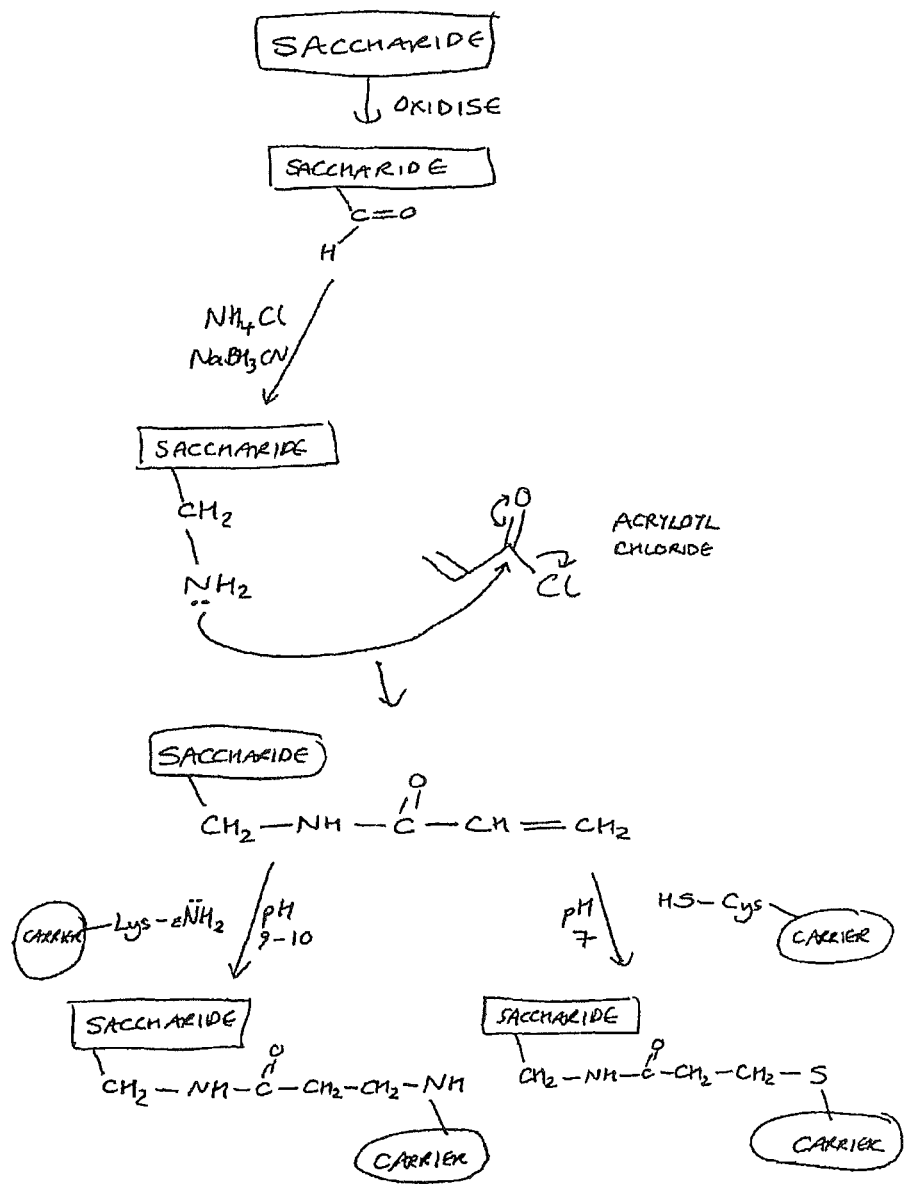
FIGS. 8 and 9 shows the use of (8) acryloylation and (9) a haloacylhalide, to prepare conjugates, after reductive amination of an aldehyde formed by oxidation of a terminal sialic acid residue.
Figure 9:
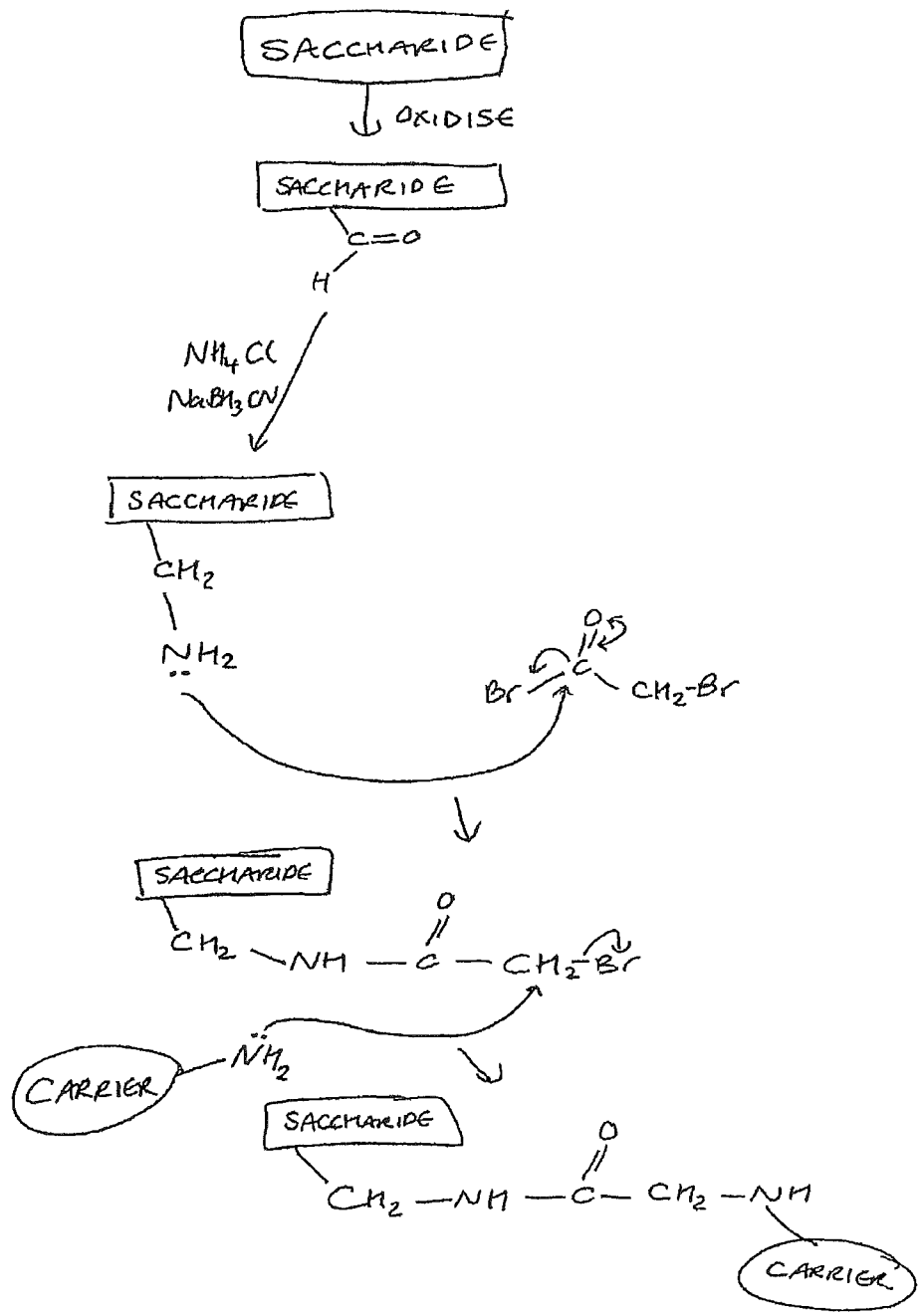

Capsular saccharide from GBS serotype Ib was purified as described in reference 15 and then re-acetylated as described above. The saccharide was de-N-acetylated to provide amine groups for linking. These amine groups were used to covalently conjugate the saccharides to monomeric tetanus toxoid (TT) either by direct reductive amination (on C8 of sialic acid, as described in the prior art) or via a SIDEA spacer (as described for meningococcal saccharides in ref. 218).

Sialic acid content in the conjugates was determined was performed according to the colorimetric method of ref. 219. The total saccharide amount was extrapolated from sialic acid content (sialic acids are on average 31% by weight of the polymer). Protein concentration in the conjugate was determined with the Micro BCA Protein Assay Kit (Pierce). A polysaccharide:protein weight ratio of between 1 and 4 was the target, and results were as follows:

| Conjugation | Saccharide (mg/ml) | Protein (mg/ml) | Ratio |
|---|---|---|---|
| Reductive amination | 1.740 | 1.271 | 1.37 |
| SIDEA spacer | 0.150 | 0.048 | 3.13 |

To investigate how the cross-linking ratio of conjugates could be affected, purified GBS Ia and Ib saccharides were subjected to varying degrees of oxidation and then conjugated to CRM197. Results were as follows

| % oxidation | Saccharide conc (mg/ml) | Protein conc (mg/ml) | Ratio (w/w) |
|---|---|---|---|
| | Ia | | |
| 5.0 | 1.188 | 0.468 | 2.54 |
| 14.2 | 1.360 | 0.776 | 1.75 |
| 44.7 | 1.018 | 0.690 | 1.48 |
| 79.0 | 2.989 | 2.012 | 1.49 |
| 86.0 | 1.737 | 1.074 | 1.62 |
| | Ib | | |
| 4.3 | 2.544 | 1.437 | 1.77 |
| 12.0 | 2.821 | 2.383 | 1.18 |
| 46.7 | 3.644 | 3.941 | 0.92 |
| 79.6 | 3.821 | 3.770 | 1.01 |
| 80.2 | 1.218 | 1.202 | 1.01 |

Similar experiments were used to study different protein carriers. CRM197 and tetanus toxoid were both used as carriers for GBS type III saccharide, and results were:

| % oxidation | Saccharide conc (mg/ml) | Protein conc (mg/ml) | Ratio (w/w) |
|---|---|---|---|
| | CRM197 | | |
| 4.3 | 3.270 | 1.150 | 2.84 |
| 17.5 | 4.130 | 2.894 | 1.43 |
| 40.9 | 3.056 | 1.822 | 1.68 |
| 61.8 | 3.165 | 2.358 | 1.34 |
| 78.9 | 4.230 | 4.502 | 0.94 |
| | Tetanus toxoid | | |
| 3.9 | 1.014 | 1.480 | 0.69 |
| 16.2 | 0.941 | 1.138 | 0.83 |
| 20.6 | 1.105 | 1.499 | 0.74 |
| 55.3 | 1.037 | 1.600 | 0.65 |

Three different carriers were compared for GBS type II and V saccharides: tetanus toxoid; CRM197; and human serum albumin. The degree of oxidation was 15.3% for the type V saccharide and 6.9% for the type II saccharide. Results were:

| Saccharide conc (mg/ml) | Protein conc (mg/ml) | Ratio (w/w) |
|---|---|---|
| | II | |
| 0.993 | 0.444 | 2.24 |
| 2.999 | 1.541 | 1.95 |
| 2.146 | 0.890 | 2.41 |
| | V | |
| 1.308 | 0.902 | 1.45 |
| 1.272 | 0.825 | 1.54 |
| 1.497 | 1.287 | 1.16 |

Human serum albumin was separately tested as a carrier for type Ia (6.7% oxidised), Ib (8.2% oxidised) and III (4.1% oxidised) saccharides:

| Type | Saccharide conc (mg/ml) | Protein conc (mg/ml) | Ratio (w/w) |
|---|---|---|---|
| Ia | 1.112 | 0.784 | 1.42 |
| Ib | 3.710 | 3.078 | 1.21 |
| III | 3.318 | 2.869 | 1.16 |

Conjugates of type Ia, Ib and III were made using four different carriers: tetanus toxoid; CRM197; GBS80; and GBS67. With the tetanus and CRM carriers the % s oxidation were 9.1% for Ia, 14.2% for Ib and 13% for III; with the GBS carriers the % s were 8.2%, 9.0% and 7.9%. Animals immunised with the conjugates were then tested for protection against the respective GBS types (i.e. homologous challenge), and results were as follows, expressed as the % of animals surviving lethal challenge:

|     | TT | CRM197 | GBS80 | GBS67 | PBS control |
| --- | --- | --- | --- | --- | --- |
| Ia  | 32 | 48 | 10 | 96 | 5 |
| Ib  | 52 | 33 | 65 | 92 | 15 |
| III | 76 | 60 | 71 | 82 | 0 |

In parallel experiments, with challenge by a GBS type V strain but no immunisation with a type V saccharide, results were as follows:

|   | TT | CRM197 | GBS80 | GBS67 | PBS control |
| --- | --- | --- | --- | --- | --- |
| V | 2 | 0 | 53 | 62 | 0 |

Thus the GBS carriers were able to provide some protection against the type V strain, and so the use of GBS proteins as carriers offers a background level of protein-mediated protection which can be supplemented by saccharides conjugated to the protein.

The level of free saccharide was tested for various conjugate lots, and results were as follows:

| GBS type | Carrier | free |
| --- | --- | --- |
| Ia | CRM | <1.0% |
|    | GBS80 | 3.5% |
|    | GBS67 | <1% |
| Ib | CRM | 1.8% |
|    | GBS80 | 14.8% |
|    | GBS67 | <1.0% |
| III | CRM | 1.6% |
|    | CRM | 4.4% |
|    | TetTox | 3.8% |
|    | GBS80 | 9.1% |
|    | GBS67 | <1.0% |

It will be understood that the invention has been described by way of example only and modifications may be made whilst remaining within the scope and spirit of the invention.

REFERENCES

The Contents of Which are Hereby Incorporated by Reference

[1] Paoletti et al. (1990) *J Biol Chem* 265:18278-83.
[2] Wessels et al. (1990) *J Clin Invest* 86:1428-33.
[3] Paoletti et al. (1992) *Infect Immun* 60:4009-14.
[4] Paoletti et al. (1992) *J Clin Invest* 89:203-9.
[5] Wessels et al. (1987) *Proc Natl Acad Sci USA* 84:9170-4.
[6] Wang et al. (2003) *Vaccine* 21:1112-7.
[7] Wessels et al. (1993) *Infect Immun* 61:4760-6
[8] Wessels et al. (1995) *J Infect Dis* 171:879-84.
[9] Baker et al. (2004) *J Infect Dis* 189:1103-12.
[10] U.S. Pat. No. 4,356,170.
[11] Paoletti & Kasper (2003) *Expert Opin Biol Ther* 3:975-84.
[12] U.S. Pat. Nos. 6,027,733 & 6,274,144.
[13] worldwideweb.polymer.de
[14] Lewis et al. (2004) *PNAS USA* 101:11123-8.
[15] International patent application PCT/IB2006/000626 (published as WO 2006/082527 A2, 'PURIFICATION OF STREPTOCOCCAL CAPSULAR POLYSACCHARID', claiming priority from GB-0502096.1 (CHIRON SRL).
[16] Ramsay et al. (2001) *Lancet* 357(9251):195-196.
[17] Lindberg (1999) *Vaccine* 17 Suppl 2:S28-36.
[18] Buttery & Moxon (2000) *J R Call Physicians Land* 34:163-168.
[19] Ahmad & Chapnick (1999) *Infect Dis Clin North Am* 13:113-33, vii.
[20] Goldblatt (1998) *J. Med. Microbial.* 47:563-567.
[21] European patent 0477508.
[22] U.S. Pat. No. 5,306,492.
[23] WO98/42721.
[24] Dick et al. in *Conjugate Vaccines* (eds. Cruse et al.) Karger, Basel, 1989, 10:48-114.
[25] Hermanson *Bioconjugate Techniques*, Academic Press, San Diego (1996) ISBN: 0123423368.
[26] Anonymous (January 2002) *Research Disclosure*, 453077.
[27] Anderson (1983) *Infect Immun* 39(1):233-238.
[28] Anderson et al. (1985) *J Clin Invest* 76(1):52-59.
[29] EP-A-0372501.
[30] EP-A-0378881.
[31] EP-A-0427347.
[32] WO93/17712
[33] WO94/03208.
[34] WO98/58668.
[35] EP-A-0471177.
[36] WO91/01146
[37] Falugi et al. (2001) *Eur J Immunol* 31:3816-24.
[38] Baraldo et al. (2004) *Infect Immun* 72:4884-87.
[39] EP-A-0594610.
[40] WO00/56360.
[41] WO02/091998.
[42] Kuo et al. (1995) *Infect Immun* 63:2706-13.
[43] WO01/72337
[44] WO00/61761.
[45] WO99/42130.
[46] WO2004/011027.
[47] WO96/40242.
[48] Lei et al. (2000) *Dev Biol (Basel)* 103:259-264.
[49] WO00/38711; U.S. Pat. No. 6,146,902.
[50] WO94/06467.
[51] U.S. Pat. No. 6,248,570.
[52] Wessels et al. (1989) *Infect Immun* 57:1089-94.
[53] U.S. Pat. No. 4,711,779.
[54] WO00/10599.
[55] U.S. Pat. No. 4,057,685.
[56] WO99/24578.
[57] WO99/36544.
[58] WO99/57280.
[59] WO00/22430,
[60] Tettelin et al. (2000) *Science* 287:1809-1815.
[61] WO96/29412.
[62] Pizza et al. (2000) *Science* 287:1816-1820.
[63] WO01/52885.
[64] Bjune et al. (1991) *Lancet* 338(8775):1093-1096.
[65] Fukasawa et al., (1999) *Vaccine* 17:2951-2958.
[66] Rosenqvist et al. (1998) *Dev. Biol. Stand* 92:323-333.
[67] Costantino et al. (1992) *Vaccine* 10:691-698.
[68] WO03/007985.
[69] Watson (2000) *Pediatr Infect Dis J* 19:331-332.
[70] Rubin (2000) *Pediatr Clin North Am* 47:269-285, v.
[71] Jedrzejas (2001) *Microbiol Mol Biol Rev* 65:187-207.
[72] Bell (2000) *Pediatr Infect Dis J* 19:1187-1188.
[73] Iwarson (1995) *APMIS* 103:321-326.
[74] Gerlich et al. (1990) *Vaccine* 8 Suppl:S63-68 & 79-80.
[75] Hsu et al. (1999) *Clin Liver Dis* 3:901-915.
[76] Gustafsson et al. (1996) *N. Engl. J. Med.* 334:349-355.
[77] Rappuoli et al. (1991) *TIBTECH* 9:232-238.

[78] Vaccines (2004) eds. Plotkin & Orenstein. ISBN 0-7216-9688-0.
[79] WO02/02606.
[80] Kalman et al. (1999) *Nature Genetics* 21:385-389.
[81] Read et al. (2000) *Nucleic Acids Res* 28:1397-406.
[82] Shirai et al. (2000) *J. Infect. Dis.* 181(Suppl 3):S524-S527.
[83] WO99/27105.
[84] WO00/27994.
[85] WO00/37494.
[86] WO99/28475.
[87] Ross et al. (2001) *Vaccine* 19:4135-4142.
[88] Sutter et al. (2000) *Pediatr Clin North Ain* 47:287-308.
[89] Zimmerman & Spann (1999) *Am Fam Physician* 59:113-118, 125-126.
[90] Dreesen (1997) *Vaccine* 15 Suppl:S2-6.
[91] *MMWR Moab Mortal Wkly Rep* 1998 Jan. 16; 47(1):12, 19.
[92] McMichael (2000) *Vaccine* 19 Suppl 1:S101-107.
[93] WO02/34771.
[94] Dale (1999) *Infect Dis Clin North Am* 13:227-43, viii.
[95] Ferretti et al. (2001) *PNAS USA* 98: 4658-4663.
[96] Kuroda et al. (2001) *Lancet* 357(9264):1225-1240; see also pages 1218-1219.
[97] Robinson & Torres (1997) *Seminars in Immunology* 9:271-283.
[98] Donnelly et al. (1997) *Annu Rev Immunol* 15:617-648.
[99] Scott-Taylor & Dalgleish (2000) *Expert Opin Investig Drugs* 9:471-480.
[100] Apostolopoulos & Plebanski (2000) *Curr Opin Mol Ther* 2:441-447.
[101] Ilan (1999) *Curr Opin Mol Ther* 1:116-120.
[102] Dubensky et al. (2000) *Mol Med* 6:723-732.
[103] Robinson & Pertmer (2000) *Adv Virus Res* 55:1-74.
[104] Donnelly et al. (2000) *Am J Respir Crit Care Med* 162(4 Pt 2):S190-193.
[105] Davis (1999) *Mt. Sinai J. Med.* 66:84-90.
[106] Paoletti et al, (2001) *Vaccine* 19:2118-2126.
[107] WO00/56365.
[108] Gennaro (2000) *Remington: The Science and Practice of Pharmacy.* 20th edition, ISBN: 0683306472.
[109] WO03/009869.
[110] Almeida & Alpar (1996) *J. Drug Targeting* 3:455-467.
[111] Agarwal & Mishra (1999) *Indian J Exp Biol* 37:6-16.
[112] WO00/53221.
[113] Jakobsen et al. (2002) *Infect Immun* 70:1443-1452.
[114] Bergquist et al. (1998) *APMIS* 106:800-806.
[115] Baudner et al. (2002) *Infect Immun* 70:4785-4790.
[116] Ugozzoli et al. (2002) *J Infect Dis* 186:1358-1361.
[117] *Vaccine Design* . . . (1995) eds. Powell & Newman. ISBN: 030644867X. Plenum.
[118] WO00/23105.
[119] WO90/14837.
[120] Podda (2001) *Vaccine* 19:2673-80.
[121] Frey et al. (2003) *Vaccine* 21:4234-7.
[122] U.S. Pat. No. 6,299,884.
[123] U.S. Pat. No. 6,451,325.
[124] U.S. Pat. No. 5,057,540.
[125] WO96/33739.
[126] EP-A-0109942.
[127] WO96/11711.
[128] WO00/07621.
[129] Barr et al. (1998) *Advanced Drug Delivery Reviews* 32:247-271.
[130] Sjolanderet et al. (1998) *Advanced Drug Delivery Reviews* 32:321-338.
[131] Niikura et al. (2002) *Virology* 293:273-280.
[132] Lenz et al. (2001) *J Immunol* 166:5346-5355.
[133] Pinto et al. (2003) *J Infect Dis* 188:327-338.
[134] Gerber et al. (2001) *Virol* 75:4752-4760.
[135] WO03/024480
[136] WO03/024481
[137] Gluck et al. (2002) *Vaccine* 20:B10-B16.
[138] EP-A-0689454.
[139] Johnson et al. (1999) *Bioorg Med Chem Lett* 9:2273-2278.
[140] Evans et al. (2003) *Expert Rev Vaccines* 2:219-229.
[141] Meraldi et al. (2003) *Vaccine* 21:2485-2491.
[142] Pajak et al. (2003) *Vaccine* 21:836-842.
[143] Kandimalla et al. (2003) *Nucleic Acids Research* 31:2393-2400.
[144] WO02/26757.
[145] WO99/62923.
[146] Krieg (2003) *Nature Medicine* 9:831-835.
[147] McCluskie et al. (2002) *FEMS Immunology and Medical Microbiology* 32:179-185.
[148] WO98/40100.
[149] U.S. Pat. No. 6,207,646.
[150] U.S. Pat. No. 6,239,116.
[151] U.S. Pat. No. 6,429,199.
[152] Kandimalla et al. (2003) *Biochemical Society Transactions* 31 (part 3):654-658.
[153] Blackwell et al. (2003) *J Immunol* 170:4061-4068.
[154] Krieg (2002) *Trends Immunol* 23:64-65.
[155] WO01/95935.
[156] Kandimalla et al. (2003) *BBRC* 306:948-953.
[157] Bhagat et al. (2003) *BBRC* 300:853-861.
[158] WO03/035836.
[159] WO95/17211.
[160] WO98/42375.
[161] Beignon et al. (2002) *Infect Immun* 70:3012-3019.
[162] Pizza et al. (2001) *Vaccine* 19:2534-2541.
[163] Pizza et al. (2000) *Int J Med Microbiol* 290:455-461,
[164] Scharton-Kersten et al. (2000) *Infect Immun* 68:5306-5313.
[165] Ryan et al. (1999) *Infect Immun* 67:6270-6280.
[166] Partidos et al, (1999) *Immunol Lett* 67:209-216.
[167] Peppoloni et al. (2003) *Expert Rev Vaccines* 2:285-293.
[168] Pine et al. (2002) *J Control Release* 85:263-270.
[169] Domenighini et al. (1995) *Mol Microbiol* 15:1165-1167.
[170] WO99/40936.
[171] WO99/44636.
[172] Singh et al] (2001) *J Cont Release* 70:267-276.
[173] WO99/27960.
[174] U.S. Pat. No. 6,090,406
[175] U.S. Pat. No. 5,916,588
[176] EP-A-0626169.
[177] WO99/52549.
[178] WO01/21207.
[179] WO01/21152.
[180] Andrianov et al. (1998) *Biomaterials* 19:109-115.
[181] Payne et al. (1998) *Adv Drug Delivery Review* 31:185-196.
[182] Stanley (2002) *Clin Exp Dermatol* 27:571-577.
[183] Jones (2003) *Curr Opin Investig Drugs* 4:214-218.
[184] WO04/60308
[185] WO04/64759.
[186] WO99/11241.
[187] WO94/00153.
[188] WO98/57659.
[189] European patent applications 0835318, 0735898 and 0761231.
[190] Glezen & Alpers (1999) *Clin. Infect. Dis.* 28:219-224

[191] Madoff et al, (1994) *J Clin Invest* 94:286-92.
[192] Paoletti et al. (1994) *Infect Immun* 62:3236-43.
[193] WO03/093306.
[194] WO2004/018646.
[195] WO2004/041157.
[196] Geysen et al. (1984) *PNAS USA* 81:3998-4002.
[197] Carter (1994) *Methods Mol Biol* 36:207-23.
[198] Jameson, B A et al. 1988, *CABIOS* 4(1):181-186.
[199] Raddrizzani & Hammer (2000) *Brief Bioinform* 1(2): 179-89.
[200] De Lalla et al. (1999) *J. Immunol.* 163:1725-29.
[201] Brusic et al. (1998) *Bioinformatics* 14(2):121-30
[202] Meister et al. (1995) *Vaccine* 13(6):581-91.
[203] Roberts et al. (1996) *AIDS Res Hum Retroviruses* 12(7): 593-610.
[204] Maksyutov & Zagrebelnaya (1993) *Comput Appl Biosci* 9(3):291-7.
[205] Feller & de la Cruz (1991) *Nature* 349(6310:720-1.
[206] Hopp (1993) *Peptide Research* 6:183-190.
[207] Welling et al. (1985) *FEBS Lett.* 188:215-218.
[208] Davenport et al. (1995) *Immunogenetics* 42:392-297.
[209] Bodanszky (1993) *Principles of Peptide Synthesis* (ISBN: 0387564314).
[210] Fields et al. (1997) *Meth Enzymol* 289: *Solid-Phase Peptide Synthesis*. ISBN: 0121821900.
[211] Chan & White (2000) *Fmoc Solid Phase Peptide Synthesis*. ISBN: 0199637245.
[212] Kullmann (1987) *Enzymatic Peptide Synthesis*. ISBN: 0849368413.
[213] Ibba (1996) *Biotechnol Genet Eng Rev* 13:197-216.
[214] Qi Chen et al. (2002) *Infect Immun* 70:6409-15.
[215] Beckmann et al. (2002) *Infect Immun* 70:2869-76.
[216] Cheng et al. (2002) *Infect Immun* 70:2408-13.
[217] Cheng et al, (2001) *Infect Immun* 69:2302-8.
[218] WO03/007985.
[219] Svennerholm (1958) *Acta Chem. Scand.* 12:547-554.

---

The invention claimed is:

1. A conjugated saccharide comprising a *Streptococcus agalactiae* capsular saccharide moiety joined to a carrier via a linker moiety, wherein:
the linker moiety is attached to a sialic acid residue in the capsular saccharide moiety,
the capsular saccharide is from a group B *streptococcus* (GBS) bacterium having a serotype selected from the group consisting of Ia, Ib, II, III, V, and combinations thereof,
the capsular saccharide is partially or fully deacetylated,
the carrier is the GBS protein antigen GBS80, and
a weight ratio of capsular saccharide to GBS protein antigen is from 1:5 to 5:1.

2. A conjugated saccharide comprising a *Streptococcus agalactiae* capsular saccharide moiety joined to a carrier via a linker moiety, wherein:
the linker moiety is attached to a sialic acid residue in the capsular saccharide moiety,
the capsular saccharide is from a group B *streptococcus* (GBS) bacterium having a serotype selected from the group consisting of Ia, Ib, II, III, V, and combinations thereof,
the capsular saccharide is partially or fully deacetylated,
the carrier is the GBS protein antigen GBS80, and
aldehyde groups are introduced into between 5% and 50% of the sialic acid monosaccharide units of the capsular saccharide.

3. A conjugated saccharide of comprising a *Streptococcus agalactiae* capsular saccharide moiety joined to a carrier via a linker moiety, wherein:
the linker moiety is attached to a sialic acid residue in the capsular saccharide moiety,
the capsular saccharide is from a group B *streptococcus* (GBS) bacterium having a serotype selected from the group consisting of Ia, Ib, II, III, V, and combinations thereof,
the capsular saccharide is partially or fully deacetylated,
the carrier is the GBS protein antigen GBS80,
the linker moiety is bonded to the sialic acid residue in the capsular saccharide moiety and bonded to the carrier via a terminal —NH— or a terminal —C(O)— of the linker moiety, and
the linker moiety has the formula —NH—C(O)—(CH$_2$)$_n$—C(O)—,
wherein n is an integer from 1-9.

4. A conjugated saccharide comprising a *Streptococcus agalactiae* capsular saccharide moiety joined to a carrier via a linker moiety, wherein:
the linker moiety is attached to a sialic acid residue in the capsular saccharide moiety,
the capsular saccharide is from a group B *streptococcus* (GBS) bacterium having a serotype selected from the group consisting of Ia, Ib, II, III, V, and combinations thereof,
the capsular saccharide is partially or fully deacetylated,
the carrier is the GBS protein antigen GBS80,
the linker moiety is bonded to the sialic acid residue in the capsular saccharide moiety and bonded to the carrier via a terminal —NH— or a terminal —C(O)— of the linker moiety, and
the linker moiety has the formula —C(O)—(CH$_2$)$_n$αC(O)—, wherein n is an integer from 1-10.

5. A composition comprising the conjugated saccharide of claim 1 and one or more further antigens.

6. The composition of claim 5, wherein the one or more further antigens include an antigen from a non-GBS pathogen.

7. The composition of claim 6, wherein the antigen from the non-GBS pathogen is a diphtheria antigen.

8. The composition of claim 5, further comprising an adjuvant.

9. A method for eliciting an immune response in a subject, the method comprising administering to the subject the composition of claim 5 in an amount sufficient to elicit the immune response.

10. The method of claim 9, wherein the immune response comprises the generation of antibodies in the subject.

* * * * *